(12) United States Patent
Sahin et al.

(10) Patent No.: US 11,222,711 B2
(45) Date of Patent: Jan. 11, 2022

(54) PREDICTING IMMUNOGENICITY OF T CELL EPITOPES

(71) Applicants: BioNTech SE, Mainz (DE);
TRON—TRANSLATIONALE ONKOLOGIE AN DER UNIVERSITÄTSMEDIZIN DER JOHANNES GUTENBERG—UNIVERSITAT MAINZ GEMEINNUTZIGE GMBH, Mainz (DE)

(72) Inventors: Ugur Sahin, Mainz (DE); Arbel David Tadmor, Bodenheim (DE); John Christopher Castle, Mainz (DE); Sebastian Boegel, Obermoschel (DE); Martin Löwer, Wiesbaden (DE)

(73) Assignees: BioNTech SE, Mainz (DE); TRON—Translationale Onkologie an der Universitätsmedizin der Johannes Gutenberg-Universität Mainz gGmbH, Mainz (DE)

(*) Notice: Subject to any disclaimer, the term of this patent is extended or adjusted under 35 U.S.C. 154(b) by 913 days.

(21) Appl. No.: 14/787,110

(22) PCT Filed: May 7, 2014

(86) PCT No.: PCT/EP2014/001232
§ 371 (c)(1),
(2) Date: Oct. 26, 2015

(87) PCT Pub. No.: WO2014/180569
PCT Pub. Date: Nov. 13, 2014

(65) Prior Publication Data
US 2016/0125129 A1    May 5, 2016

(30) Foreign Application Priority Data

May 10, 2013    (WO) .................. PCT/EP2013/001400

(51) Int. Cl.
| | | |
|---|---|---|
| G16B 20/20 | (2019.01) | |
| G16B 20/00 | (2019.01) | |
| A61K 39/00 | (2006.01) | |
| C12Q 1/6886 | (2018.01) | |

(52) U.S. Cl.
CPC .......... G16B 20/20 (2019.02); A61K 39/0011 (2013.01); C12Q 1/6886 (2013.01); G16B 20/00 (2019.02); *A61K 2039/80* (2018.08); *C12Q 2600/156* (2013.01)

(58) Field of Classification Search
None
See application file for complete search history.

(56) References Cited

U.S. PATENT DOCUMENTS

| | | |
|---|---|---|
| 4,897,355 A | 1/1990 | Eppstein et al. |
| 5,264,618 A | 11/1993 | Felgner et al. |
| 5,703,055 A | 12/1997 | Felgner et al. |
| 6,251,399 B1 | 6/2001 | Diamond et al. |
| 6,472,176 B2 | 10/2002 | Kovesdi et al. |
| 6,500,641 B1 | 12/2002 | Chen et al. |
| 6,586,410 B1 | 7/2003 | Wheeler et al. |
| 7,303,881 B2 | 12/2007 | Huang et al. |
| 7,462,354 B2 | 12/2008 | Sette et al. |
| 7,790,696 B2 | 9/2010 | Gregoriadis |
| 8,140,270 B2 | 3/2012 | Kingsmore et al. |
| 8,217,016 B2 | 7/2012 | Hoerr et al. |
| 8,349,558 B2 | 1/2013 | Fatho et al. |
| 8,703,142 B2 | 4/2014 | Diamond et al. |
| 8,853,283 B2 | 10/2014 | Platscher et al. |
| 8,877,206 B2 | 11/2014 | Chen et al. |
| 9,115,402 B2 | 8/2015 | Hacohen et al. |
| 2007/0025968 A1 | 2/2007 | Van Der Burg et al. |
| 2009/0055944 A1 | 2/2009 | Korman et al. |
| 2009/0217401 A1 | 8/2009 | Korman et al. |
| 2012/0237975 A1 | 9/2012 | Schrum et al. |
| 2013/0115272 A1 | 5/2013 | de Fougerolles et al. |
| 2013/0123481 A1 | 5/2013 | de Fougerolles et al. |
| 2013/0156849 A1 | 6/2013 | de Fougerolles et al. |
| 2013/0203115 A1 | 8/2013 | Schrum et al. |
| 2013/0237593 A1 | 9/2013 | de Fougerolles et al. |
| 2013/0237594 A1 | 9/2013 | de Fougerolles et al. |
| 2013/0244278 A1 | 9/2013 | de Fougerolles et al. |

(Continued)

FOREIGN PATENT DOCUMENTS

| | | |
|---|---|---|
| EP | 0839912 A1 | 5/1998 |
| EP | 1242108 A1 | 9/2002 |

(Continued)

OTHER PUBLICATIONS

Florea et al. Proceedings of the Computational Systems Bioinformatics, 2003, 1-10.*

(Continued)

*Primary Examiner* — Michael L Borin
(74) *Attorney, Agent, or Firm* — Choate, Hall & Stewart LLP; Brenda Herschbach Jarrell; Janet M. Tse

(57) ABSTRACT

The present invention relates to methods for predicting T cell epitopes. In particular, the present invention relates to methods for predicting whether modifications in peptides or polypeptides such as tumor-associated neoantigens are immunogenic or not. The methods of the invention are useful, in particular, for the provision of vaccines which are specific for a patient's tumor and, thus, in the context of personalized cancer vaccines.

34 Claims, 13 Drawing Sheets

Figure 1:
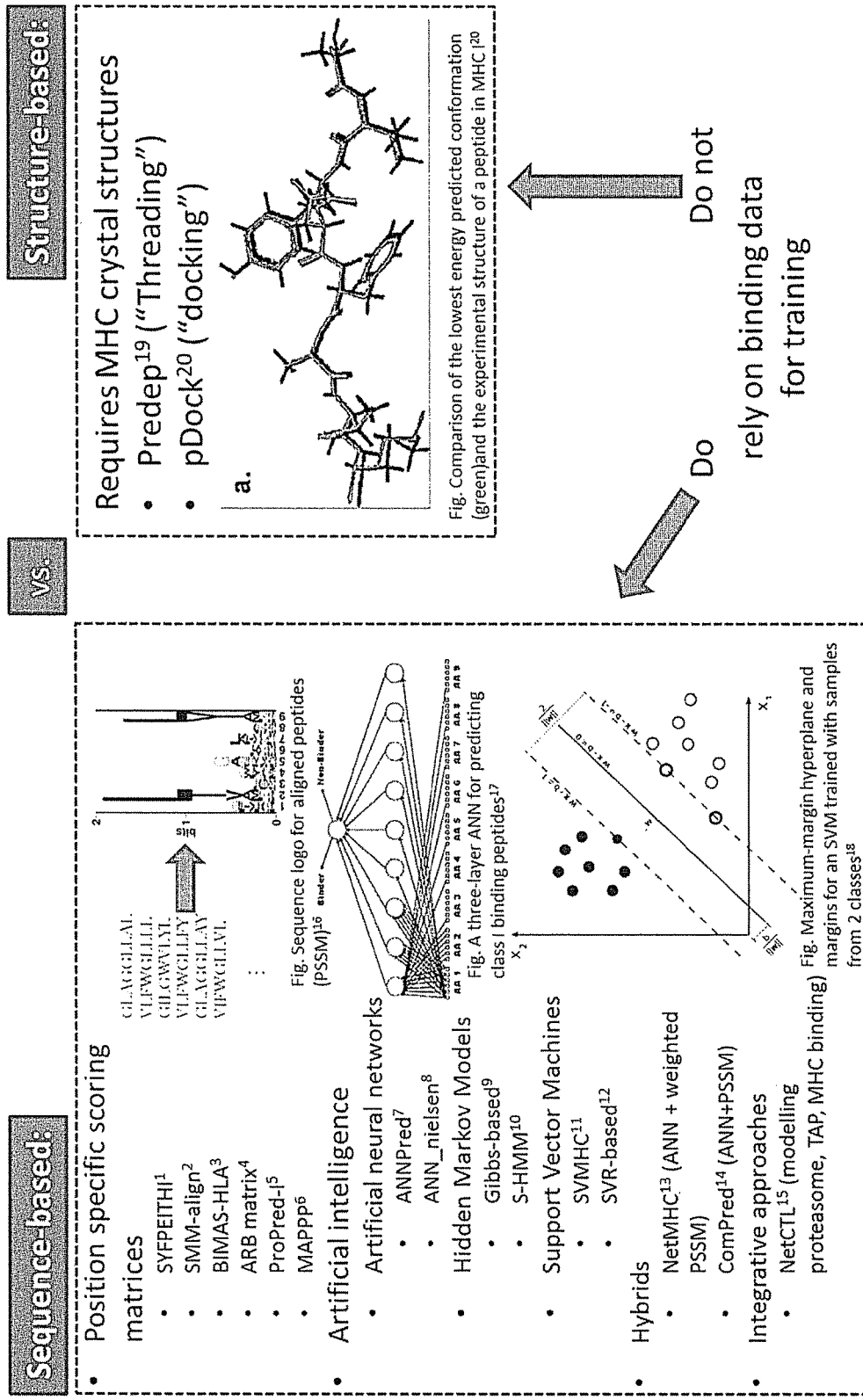

Specification includes a Sequence Listing.

(56) References Cited

U.S. PATENT DOCUMENTS

| | | |
|---|---|---|
| 2013/0244279 A1 | 9/2013 | de Fougerolles et al. |
| 2013/0245106 A1 | 9/2013 | de Fougerolles et al. |
| 2013/0245107 A1 | 9/2013 | de Fougerolles et al. |
| 2013/0255281 A1 | 10/2013 | Bray |
| 2013/0266640 A1 | 10/2013 | de Fougerolles et al. |
| 2014/0010861 A1 | 1/2014 | Bancel et al. |
| 2014/0147454 A1 | 5/2014 | Chakraborty et al. |
| 2014/0178438 A1 | 6/2014 | Sahin et al. |
| 2015/0017211 A1 | 1/2015 | de Fougerolles et al. |
| 2015/0030576 A1 | 1/2015 | Bancel |
| 2015/0167017 A1 | 6/2015 | Roy et al. |

FOREIGN PATENT DOCUMENTS

| | | |
|---|---|---|
| EP | 2569633 A2 | 3/2013 |
| WO | 1994023031 A1 | 10/1994 |
| WO | WO-97/40852 A1 | 11/1997 |
| WO | 1998014464 A1 | 4/1998 |
| WO | 1999024566 A1 | 5/1999 |
| WO | 1999052503 A2 | 10/1999 |
| WO | 2000/20029 A1 | 4/2000 |
| WO | 2000067761 A1 | 11/2000 |
| WO | 2001047959 A2 | 7/2001 |
| WO | 2001093902 A2 | 12/2001 |
| WO | 2002048377 A2 | 6/2002 |
| WO | 2002083714 A2 | 10/2002 |
| WO | 02/098443 A2 | 12/2002 |
| WO | 2003051401 A2 | 6/2003 |
| WO | 2003068257 A1 | 8/2003 |
| WO | 2003106692 A2 | 12/2003 |
| WO | 2004004743 A1 | 1/2004 |
| WO | 2005030250 A2 | 4/2005 |
| WO | 2005039533 A1 | 5/2005 |
| WO | 2005040816 A1 | 5/2005 |
| WO | 2005110338 A2 | 11/2005 |
| WO | 2006121168 A1 | 11/2006 |
| WO | 2007024708 A2 | 3/2007 |
| WO | 2007025760 A2 | 3/2007 |
| WO | 2007031222 A2 | 3/2007 |
| WO | 2007101227 A2 | 9/2007 |
| WO | 2008080468 A1 | 7/2008 |
| WO | 2008083174 A2 | 7/2008 |
| WO | 2008085562 A2 | 7/2008 |
| WO | 2008116078 A2 | 9/2008 |
| WO | 2008156712 A1 | 12/2008 |
| WO | 2009053041 A2 | 4/2009 |
| WO | 2009118296 A2 | 10/2009 |
| WO | 2009129227 A1 | 10/2009 |
| WO | 2010066418 A1 | 6/2010 |
| WO | 2011012316 A2 | 2/2011 |
| WO | 2011143656 A2 | 11/2011 |
| WO | 2012045075 A1 | 4/2012 |
| WO | 2012045082 A2 | 4/2012 |
| WO | 2012135805 A2 | 10/2012 |
| WO | 2012159729 A1 | 11/2012 |
| WO | 2012159754 | 11/2012 |
| WO | WO-2012/159643 A1 | 11/2012 |
| WO | 2013040142 A2 | 3/2013 |
| WO | 2013052523 A1 | 4/2013 |
| WO | 2013090648 A1 | 6/2013 |
| WO | 2013124701 A2 | 8/2013 |
| WO | 2013151663 A1 | 10/2013 |
| WO | 2013151664 A1 | 10/2013 |
| WO | 2013151665 A2 | 10/2013 |
| WO | 2013151672 A2 | 10/2013 |
| WO | 2014012051 A1 | 1/2014 |
| WO | 2014071219 A1 | 5/2014 |
| WO | 2014093924 A1 | 6/2014 |
| WO | 2014144039 A1 | 9/2014 |
| WO | 2014144711 A1 | 9/2014 |
| WO | 2014144767 A1 | 9/2014 |
| WO | 2014152027 A1 | 9/2014 |
| WO | 2014152030 A1 | 9/2014 |
| WO | 2014152031 A1 | 9/2014 |
| WO | 2014152211 A1 | 9/2014 |
| WO | 2014159813 A1 | 10/2014 |
| WO | 2014160243 A1 | 10/2014 |
| WO | 2014164253 A1 | 10/2014 |
| WO | 2014168874 A2 | 10/2014 |
| WO | WO-2014/180490 A1 | 11/2014 |
| WO | 2015014375 A1 | 2/2015 |
| WO | 2015034925 A1 | 3/2015 |
| WO | 2015034928 A1 | 3/2015 |
| WO | 2015038892 A1 | 3/2015 |
| WO | 2015043613 A1 | 4/2015 |
| WO | 2015051169 A2 | 4/2015 |
| WO | 2015051173 A2 | 4/2015 |
| WO | 2015058780 A1 | 4/2015 |
| WO | 2015085318 A2 | 6/2015 |
| WO | 2015089511 A2 | 6/2015 |
| WO | 2015117620 A1 | 8/2015 |
| WO | 2015164674 A1 | 10/2015 |
| WO | 2015172843 A1 | 11/2015 |
| WO | 2016062323 A1 | 4/2016 |
| WO | 2016/091391 A1 | 6/2016 |
| WO | 2016107877 A1 | 7/2016 |
| WO | 2016155809 A1 | 10/2016 |
| WO | WO-2017/106638 A1 | 6/2017 |
| WO | WO-2018/195357 A1 | 10/2018 |
| WO | WO-2018/227030 A1 | 12/2018 |
| WO | WO-2019/050994 A1 | 3/2019 |
| WO | WO-2019/075112 A1 | 4/2019 |
| WO | WO-2019/104203 A1 | 5/2019 |
| WO | WO-2019/168984 A1 | 9/2019 |

OTHER PUBLICATIONS

Feng et al. J Mol. Evol., 21:112-125, 1985.*
Kreiter et al. (OncoImmunology, 1,5, 768-769, 2012.*
Greenblatt et al. Oncogene (2003) 22, 1150-1163.*
Le Calvez-Kelm et al. Breast Cancer Research 2011, 13:R6, 1-12.*
International Search Report of PCT/EP2014/001232 dated Jun. 8, 2014.
Michielin O, et al., "Binding Free Energy Differences In A TRC-Peptide-MHC Complex Induced By A Peptide Mutation: A Simulation Analysis", Journal of Molecular Biology, Academic Press, United Kingdom, vol. 324, No. 3, Nov. 29, 2002, pp. 547-569.
Wan S, et at., "Molecular Basis Of Peptide Recognition By The TRC: Affinity Differences Calculated Using Large Scale Computing", Journal of Immunology, vol. 175, No. 3, Aug. 2005, pp. 1715-1723.
Lafuente E, et al., "Prediction of MHC-Peptide Binding: A Systematic And Comprehensive Overview", Current Pharmaceutical Design, vol. 15, No. 28, Oct. 1, 2009, pp. 3209-3220.
International Preliminary Report on Patentability Chapter 1, dated Nov. 10, 2015, Filed in relation to PCT Application No. PCT/EP2013/001400, Filed May 10, 2013, Entitled "Predicting Immunogenicity of T Cell Epitopes," By Applicant "Biontech AG," 7 pages.
International Search Report (ISR), dated Jan. 2, 2014, Filed in relation to PCT Application No. PCT/EP2013/001400, Filed May 10, 2013, Entitled "Predicting Immunogenicity of T Cell Epitopes," By Applicant "Biontech AG," 5 pages.
Written Opinion of the International Search Authority, dated Jan. 2, 2014, Filed in relation to PCT Application No. PCT/EP2013/001400, Filed May 10, 2013, Entitled "Predicting Immunogenicity of T Cell Epitopes," By Applicant "Biontech AG," 6 pages.
International Preliminary Report on Patentability Chapter I, dated Nov. 10, 2015, Filed in relation to PCT Application No. PCT/EP2014/001232, Filed May 7, 2014, Entitled "Predicting Immunogenicity of T Cell Epitopes," By Applicant "Biontech AG," 7 pages.
International Search Report (ISR), dated Aug. 6, 2012, Filed in relation to PCT Application No. PCT/EP2014/001232, Filed May 7, 2014, Entitled "Predicting Immunogenicity of T Cell Epitopes," By Applicant "Biontech AG," 5 pages.
Written Opinion of the International Search Authority, dated Aug. 6, 2014, Filed in relation to PCT Application No. PCT/EP2014/001232, Filed May 7, 2014, Entitled "Predicting Immunogenicity of T Cell Epitopes," By Applicant "Biontech AG," 6 pages.

(56) References Cited

OTHER PUBLICATIONS

Japanese Office Action issued in related Japanese Application No. 2016-512248, dated Apr. 24, 2018.
Dang et al., "ReplacementMatrix: a web werverfor maximum-likelihood estimation of amino acid replacement rate matrices," Bioinformatics, vol. 27, No. 19, 2011, pp. 2758-2760.
Agrawal et al., Trend in Biotechnology, 14(10): 376-387, 1996.
Mayer et al. Anticancer Research 25:3917-3924 (2005).
Bei et al.J Immunother. May 1998;21(3):159-69.
Boczkowski et al. (1996). "Dendritic cells pulsed with RNA are potent antigen-presenting cells in vitro and in vivo," J. Exp Med 184: 465-472.
Bowerman, NA. "Engineering the binding properties of the T cell receptor: peptide: MHC ternary complex that governs T cell activity " Mol. Immun. 46: 3000-3008, 2009.
Brickner et al. J. Exp. Med 193(2) 195-205 (2001).
Del Val et al., Cell, vol. 66, Issue 6, Sep. 20, 1991, pp. 1145-1153.
Conry et al. (1994). "Immune response to a carcinoembryonic antigen polynucleotide vaccine," Cancer Res. 54:1164-1168.
Conry et al. (1995). "Characterization of a messenger RNA polynucleotide vaccine vector," Cancer Res. 55:1397-1400.
Coulie et al. (1995). "A mutated intron sequence codes for an antigenic peptide recognized by cytolytic T lymphocytes on a human melanoma," Proc. Natl. Acad. Sci. USA 92: 7976-7980.
Dengjel, J. et al. "Glycan side chains on naturally presented MHC class II ligands" J. Mass Spectrom, 2005.
Ding et al. "Genome remodeling in a basal-like breast cancer metastatis and xenograft." Nature, 464: 999-1005, 2010.
Dolgin, Nature 522:26.
Fritsch, E. F. et al. "HLA-Binding Properties of Tumor Neoepitopes in Humans" Cancer Immunology Research, 2:522-529, 2014.
Gnirke, A. "Solution hybrid selection with ultra-long oligonucleotides for massively parallel targeted sequencing" Nat. Biotechnol, 2009.
Goya, R. et al. "SNVMix: predicting single nucleotide variants from next-generation sequencing of tumors, Bioinformatics" Bioinformatics, 26: 730-736, 2010.
Gryaznov et al., Biochim. Biophys. Acta, 1489:131-140, 1999.
Guyre et al., Cancer Immunother (1997) 45:146-148.
Hacohen Decl. dated Feb. 16, 2014 filed in U.S. Appl. No. 13/108,610, 10 pages.
Hoerr et al. (2000). "In vivo application of RNA leads to induction of specific cytotoxic T lymphocytes and antibodies," Eur. J. Immunol. 30:1-7.
Johanning et al. Nucleic Acids Res. May 11, 1995; 23(9): 1495-1501.
Kenter, G. G. et al. "Phase I Immunotherapeutic Trial with Long Peptides Spanning the E6 and E7 sequences of High-risk human papillomavirus 16 in End-stage cervical cancer patients shows low toxicity and robust immunogenicity." Clinical Cancer Research, 14:169-177, 2008.
Keogh, E. et al. "Identification of New Epitopes from Four Different Tumor-Associated Antigens: Recognition of Naturally Processed Epitopes Correlates with HLA-A*0201-Binding Affinity" J Immunol. 167: 787-796, 2001.
Lemmel, Claudia et al., "Differential quantitative analysis of MHC ligands by mass spectrometry using stable isotope labeling" Nat Biotechnol, 2004.
Lennerz et al. (2005). "The response of autologous T cells to a human melanoma is dominated by mutated neoantigens," Proc. Natl. Acad. Sci. USA 102: 16013-16018.
Ley et al. (2008). "DNA sequencing of a cytogenetically normal acute myeloid leukaemia genome," Nature 456: 66-72.
Li et al., Cancer Genome Sequencing and Its Implications for Personalized Cancer Vaccine, Cancer 2011, 3, 4191-4211.
Maksyutov and Zagrebelnaya (1993). "ADEPT: a computer program for prediction of protein antigenic determinants," Comput. Appl. Biosci. 9:291-297.
Mandelboim et al. (1995). "Regression of established murine carcinoma metastases following vaccination with tumour-associated antigen peptides," Nature Medicine 1:1179-1183.
Mardis, ER. "Recurring Mutations Found by Seuencing an Acute Myeloid Leukemia Genome" New England J. Med. 361: 1058-1066, 2009.
Margulies, Marcel et al., "Genome Sequencing in Open Microfabricated High Density Picoliter Reactors " Nature, 2005.
Martinon et al. (1993). Induction of virus-specific cytotoxic T lymphocytes in vivo by liposome-entrapped mRNA. Eur. J. Immunol 23,1719-1722.
Meyerson, M. et al. "Advances in understanding cancer genomes through second-generation sequencing" Nature Rev. Genetics. 11:685-695, 2010.
Monach et al. (1995). "A unique tumor antigen produced by a single amino acid substitution," Immunity 2: 45-59.
Mortazavi (2008). "Mapping and quantifying mammalian transcriptomes by RNA-Seq," Nature Methods 5: 621-628.
Parker et al., J. Immunol. 152 (1994), 163-175.
Parkhurst, MR et al. "Improved Induction of Melanoma-reactive CTL with peptides from the melanoma antigen gp100 modified at HLA-A*0201-binding residues" J Immunol. 157: 2549-2548, 1996.
Parmiani, G. et al. "Unique Human Tumor Antigens: Immunobiology and Use in Clinical Trials." The Journal of Immunology, 178: 1975-1979, 2007.
Perissi et al., Electron Spin Resonance and Differential Scanning Calorimetry as Combined Tools for the Study of Liposomes in the Presence of Long Chain Nitroxides, 106 J. of Phys. Chem. B 10468 (2002).
Pfohl et al., Biological Polyelectrolyte Complexes in Solution and Confined on Patterned Surfaces, 198-200 Colloids & Surfaces A: Physicochemical and Eng. Aspects 613 (2002).
Pilla, L. et al. "Multipeptide vaccination in cancer patients" Expert Opinion on Biological Therapy, 9: 1043-1055, 2009.
Pleasance, E. et al. "A comprehensive catalogue of somatic mutaitons from a human cancer genome." Nature, 463: 191-196, 2010.
Pleasance, E. et al. "A small-cell lung cancer genome with complex signatures of tobacco exposure." Nature, 463: 184-190, 2010.
Rammensee (2006). "Some considerations on the use of peptides and mRNA for therapeutic vaccination against cancer," Immunol Cell Biol. 84(3):290-4.
Rammansee 2008, Chapter 50: Cancer Vaccines: Some Basic Considerations, Genomic and Personalized Medicine, Hungtington and Ginsburg. E-published on Nov. 11, 2008.
Rammensee et al. (2002). "Toward patient-specific tumor antigen selection for vaccination," Immunol. Rev. 188: 164-176.
Rammensee et al., Immunogenentics, 50 (1999), 213-219.
Rao (1994). "Epitope-based vaccines: One step at a time," Proc. Indian natn. Sci. Acad. B60: 419-424.
Ressing, M. et al. "Human CTL epitopes encoded by human papillomavirus types 16E6 . . . " J. Immunol. 154:5934-5943, 1995.
Saenz-Badillos et al. (2001). "RNA as a tumor vaccine: a review of the literature," Exp Dermatol. 10(3):143-54.
Segal et al. (2008). "Epitope landscape in breast and colorectal cancer," Cancer Res. 68: 889-892.
Sensi and Aanichini, Unique Tumor Antigens: Evidence for Immune Control of Genome Integrity and Immunogenic Targets for T cell-mediated Patient-Specific Immunotherapy, Clin. Cancer Res. 2006:12(17), 5023.
Sette, A. et al. "Peptide Binding to the Most Frequent HLA-A Class I Alleles Measured by Quantitative Molecular Binding Assays" Mol Immunol. 31: 813-822, 1994.
Sette, A. et al. "The Relationship Between Class I Binding Affinity and Immunogenicity of Potential Cytotoxic T cell Epitopes " J Immunol. 153: 5586-5592, 1994.
Shah et al. (2009). "Mutation of FOXL2 in granulosa-cell tumors of the ovary," N. Eng. J. Med. 360: 2719-2729.
Sjöblom et al. (2006). "The consensus coding sequences of human breast and colorectal cancers," Science 314: 268-274.
Stephens et al. (2005). "A screen of the complete protein kinase gene family identifies diverse patterns of somatic mutations in human breast cancer," Nature Genetics, 37: 590-592.
Thomson et al., J. Virology (1998), 72(3):2246-2252.

(56) References Cited

OTHER PUBLICATIONS

Toes et al. (1997). "Protective anti-tumor immunity induced by vaccination with recombinant adenoviruses encoding multiple tumor-associated cytotoxic T lymphocyte epitopes in a string-of-beads fashion," Proc. Natl. Acad. Sci. USA 94: 14660-14665.
UniprotKB, "Print-outs from the UniProtKB database concerning the CEP170, PARVA and FLT3 genes".
van der Bruggen et al. (1991). "A gene encoding an antigen recognized by cytolytic T lymphocytes on a human melanoma," Science 254:1643-1647.
Van Laere AS, Nguyen M, Braunschweig M. et al. A regulatory mutation in IGF2 causes a major QTL effect on muscle growth in the pig. Nature. 2003;425(6960):832-836.
Weinschenk et al. (2002). "Integrated functional genomics approach for the design of patient-individual antitumor vaccines," Cancer Res 62: 5818-5827.
Wolff et al. (1990). "Direct gene transfer into mouse muscle in vivo," Science 247: 1465-1468.
Wood et al. (2007). "The genomic landscapes of human breast and colorectal cancers," Science 318: 1108-1113.
Wortzel et al. (1983). "Multiple tumour-specific antigens expressed on a single tumour cell," Nature 304: 165-167.
Zhou et al., Hum. Gene Ther., 10(16):2719-24, 1999.
U.S. Appl. No. 61/334,866, filed May 14, 2010.
Russian Office Action issued in related Russian Application No. 2015153007, dated Mar. 28, 2018.
Castle et al., "Exploiting the Mutanome for Tumor Vaccination," Cancer Reserach; 72(5), Mar. 1, 2012, pp. 1081-1091.
UniProtKB—P36888 (FLT3_HUMAN), last sequence update: Aug. 21, 2007.
UniProtKB—Q9NVD7 (PARVA_HUMAN), last sequence update: Oct. 1, 2000.
UniProtKB—Q5SW79 (CE170_HUMAN), last sequence update: Dec. 21, 2004.
Dolgin, "The Billion-Dollar Biotech," Nature, vol. 522, pp. 26-28, Jun. 4, 2015.
Chinese Office Action issued in related Chinese Application No. 201480026604.1, dated Jun. 13, 2018.
Office Action issued in Singaporean Application No. 11201508816R, dated Jan. 25, 2018.
Khalili et al., "In silico prediction of tumor antigens derived from functional missense mutations of the cancer gene census," OncoImmunology, Nov. 30, 2012, vol. 1, No. 8, pp. 1281-1289.
De Groot A.S. and Moise L., Prediction of immunogenicity for therapeutic proteins: state of the art. Curr Opin Drug Discov Devel., May 10, 2007, vol. 10, No. 03, pp. 332-340.
May 20, 2019—(CN) Office Action—App. 201480026604.1—Eng Tran.
Nov. 21, 2018—(EP) Office Action—App. 14722117.0.
Nielsen et al., "NetMHCpan, a Method for Quantitative Predictions of Peptide Binding to Any HLA-A and -B Locus Protein of Known Sequence," PLoS ONE, Issue 8, Aug. 2007.
Office Action issued in related Russian Application No. 2015153007, dated Nov. 2, 2017.
Wan et al., "Large-Scale Molecular Dynamics Simulations of HLA-A *0201 Complexed with a Tumor-Specific Antigenic Peptide: Can the a3 and B2m Domains be Neglected?", Journal of Computational Chemistry, vol. 25, No. 15, 2004.

* cited by examiner

Fig. 10

| Sample[1] | Class | Gene | HLA allele | Anchor positions[2] | Epitope (WT)[3] | Epitope (MUT)[3] | $M_{mut}$ | $M_{wt}$ | Achnor position mutation | Immunogenic |
|---|---|---|---|---|---|---|---|---|---|---|
| MZ7-MEL | class II (H$_B$UH$_C$) | SNRP116 | HLA-A*03 | 1 2 3 4 5 6 7 8 9 | kiL DAV V AQE | kiL DAV V AQK | 0.15 | 10.20 | yes | yes |
| MZ7-MEL | class II (H$_B$UH$_C$) | ZNF335 | HLA-B*38:01 | 1 2 3 4 5 6 7 8 9 | QH SAAPGPP | QH SAAPGPL | 0.20 | 18.35 | yes | unknown |
| Zorn et al. | class II (H$_B$UH$_C$) | MYO1B | HLA-A*03 | 1 2 3 4 5 6 7 8 9 | EINKNPKYK | KINKNPKYK | 0.25 | 2.25 | no | yes |
| Graf et al. | class II (H$_B$UH$_C$) | FLT3 | HLA-A*01 | 1 2 3 4 5 6 7 8 9 | YVDFREYEYD | YVDFREYEYY | 0.20 | 10.95 | yes | yes |
| Robbins et al. | class II (H$_B$UH$_C$) | CTNNB1 | HLA-A24 | 1 2 3 4 5 6 7 8 9 | sY LDSGIHS | sY LDSGIHF | 0.38 | 10.58 | yes | yes |

[1] See Table 3
[2] Anchors (bold) and auxiliary anchors (underline) positions are indicated
[3] Conserved anchor (bold) and auxiliary anchor (underline) residues for the given HLA type and epitope are printed in large fonts. Mutated residue is highlighted in red.

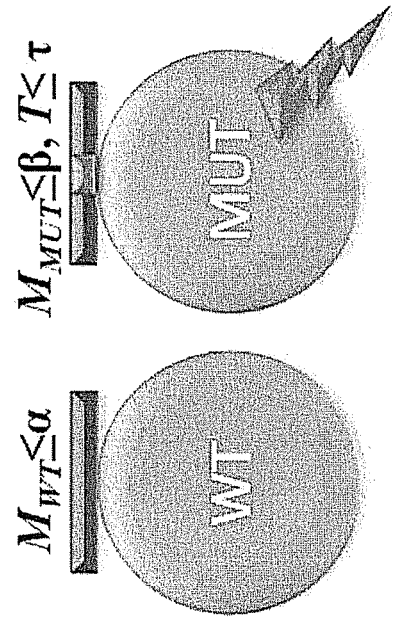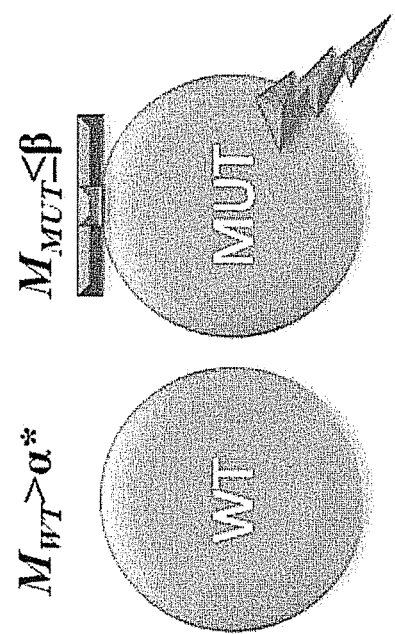
Fig. 11

PREDICTING IMMUNOGENICITY OF T CELL EPITOPES

TECHNICAL FIELD OF THE INVENTION

The present invention relates to methods for predicting T cell epitopes. In particular, the present invention relates to methods for predicting whether modifications in peptides or polypeptides such as tumor-associated neoantigens are immunogenic or not. The methods of the invention are useful, in particular, for the provision of vaccines which are specific for a patient's tumor and, thus, in the context of personalized cancer vaccines.

BACKGROUND OF THE INVENTION

Personalized cancer vaccines are therapeutic vaccines custom tailored to target tumor-specific mutations that are unique to a given patient. Such a treatment offers great hope for cancer patients as it does not harm healthy cells and has the potential to provide life-long remission. Yet not every mutation expressed by the tumor can be used as a target for a vaccine. In fact, most cancer somatic mutations will not lead to an immune response when vaccinated against (J. C. Castle et al., Exploiting the mutanome for tumor vaccination. Cancer Research 72, 1081 (2012)). Since tumors can encode as many as 100,000 somatic mutations (M. R. Stratton, Science Signalling 331, 1553 (2011)) whereas vaccines target only a handful of epitopes, it is apparent that a critical goal of cancer immunotherapy is to identify which mutations are likely to be immunogenic.

From a biological perspective, in order for a somatic mutation to generate an immune response several criteria need to be satisfied: the allele containing the mutation should be expressed by the cell, the mutation should be in a protein coding region and nonsynonymous, the translated protein should be cleaved by the proteasome and an epitope containing the mutation should be presented by the MHC complex, the presented epitope should be recognized by a T cell receptor (TCR) and, finally, the TCR-pMHC complex should launch a signaling cascade that activates the T cell (S. Whelan, N. Goldman, Molecular biology and evolution 18, 691 (2001)). Thus far no algorithm has been put forth that is capable of predicting with a high degree of certainty which mutations are likely to fulfill all these criteria. In the present report we consider several factors that may contribute to immunogenicity, compare these factors against experimental data and propose a simple model for identifying immunogenic mutations.

MHC BINDING PREDICTION: STATE IF THE ART

Over 20 years ago, it was established, that there are positions in a MHC binding peptide, which contribute more to the binding capability then others (e.g., (A. Sette et al., Proceedings of the National Academy of Sciences 86, 3296 (1989))). The identification and description of those anchor positions enabled finding patterns of MHC binding peptides and thus were the basis for developing methods for predicting. In recent years significant developments in the field of in silico models of the Antigen Processing Machinery were achieved. The two pioneering approaches, which were developed in the late 1990's, BIMAS (K. C. Parker, M. A. Bednarek, J. E. Coligan, The Journal of Immunology 152, 163 (1994)) and SYFPEITHI (H.-G. Rammensee, J. Bachmann, N. P. N. Emmerich, O. A. Bachor, S. Stevanović, Immunogenetics 50, 213 (1999)), were based on the knowledge of anchor positions and on the derived allele-specific motifs. As more and more experimental MHC peptide-binding data became available, more tools have been developed using a wide variety of statistical and computational techniques (see FIG. 1 for an overview). The so-called matrix-based methods use position-specific scoring matrices to determine if a peptide sequence matches the binding motif of particular MHC allele. Another class of MHC binding prediction methods use machine learning techniques, such as Artificial Neural Networks or Support Vector Machines (see FIG. 1). The performance of these algorithms strongly depends on quantity and quality of the available training dataset for each allele model (e.g. "HLA-A*02:01", "H2-Db" etc.) to "learn" underlying patterns /features, which have prediction capability for binding. Recently, structure-based methods are emerging, which circumvent the bottleneck of having a large training set, as they solely rely on peptide-MHC crystal structures and scoring functions (e.g. different energy functions) to predict peptide-MHC interactions by, e.g. energy minimization (see FIG. 1). However, the accuracy of those approaches is still far behind the sequence-based methods. Benchmarking studies shows that the artificial neural network based tool NetMHC (C. Lundegaard et al., Nucleic Acids Research 36, W509 (2008)) and the matrix based algorithm SMM (B. Peters, A. Sette, BMC bioinformatics 6, 132 (2005)) perform best on the tested evaluation data (B. Peters, A. Sette, BMC bioinformatics 6, 132 (2005); H. H. Lin, S. Ray, S. Tongchusak, E. L. Reinherz, V. Brusic, BMC immunology 9, 8 (2008)). Both approaches are integrated in the so-called IEDB consensus methods, available at the Immune Epitope Database (Y. Kim et al., Nucleic Acids Research 40, W525 (2012)). Modeling interactions of peptide-MHC II binding is far more complex than for MHC I, as MHC II molecules possess a binding groove with open ends at either side, allowing binding of peptides of different lengths. Whereas peptides binding to MHC I is restricted to mainly 8-12 amino acids, this length can differ for MHC II peptides dramatically (9-30 amino acids). A recent benchmarking study shows, that the available MHC II predictions methods offer a limited accuracy compared to MHC I prediction (H. H. Lin, S. Ray, S. Tongchusak, E. L. Reinherz, V. Brusic, BMC immunology 9, 8 (2008)).

The first large-scale and systematic use of those algorithms to find T cell epitopes was undertaken by Moutaftsi et al. (M. Moutaftsi et al., Nature Biotechnology 24, 817 (2006)), where different tools were combined to predict possible vaccine candidates of vaccinia virus infected C57BL76 mice, extracted spleenocytes and measured CD8+ T cell responses against the top 1% of the predicted peptides. They identified 49 (out of 2256) peptides, that induced a T cell response. Since then many studies have been published using various MHC binding prediction tools to search for T cell epitopes as candidates for a vaccine, mainly for pathogens, e.g., *Leishmania major* (C. Herrera-Najera, R. Piña-Aguilar, F. Xacur-Garcia, M. J. Ramirez-Sierra, E. Dumonteil, Proteomics 9, 1293 (2009)). However, to use solely MHC I binding prediction tools for prediction of immunogenicity is misleading, as those tools are trained to predict whether a given peptide has the potential to bind to a given MHC allele. The rationale of using MHC binding predictions for predicting immunogenicity is the assumption that peptides binding with high affinity a respective MHC allele is more likely to be immunogenic (A. Sette et al., The Journal of Immunology 153, 5586 (1994)). However, there are numerous studies indicating, that also low MHC binding affinity can result in high immunogenicity (M. C. Feltkamp, M. P. Vierboom, W. M. Kast, C. J. Melief, Molecular Immunology 31, 1391 (1994)) and that peptide-MHC stability might be a better predictor for immunogenicity than peptide affinity (M. Harndahl et al., European Journal of Immunology 42, 1405 (2012)). For that reason, immunogenicity prediction was not very accurate so far, which is mirrored in the low success rates for predicting immunogenicity. Nevertheless, peptide binding is a necessary but not sufficient condition of T cell epitope recognition, and efficient prediction can dramatically reduce the number of peptides to be tested experimentally.

It is clear that the development of a model that predicts immunogenicity needs also to take into account the recognition of the T cell receptor (TCR) as well as central tolerance, i.e., the negative and positive selection of T cells during development in the thymus.

There is a need for a predictive model, which is capable to model all the aspects mentioned above to accurately predict immunogenicity of an epitope, rather than only binding.

DESCRIPTION OF INVENTION

SUMMARY OF THE INVENTION

In one aspect, the present invention relates to a method for predicting immunogenic amino acid modifications, the method comprising the steps:

a) ascertaining a score for binding of a modified peptide to one or more MHC molecules, and b) ascertaining a score for binding of the non-modified peptide to one or more MHC molecules, and/or c) ascertaining a score for binding of the modified peptide when present in a MHC-peptide complex to one or more T cell receptors.

In one embodiment, the modified peptide comprises a fragment of a modified protein, said fragment comprising the modification(s) present in the protein. In one embodiment, the non-modified peptide or protein has the germline amino acid at the position(s) corresponding to the position(s) of the modification(s) in the modified peptide or protein.

In one embodiment, the non-modified peptide or protein and modified peptide or protein are identical but for the modification(s). Preferably, the non-modified peptide or protein and modified peptide or protein have the same length/or and sequence (except for the modification(s)).

In one embodiment, the non-modified peptide and modified peptide are 8 to 15, preferably 8 to 12 amino acids in length.

In one embodiment, the one or more MHC molecules comprise different MHC molecule types, in particular different MHC alleles. In one embodiment, the one or more MHC molecules are MHC class I molecules and/or MHC class II molecules. In one embodiment, the one or more MHC molecules comprise a set of MHC alleles such as a set of MHC alleles of an individual or a subset thereof.

In one embodiment, the score for binding to one or more MHC molecules is ascertained by a process comprising a sequence comparison with a database of MHC-binding motifs.

In one embodiment, step a) comprises ascertaining whether said score satisfies a pre-determined threshold for binding to one or more MHC molecules and/or step b) comprises ascertaining whether said score satisfies a pre-determined threshold for binding to one or more MHC molecules. In one embodiment, the threshold applied in step a) is different to the threshold applied in step b). In one embodiment, the pre-determined threshold for binding to one or more MHC molecules reflects a probability for binding to one or more MHC molecules.

In one embodiment, the one or more T cell receptors comprise a set of T cell receptors such a set of T cell receptors of an individual or a subset thereof. In one embodiment, step c) comprises assuming that said set of T cell receptors does not include T cell receptors which bind to the non-modified peptide when present in a MHC-peptide complex and/or does not include T cell receptors which bind to the non-modified peptide when present in a MHC-peptide complex with high affinity.

In one embodiment, step c) comprises ascertaining a score for the chemical and physical similarities between the non-modified and modified amino acids. In one embodiment, step c) comprises ascertaining whether said score satisfies a pre-determined threshold for the chemical and physical similarities between amino acids. In one embodiment, said pre-determined threshold for the chemical and physical similarities between amino acids reflects a probability for amino acids being chemically and physically similar. In one embodiment, the score for the chemical and physical similarities is ascertained on the basis of the probability of amino acids being interchanged in nature. In one embodiment, the more frequently amino acids are interchanged in nature the more similar the amino acids are considered and vice versa. In one embodiment, the chemical and physical similarities are determined using evolutionary based log-odds matrices, In one embodiment, if the non-modified peptide has a score for binding to one or more MHC molecules satisfying a threshold indicating binding to one or more MHC molecules and the modified peptide has a score for binding to one or more MHC molecules satisfying a threshold indicating binding to one or more MHC molecules, the modification or modified peptide is predicted as immunogenic if the non-modified and modified amino acids have a score for the chemical and physical similarities satisfying a threshold indicating chemical and physical dissimilarity.

In one embodiment, if the non-modified peptide binds to one or more MHC molecules or has a probability for binding to one or more MHC molecules and the modified peptide binds to one or more MHC molecules or has a probability for binding to one or more MHC molecules, the modification or modified peptide is predicted as immunogenic if the non-modified and modified amino acids are chemically and physically dissimilar or have a probability of being chemically and physically dissimilar.

In one embodiment, the modification is not in an anchor position for binding to one or more MHC molecules.

In one embodiment, if the non-modified peptide has a score for binding to one or more MHC molecules satisfying a threshold indicating no binding to one or more MHC molecules and the modified peptide has a score for binding to one or more MHC molecules satisfying a threshold indicating binding to one or more MHC molecules, the modification or modified peptide is predicted as immunogenic.

In one embodiment, if the non-modified peptide does not bind to one or more MHC molecules or has a probability for not binding to one or more MHC molecules and the modified peptide binds to one or more MHC molecules or has a probability for binding to one or more MHC molecules, the modification or modified peptide is predicted as immunogenic.

In one embodiment, the modification is in an anchor position for binding to one or more MHC molecules.

In one embodiment, the method of the invention comprises performing step a) on two or more different modified peptides, said two or more different modified peptides comprising the same modification(s). In one embodiment, the two or more different modified peptides comprising the same modification(s) comprise different fragments of a modified protein, said different fragments comprising the same modification(s) present in the protein. In one embodiment, the two or more different modified peptides comprising the same modification(s) comprise all potential MHC binding fragments of a modified protein, said fragments comprising the same modification(s) present in the protein. In one embodiment, the method of the invention further comprises selecting (the) modified peptide(s) from the two or more different modified peptides comprising the same modification(s) having a probability or having the highest probability for binding to one or more MHC molecules. In one embodiment, the two or more different modified peptides comprising the same modification(s) differ in length and/or position of the modification(s).

In one embodiment, the method of the invention comprises performing step a) and optionally one or both of steps b) and c) on two or more different modified peptides. In one embodiment, said two or more different modified peptides comprise the same modification(s) and/or comprise different modifications. In one embodiment, the different modifications are present in the same and/or in different proteins. The set of two or more different modified peptides used in step a) and optionally one or both of steps b) and c) may be the same or different. In one embodiment, the set of two or more different modified peptides used in step b) and/or step c) is a subset of the set of two or more different modified peptides used in step a). Preferably, said subset includes the peptide(s) scoring best in step a).

In one embodiment, the method of the invention comprises comparing the scores of two or more of said different modified peptides. In one embodiment, the method of the invention comprises ranking two or more of said different modified peptides. In one embodiment, a score for binding of the modified peptide to one or more MHC molecules is weighted higher than a score for binding of the modified peptide when present in a MHC-peptide complex to one or more T cell receptors, preferably a score for the chemical and physical similarities between the non-modified and modified amino acids and a score for binding of the modified peptide when present in a MHC-peptide complex to one or more T cell receptors, preferably a score for the chemical and physical similarities between the non-modified and modified amino acids is weighted higher than a score for binding of the non-modified peptide to one or more MHC molecules.

In one embodiment, the method of the invention further comprises identifying non-synonymous mutations in one or more protein-coding regions.

In one embodiment, modifications are identified according to the invention by partially or completely sequencing the genome or transcriptome of one or more cells such as one or more cancer cells and optionally one or more non-cancerous cells and identifying mutations in one or more protein-coding regions.

In one embodiment, said mutations are somatic mutations. In one embodiment, said mutations are cancer mutations.

In one embodiment, the method of the invention is used in the manufacture of a vaccine. In one embodiment, the vaccine is derived from (a) modification(s) or (a) modified peptide(s) predicted as immunogenic by the methods of the invention.

In a further aspect, the present invention provides a method for providing a vaccine comprising the step:
identifying (a) modification(s) or (a) modified peptide(s) predicted as immunogenic by the methods of the invention.

In one embodiment, the method further comprises the step:
providing a vaccine comprising a peptide or polypeptide comprising the modification(s) or modified peptide(s) predicted as immunogenic, or a nucleic acid encoding the peptide or polypeptide.

In a further aspect, the present invention provides a vaccine which is obtainable using the methods according to the invention. Preferred embodiments of such vaccines are described herein.

A vaccine provided according to the invention may comprise a pharmaceutically acceptable carrier and may optionally comprise one or more adjuvants, stabilizers etc. The vaccine may in the form of a therapeutic or prophylactic vaccine.

Another aspect relates to a method for inducing an immune response in a patient, comprising administering to the patient a vaccine provided according to the invention.

Another aspect relates to a method of treating a cancer patient comprising the steps:
(a) providing a vaccine by the methods according to the invention; and
(b) administering said vaccine to the patient.

Another aspect relates to a method of treating a cancer patient comprising administering the vaccine according to the invention to the patient.

In further aspects, the invention provides the vaccines described herein for use in the methods of treatment described herein, in particular for use in treating or preventing cancer.

The treatments of cancer described herein can be combined with surgical resection and/or radiation and/or traditional chemotherapy.

Other features and advantages of the instant invention will be apparent from the following detailed description and claims.

DETAILED DESCRIPTION OF THE INVENTION

Although the present invention is described in detail below, it is to be understood that this invention is not limited to the particular methodologies, protocols and reagents described herein as these may vary. It is also to be understood that the terminology used herein is for the purpose of describing particular embodiments only, and is not intended to limit the scope of the present invention which will be limited only by the appended claims. Unless defined otherwise, all technical and scientific terms used herein have the same meanings as commonly understood by one of ordinary skill in the art.

In the following, the elements of the present invention will be described. These elements are listed with specific embodiments, however, it should be understood that they may be combined in any manner and in any number to create additional embodiments. The variously described examples and preferred embodiments should not be construed to limit the present invention to only the explicitly described embodiments. This description should be understood to support and encompass embodiments which combine the explicitly described embodiments with any number of the disclosed and/or preferred elements. Furthermore, any permutations and combinations of all described elements in this application should be considered disclosed by the description of the present application unless the context indicates otherwise.

Preferably, the terms used herein are defined as described in "A multilingual glossary of biotechnological terms: (IUPAC Recommendations)", H. G. W. Leuenberger, B. Nagel, and H. Kölbl, Eds., (1995) *Helvetica Chimica Acta*, CH-4010 Basel, Switzerland.

The practice of the present invention will employ, unless otherwise indicated, conventional methods of biochemistry, cell biology, immunology, and recombinant DNA techniques which are explained in the literature in the field (cf., e.g., *Molecular Cloning: A Laboratory Manual*, $2^{nd}$ Edition, J. Sambrook et al. eds., Cold Spring Harbor Laboratory Press, Cold Spring Harbor 1989).

Throughout this specification and the claims which follow, unless the context requires otherwise, the word "comprise", and variations such as "comprises" and "comprising", will be understood to imply the inclusion of a stated member, integer or step or group of members, integers or steps but not the exclusion of any other member, integer or step or group of members, integers or steps although in some embodiments such other member, integer or step or group of members, integers or steps may be excluded, i.e. the subject-matter consists in the inclusion of a stated member, integer or step or group of members, integers or steps. The terms "a" and "an" and "the" and similar reference used in the context of describing the invention (especially in the context of the claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein.

All methods described herein can be performed in any suitable order unless otherwise indicated herein or otherwise clearly contradicted by context. The use of any and all examples, or exemplary language (e.g., "such as"), provided herein is intended merely to better illustrate the invention and does not pose a limitation on the scope of the invention otherwise claimed. No language in the specification should be construed as indicating any non-claimed element essential to the practice of the invention.

Several documents are cited throughout the text of this specification. Each of the documents cited herein (including all patents, patent applications, scientific publications, manufacturer's specifications, instructions, etc.), whether supra or infra, are hereby incorporated by reference in their entirety. Nothing herein is to be construed as an admission that the invention is not entitled to antedate such disclosure by virtue of prior invention.

According to the present invention, the term "peptide" refers to substances comprising two or more, preferably 3 or more, preferably 4 or more, preferably 6 or more, preferably 8 or more, preferably 10 or more, preferably 13 or more, preferably 16 more, preferably 21 or more and up to preferably 8, 10, 20, 30, 40 or 50, in particular 100 amino acids joined covalently by peptide bonds. The term "polypeptide" or "protein" refers to large peptides, preferably to peptides with more than 100 amino acid residues, but in general the terms "peptide", "polypeptide" and "protein" are synonyms and are used interchangeably herein.

According to the invention, the term "modification" with respect to peptides, polypeptides or proteins relates to a sequence change in a peptide, polypeptide or protein compared to a parental sequence such as the sequence of a wildtype peptide, polypeptide or protein. The term includes amino acid insertion variants, amino acid addition variants, amino acid deletion variants and amino acid substitution variants, preferably amino acid substitution variants. All these sequence changes according to the invention may potentially create new epitopes.

Amino acid insertion variants comprise insertions of single or two or more amino acids in a particular amino acid sequence.

Amino acid addition variants comprise amino- and/or carboxy-terminal fusions of one or more amino acids, such as 1, 2, 3, 4 or 5, or more amino acids.

Amino acid deletion variants are characterized by the removal of one or more amino acids from the sequence, such as by removal of 1, 2, 3, 4 or 5, or more amino acids.

Amino acid substitution variants are characterized by at least one residue in the sequence being removed and another residue being inserted in its place.

According to the invention, a modification or modified peptide used for testing in the methods of the invention may be derived from a protein comprising a modification.

The term "derived" means according to the invention that a particular entity, in particular a particular peptide sequence, is present in the object from which it is derived. In the case of amino acid sequences, especially particular sequence regions, "derived" in particular means that the relevant amino acid sequence is derived from an amino acid sequence in which it is present.

A protein comprising a modification from which a modification or modified peptide used for testing in the methods of the invention may be derived may be a neoantigen.

According to the invention, the term "neoantigen" relates to a peptide or protein including one or more amino acid modifications compared to the parental peptide or protein. For example, the neoantigen may be a tumor-associated neoantigen, wherein the term "tumor-associated neoantigen" includes a peptide or protein including amino acid modifications due to tumor-specific utations.

According to the invention, the term "tumor-specific mutation" or "cancer-specific mutation" relates to a somatic mutation that is present in the nucleic acid of a tumor or cancer cell but absent in the nucleic acid of a corresponding normal, i.e. non-tumorous or non-cancerous, cell.

The terms "tumor-specific mutation" and "tumor mutation" and the terms "cancer-specific mutation" and "cancer mutation" are used interchangeably herein.

The term "immune response" refers to an integrated bodily response to a target such as an antigen and preferably refers to a cellular immune response or a cellular as well as a humoral immune response. The immune response may be protective/preventive/prophylactic and/or therapeutic.

"Inducing an immune response" may mean that there was no immune response before induction, but it may also mean that there was a certain level of immune response before induction and after induction said immune response is enhanced. Thus, "inducing an immune response" also includes "enhancing an immune response". Preferably, after inducing an immune response in a subject, said subject is protected from developing a disease such as a cancer disease or the disease condition is ameliorated by inducing an immune response. For example, an immune response against a tumor-expressed antigen may be induced in a patient having a cancer disease or in a subject being at risk of developing a cancer disease. Inducing an immune response in this case may mean that the disease condition of the subject is ameliorated, that the subject does not develop metastases, or that the subject being at risk of developing a cancer disease does not develop a cancer disease.

The terms "cellular immune response" and "cellular response" or similar terms refer to an immune response directed to cells characterized by presentation of an antigen with class I or class II MHC involving T cells or T-lymphocytes which act as either "helpers" or "killers". The helper T cells (also termed CD4+ T cells) play a central role by regulating the immune response and the killer cells (also termed cytotoxic T cells, cytolytic T cells, CD8+ T cells or CTLs) kill diseased cells such as cancer cells, preventing the production of more diseased cells. In preferred embodiments, the present invention involves the stimulation of an anti-tumor CTL response against tumor cells expressing one or more tumor-expressed antigens and preferably presenting such tumor-expressed antigens with class I MHC.

An "antigen" according to the invention covers any substance, preferably a peptide or protein, that is a target of and/or induces an immune response such as a specific reaction with antibodies or T-lymphocytes (T cells). Preferably, an antigen comprises at least one epitope such as a T cell epitope. Preferably, an antigen in the context of the present invention is a molecule which, optionally after processing, induces an immune reaction, which is preferably specific for the antigen (including cells expressing the antigen). The antigen or a T cell epitope thereof is preferably presented by a cell, preferably by an antigen presenting cell which includes a diseased cell, in particular a cancer cell, in the context of MHC molecules, which results in an immune response against the antigen (including cells expressing the antigen).

In one embodiment, an antigen is a tumor antigen (also termed tumor-expressed antigen herein), i.e., a part of a tumor cell such as a protein or peptide expressed in a tumor cell which may be derived from the cytoplasm, the cell surface or the cell nucleus, in particular those which primarily occur intracellularly or as surface antigens of tumor cells. For example, tumor antigens include the carcinoembryonal antigen, α1-fetoprotein, isoferritin, and fetal sulphoglycoprotein, α2-H-ferroprotein and γ-fetoprotein. According to the present invention, a tumor antigen preferably comprises any antigen which is expressed in and optionally characteristic with respect to type and/or expression level for tumors or cancers as well as for tumor or cancer cells, i.e. a tumor-associated antigen. In one embodiment, the term "tumor-associated antigen" relates to proteins that are under normal conditions specifically expressed in a limited number of tissues and/or organs or in specific developmental stages, for example, the tumor-associated antigens may be under normal conditions specifically expressed in stomach tissue, preferably in the gastric mucosa, in reproductive organs, e.g., in testis, in trophoblastic tissue, e.g., in placenta, or in germ line cells, and are expressed or aberrantly expressed in one or more tumor or cancer tissues. In this context, "a limited number" preferably means not more than 3, more preferably not more than 2. The tumor antigens in the context of the present invention include, for example, differentiation antigens, preferably cell type specific differentiation antigens, i.e., proteins that are under normal conditions specifically expressed in a certain cell type at a certain differentiation stage, cancer/testis antigens, i.e., proteins that are under normal conditions specifically expressed in testis and sometimes in placenta, and germ line specific antigens. Preferably, the tumor antigen or the aberrant expression of the tumor antigen identifies cancer cells. In the context of the present invention, the tumor antigen that is expressed by a cancer cell in a subject, e.g., a patient suffering from a cancer disease, is preferably a self-protein in said subject. In preferred embodiments, the tumor antigen in the context of the present invention is expressed under normal conditions specifically in a tissue or organ that is non-essential, i.e., tissues or organs which when damaged by the immune system do not lead to death of the subject, or in organs or structures of the body which are not or only hardly accessible by the immune system.

According to the invention, the terms "tumor antigen", "tumor-expressed antigen", "cancer antigen" and "cancer-expressed antigen" are equivalents and are used interchangeably herein.

The term "immunogenicity" relates to the relative effectivity to induce an immune response that is preferably associated with therapeutic treatments, such as treatments against cancers. As used herein, the term "immunogenic" relates to the property of having immunogenicity. For example, the term "immunogenic modification" when used in the context of a peptide, polypeptide or protein relates to the effectivity of said peptide, polypeptide or protein to induce an immune response that is caused by and/or directed against said modification. Preferably, the non-modified peptide, polypeptide or protein does not induce an immune response, induces a different immune response or induces a different level, preferably a lower level, of immune response.

The terms "major histocompatibility complex" and the abbreviation "MHC" include MHC class I and MHC class II molecules and relate to a complex of genes which occurs in all vertebrates. MHC proteins or molecules are important for signaling between lymphocytes and antigen presenting cells or diseased cells in immune reactions, wherein the MHC proteins or molecules bind peptides and present them for recognition by T cell receptors. The proteins encoded by the MHC are expressed on the surface of cells, and display both self antigens (peptide fragments from the cell itself) and non-self antigens (e.g., fragments of invading microorganisms) to a T cell.

The MHC region is divided into three subgroups, class I, class II, and class III. MHC class I proteins contain an α-chain and β2-microglobulin (not part of the MHC encoded by chromosome 15). They present antigen fragments to cytotoxic T cells. On most immune system cells, specifically on antigen-presenting cells, MHC class II proteins contain α- and β-chains and they present antigen fragments to T-helper cells. MHC class III region encodes for other immune components, such as complement components and some that encode cytokines.

The MHC is both polygenic (there are several MHC class I and MHC class II genes) and polymorphic (there are multiple alleles of each gene).

As used herein, the term "haplotype" refers to the HLA alleles found on one chromosome and the proteins encoded thereby. Haplotype may also refer to the allele present at any one locus within the MHC. Each class of MHC is represented by several loci: e.g., HLA-A (Human Leukocyte Antigen-A), HLA-B, HLA-C, HLA-E, HLA-F, HLA-G, HLA-H, HLA-J, HLA-K, HLA-L, HLA-P and HLA-V for class I and HLA-DRA, HLA-DRB1-9, HLA-, HLA-DQA1, HLA-DQB1, HLA-DPA1 , HLA-DPB1, HLA-DMA, HLA-DMB, HLA-DOA, and HLA-DOB for class II. The terms "HLA allele" and "MHC allele" are used interchangeably herein.

The MHCs exhibit extreme polymorphism: within the human population there are, at each genetic locus, a great number of haplotypes comprising distinct alleles. Different polymorphic MHC alleles, of both class I and class II, have different peptide specificities: each allele encodes proteins that bind peptides exhibiting particular sequence patterns.

In one preferred embodiment of all aspects of the invention an MHC molecule is an HLA molecule.

In the context of the present invention, the term "MHC binding peptide" includes MHC class I and/or class II binding peptides or peptides that can be processed to produce MHC class I and/or class II binding peptides. In the case of class I MHC/peptide complexes, the binding peptides are typically 8-12, preferably 8-10 amino acids long although longer or shorter peptides may be effective. In the case of class II MHC/peptide complexes, the binding peptides are typically 9-30, preferably 10-25 amino acids long and are in particular 13-18 amino acids long, whereas longer and shorter peptides may be effective.

If a peptide is to be presented directly, i.e., without processing, in particular without cleavage, it has a length which is suitable for binding to an MHC molecule, in particular a class I MHC molecule, and preferably is 7-30 amino acids in length such as 7-20 amino acids in length, more preferably 7-12 amino acids in length, more preferably 8-11 amino acids in length, in particular 9 or 10 amino acids in length.

If a peptide is part of a larger entity comprising additional sequences, e.g. of a vaccine sequence or polypeptide, and is to be presented following processing, in particular following cleavage, the peptide produced by processing has a length which is suitable for binding to an MHC molecule, in particular a class I MHC molecule, and preferably is 7-30 amino acids in length such as 7-20 amino acids in length, more preferably 7-12 amino acids in length, more preferably 8-11 amino acids in length, in particular 9 or 10 amino acids in length. Preferably, the sequence of the peptide which is to be presented following processing is derived from the amino acid sequence of an antigen or polypeptide used for vaccination, i.e., its sequence substantially corresponds and is preferably completely identical to a fragment of the antigen or polypeptide.

Thus, an MHC binding peptide in one embodiment comprises a sequence which substantially corresponds and is preferably completely identical to a fragment of an antigen.

The term "epitope" refers to an antigenic determinant in a molecule such as an antigen, i.e., to a part in or fragment of the molecule that is recognized by the immune system, for example, that is recognized by a T cell, in particular when presented in the context of MHC molecules. An epitope of a protein such as a tumor antigen preferably comprises a continuous or discontinuous portion of said protein and is preferably between 5 and 100, preferably between 5 and 50, more preferably between 8 and 30, most preferably between 10 and 25 amino acids in length, for example, the epitope may be preferably 9, 10, 11, 12, 13, 14, 15, 16, 17, 18, 19, 20, 21, 22, 23, 24, or 25 amino acids in length. It is particularly preferred that the epitope in the context of the present invention is a T cell epitope.

According to the invention an epitope may bind to MHC molecules such as MHC molecules on the surface of a cell and thus, may be a "MHC binding peptide".

As used herein the term "neo-epitope" refers to an epitope that is not present in a reference such as a normal non-cancerous or germline cell but is found in cancer cells. This includes, in particular, situations wherein in a normal non-cancerous or germline cell a corresponding epitope is found, however, due to one or more mutations in a cancer cell the sequence of the epitope is changed so as to result in the neo-epitope.

As used herein, the term "T cell epitope" refers to a peptide which binds to a MHC molecule in a configuration recognized by a T cell receptor. Typically, T cell epitopes are presented on the surface of an antigen-presenting cell.

As used herein, the term "predicting T cell epitopes" refers to a prediction whether a peptide will bind to a MHC molecule and will be recognized by a T cell receptor. The term "predicting T cell epitopes" is essentially synonymous with the phrase "predicting whether a peptide is immunogenic".

According to the invention, a T cell epitope may be present in a vaccine as a part of a larger entity such as a vaccine sequence and/or a polypeptide comprising more than one T cell epitope. The presented peptide or T cell epitope is produced following suitable processing.

T cell epitopes may be modified at one or more residues that are not essential for TCR recognition or for binding to MHC. Such modified T cell epitopes may be considered immunologically equivalent.

Preferably a T cell epitope when presented by MHC and recognized by a T cell receptor is able to induce in the presence of appropriate co-stimulatory signals, clonal expansion of the T cell carrying the T cell receptor specifically recognizing the peptide/MHC-complex.

Preferably, a T cell epitope comprises an amino acid sequence substantially corresponding to the amino acid sequence of a fragment of an antigen. Preferably, said fragment of an antigen is an MHC class I and/or class II presented peptide.

A T cell epitope according to the invention preferably relates to a portion or fragment of an antigen which is capable of stimulating an immune response, preferably a cellular response against the antigen or cells characterized by expression of the antigen and preferably by presentation of the antigen such as diseased cells, in particular cancer cells. Preferably, a T cell epitope is capable of stimulating a cellular response against a cell characterized by presentation of an antigen with class I MHC and preferably is capable of stimulating an antigen-responsive cytotoxic T-lymphocyte (CTL).

"Antigen processing" or "processing" refers to the degradation of a peptide, polypeptide or protein into procession products, which are fragments of said peptide, polypeptide or protein (e.g., the degradation of a polypeptide into peptides) and the association of one or more of these fragments (e.g., via binding) with MHC molecules for presentation by cells, preferably antigen presenting cells, to specific T cells.

"Antigen presenting cells" (APC) are cells which present peptide fragments of protein antigens in association with MHC molecules on their cell surface. Some APCs may activate antigen specific T cells.

Professional antigen-presenting cells are very efficient at internalizing antigen, either by phagocytosis or by receptor-mediated endocytosis, and then displaying a fragment of the antigen, bound to a class II MHC molecule, on their membrane. The T cell recognizes and interacts with the antigen-class II MHC molecule complex on the membrane of the antigen-presenting cell. An additional co-stimulatory signal is then produced by the antigen-presenting cell, leading to activation of the T cell. The expression of co-stimulatory molecules is a defining feature of professional antigen-presenting cells.

The main types of professional antigen-presenting cells are dendritic cells, which have the broadest range of antigen presentation, and are probably the most important antigen-presenting cells, macrophages, B-cells, and certain activated epithelial cells. Dendritic cells (DCs) are leukocyte populations that present antigens captured in peripheral tissues to T cells via both MHC class II and I antigen presentation pathways. It is well known that dendritic cells are potent inducers of immune responses and the activation of these cells is a critical step for the induction of antitumoral immunity. Dendritic cells are conveniently categorized as "immature" and "mature" cells, which can be used as a simple way to discriminate between two well characterized phenotypes. However, this nomenclature should not be construed to exclude all possible intermediate stages of differentiation. Immature dendritic cells are characterized as antigen presenting cells with a high capacity for antigen uptake and processing, which correlates with the high expression of Fcγ receptor and mannose receptor. The mature phenotype is typically characterized by a lower expression of these markers, but a high expression of cell surface molecules responsible for T cell activation such as class I and class II MHC, adhesion molecules (e.g. CD54 and CD11) and costimulatory molecules (e.g., CD40, CD80, CD86 and 4-1 BB). Dendritic cell maturation is referred to as the status of dendritic cell activation at which such antigen-presenting dendritic cells lead to T cell priming, while presentation by immature dendritic cells results in tolerance. Dendritic cell maturation is chiefly caused by biomolecules with microbial features detected by innate receptors (bacterial DNA, viral RNA, endotoxin, etc.), pro-inflammatory cytokines (TNF, IL-1, IFNs), ligation of CD40 on the dendritic cell surface by CD40L, and substances released from cells undergoing stressful cell death. The dendritic cells can be derived by culturing bone marrow cells in vitro with cytokines, such as granulocyte-macrophage colony-stimulating factor (GM-CSF) and tumor necrosis factor alpha.

Non-professional antigen-presenting cells do not constitutively express the MHC class II proteins required for interaction with naive T cells; these are expressed only upon stimulation of the non-professional antigen-presenting cells by certain cytokines such as IFNγ.

Antigen presenting cells can be loaded with MHC class I presented peptides by transducing the cells with nucleic acid, preferably RNA, encoding a peptide or polypeptide comprising the peptide to be presented, e.g. a nucleic acid encoding an antigen or polypeptide used for vaccination.

In some embodiments, a pharmaceutical composition or vaccine comprising a nucleic acid delivery vehicle that targets a dendritic or other antigen presenting cell may be administered to a patient, resulting in transfection that occurs in vivo. In vivo transfection of dendritic cells, for example, may generally be performed using any methods known in the art, such as those described in WO 97/24447, or the gene gun approach described by Mahvi et al., Immunology and cell Biology 75: 456-460, 1997.

According to the invention, the term "antigen presenting cell" also includes target cells.

"Target cell" shall mean a cell which is a target for an immune response such as a cellular immune response. Target cells include cells that present an antigen, i.e. a peptide fragment derived from an antigen, and include any undesirable cell such as a cancer cell. In preferred embodiments, the target cell is a cell expressing an antigen as described herein and preferably presenting said antigen with class I MHC.

The term "portion" refers to a fraction. With respect to a particular structure such as an amino acid sequence or protein the term "portion" thereof may designate a continuous or a discontinuous fraction of said structure. Preferably, a portion of an amino acid sequence comprises at least 1%, at least 5%, at least 10%, at least 20%, at least 30%, preferably at least 40%, preferably at least 50%, more preferably at least 60%, more preferably at least 70%, even more preferably at least 80%, and most preferably at least 90% of the amino acids of said amino acid sequence. Preferably, if the portion is a discontinuous fraction said discontinuous fraction is composed of 2, 3, 4, 5, 6, 7, 8, or more parts of a structure, each part being a continuous element of the structure. For example, a discontinuous fraction of an amino acid sequence may be composed of 2, 3, 4, 5, 6, 7, 8, or more, preferably not more than 4 parts of said amino acid sequence, wherein each part preferably comprises at least 5 continuous amino acids, at least 10 continuous amino acids, preferably at least 20 continuous amino acids, preferably at least 30 continuous amino acids of the amino acid sequence.

The terms "part" and "fragment" are used interchangeably herein and refer to a continuous element. For example, a part of a structure such as an amino acid sequence or protein refers to a continuous element of said structure. A portion, a part or a fragment of a structure preferably comprises one or more functional properties of said structure. For example, a portion, a part or a fragment of an epitope, peptide or protein is preferably immunologically equivalent to the epitope, peptide or protein it is derived from. In the context of the present invention, a "part" of a structure such as an amino acid sequence preferably comprises, preferably consists of at least 10%, at least 20%, at least 30%, at least 40%, at least 50%, at least 60%, at least 70%, at least 80%, at least 85%, at least 90%, at least 92%, at least 94%, at least 96%, at least 98%, at least 99% of the entire structure or amino acid sequence.

The term "immunoreactive cell" in the context of the present invention relates to a cell which exerts effector functions during an immune reaction. An "immunoreactive cell" preferably is capable of binding an antigen or a cell characterized by presentation of an antigen or a peptide fragment thereof (e.g. a T cell epitope) and mediating an immune response. For example, such cells secrete cytokines and/or chemokines, secrete antibodies, recognize cancerous cells, and optionally eliminate such cells. For example, immunoreactive cells comprise T cells (cytotoxic T cells, helper T cells, tumor infiltrating T cells), B cells, natural killer cells, neutrophils, macrophages, and dendritic cells. Preferably, in the context of the present invention, "immunoreactive cells" are T cells, preferably CD4$^+$ and/or CD8$^+$ T cells.

Preferably, an "immunoreactive cell" recognizes an antigen or a peptide fragment thereof with some degree of specificity, in particular if presented in the context of MHC molecules such as on the surface of antigen presenting cells or diseased cells such as cancer cells. Preferably, said recognition enables the cell that recognizes an antigen or a peptide fragment thereof to be responsive or reactive. If the cell is a helper T cell (CD4$^+$ T cell) bearing receptors that recognize an antigen or a peptide fragment thereof in the context of MHC class II molecules such responsiveness or reactivity may involve the release of cytokines and/or the activation of CD8$^+$ lymphocytes (CTLs) and/or B-cells. If the cell is a CTL such responsiveness or reactivity may involve the elimination of cells presented in the context of MHC class I molecules, i.e., cells characterized by presentation of an antigen with class I MHC, for example, via apoptosis or perforin-mediated cell lysis. According to the invention, CTL responsiveness may include sustained calcium flux, cell division, production of cytokines such as IFN-γ and TNF-α, up-regulation of activation markers such as CD44 and CD69, and specific cytolytic killing of antigen expressing target cells. CTL responsiveness may also be determined using an artificial reporter that accurately indicates CTL responsiveness. Such CTL that recognize an antigen or an antigen fragment and are responsive or reactive are also tended "antigen-responsive CTL" herein. If the cell is a B cell such responsiveness may involve the release of immunoglobulins.

The terms "T cell" and "T lymphocyte" are used interchangeably herein and include T helper cells (CD4+ T cells) and cytotoxic T cells (CTLs, CD8+ T cells) which comprise cytolytic T cells.

T cells belong to a group of white blood cells known as lymphocytes, and play a central role in cell-mediated immunity. They can be distinguished from other lymphocyte types, such as B cells and natural killer cells by the presence of a special receptor on their cell surface called T cell receptor (TCR). The thymus is the principal organ responsible for the maturation of T cells. Several different subsets of T cells have been discovered, each with a distinct function.

T helper cells assist other white blood cells in immunologic processes, including maturation of B cells into plasma cells and activation of cytotoxic T cells and macrophages, among other functions. These cells are also known as CD4+ T cells because they express the CD4 protein on their surface. Helper T cells become activated when they are presented with peptide antigens by MHC class II molecules that are expressed on the surface of antigen presenting cells (APCs). Once activated, they divide rapidly and secrete small proteins called cytokines that regulate or assist in the active, immune response.

Cytotoxic T cells destroy virally infected cells and tumor cells, and are also implicated in transplant rejection. These cells are also known as CD8+ T cells since they express the CD8 glycoprotein at their surface. These cells recognize their targets by binding to antigen associated with MHC class I, which is present on the surface of nearly every cell of the body.

A majority of T cells have a T cell receptor (TCR) existing as a complex of several proteins. The actual T cell receptor is composed of two separate peptide chains, which are produced from the independent T cell receptor alpha and beta (TCRα and TCRβ) genes and are called α- and β-TCR chains. γδ T cells (gamma delta T cells) represent a small subset of T cells that possess a distinct T cell receptor (TCR) on their surface. However, in γδ T cells, the TCR is made up of one γ-chain and one δ-chain. This group of T cells is much less common (2% of total T cells) than the αβ T cells.

The first signal in activation of T cells is provided by binding of the T cell receptor to a short peptide presented by the MHC on another cell. This ensures that only a T cell with a TCR specific to that peptide is activated. The partner cell is usually an antigen presenting cell such as a professional antigen presenting cell, usually a dendritic cell in the case of naive responses, although B cells and macrophages can be important APCs.

According to the present invention, a molecule is capable of binding to a target if it has a significant affinity for said predetermined target and binds to said predetermined target in standard assays. "Affinity" or "binding affinity" is often measured by equilibrium dissociation constant ($K_D$). A molecule is not (substantially) capable of binding to a target if it has no significant affinity for said target and does not bind significantly to said target in standard assays.

Cytotoxic T lymphocytes may be generated in vivo by incorporation of an antigen or a peptide fragment thereof into antigen-presenting cells in vivo. The antigen or a peptide fragment thereof may be represented as protein, as DNA (e.g. within a vector) or as RNA. The antigen may be processed to produce a peptide partner for the MHC molecule, while a fragment thereof may be presented without the need for further processing. The latter is the case in particular, if these can bind to MHC molecules. In general, administration to a patient by intradermal injection is possible. However, injection may also be carried out intranodally into a lymph node (Maloy et al. (2001), Proc Natl Acad Sci USA 98:3299-303). The resulting cells present the complex of interest and are recognized by autologous cytotoxic T lymphocytes which then propagate.

Specific activation of CD4+ or CD8+ T cells may be detected in a variety of ways. Methods for detecting specific T cell activation include detecting the proliferation of T cells, the production of cytokines (e.g., lymphokines), or the generation of cytolytic activity. For CD4+ T cells, a preferred method for detecting specific T cell activation is the detection of the proliferation of T cells. For CD8+ T cells, a preferred method for detecting specific T cell activation is the detection of the generation of cytolytic activity.

By "cell characterized by presentation of an antigen" or "cell presenting an antigen" or similar expressions is meant a cell such as a diseased cell, e.g. a cancer cell, or an antigen presenting cell presenting the antigen it expresses or a fragment derived from said antigen, e.g. by processing of the antigen, in the context of MHC molecules, in particular MHC Class I molecules. Similarly, the teens "disease characterized by presentation of an antigen" denotes a disease involving cells characterized by presentation of an antigen, in particular with class I MHC. Presentation of an antigen by a cell may be effected by transfecting the cell with a nucleic acid such as RNA encoding the antigen.

By "fragment of an antigen which is presented" or similar expressions is meant that the fragment can be presented by MHC class I or class II, preferably MHC class I, e.g. when added directly to antigen presenting cells. In one embodiment, the fragment is a fragment which is naturally presented by cells expressing an antigen.

The term "immunologically equivalent" means that the immunologically equivalent molecule such as the immunologically equivalent amino acid sequence exhibits the same or essentially the same immunological properties and/or exerts the same or essentially the same immunological effects, e.g., with respect to the type of the immunological effect such as induction of a humoral and/or cellular immune response, the strength and/or duration of the induced immune reaction, or the specificity of the induced immune reaction. In the context of the present invention, the term "immunologically equivalent" is preferably used with respect to the immunological effects or properties of a peptide used for immunization. For example, an amino acid sequence is immunologically equivalent to a reference amino acid sequence if said amino acid sequence when exposed to the immune system of a subject induces an immune reaction having a specificity of reacting with the reference amino acid sequence.

The term "immune effector functions" in the context of the present invention includes any functions mediated by components of the immune system that result, for example, in the killing of tumor cells, or in the inhibition of tumor growth and/or inhibition of tumor development, including inhibition of tumor dissemination and metastasis. Preferably, the immune effector functions in the context of the present invention are T cell mediated effector functions. Such functions comprise in the case of a helper T cell (CD4+

T cell) the recognition of an antigen or an antigen fragment in the context of MHC class II molecules by T cell receptors, the release of cytokines and/or the activation of CD8+ lymphocytes (CTLs) and/or B-cells, and in the case of CTL the recognition of an antigen or an antigen fragment in the context of MHC class I molecules by T cell receptors, the elimination of cells presented in the context of MHC class I molecules, i.e., cells characterized by presentation of an antigen with class I MHC, for example, via apoptosis or perforin-mediated cell lysis, production of cytokines such as IFN-γ and TNF-α, and specific cytolytic killing of antigen expressing target cells.

According to the invention, the term "score" relates to a result, usually expressed numerically, of a test or examination. Terms such as "score better" or "score best" relate to a better result or the best result of a test or examination.

Terms such as "predict", "predicting" or "prediction" relate to the determination of a likelihood.

According to the invention, ascertaining a score for binding of a peptide to one or more MHC molecules includes determining the likelihood of binding of a peptide to one or more MHC molecules.

A score for binding of a peptide to one or more MHC molecules may be ascertained by using any peptide:MHC binding predictive tools. For example, the immune epitope database analysis resource (IEDB-AR: http://tools.iedb.org) may be used.

Predictions are usually made against a set of MHC molecules such as a set of different MHC alleles such as all possible MHC alleles or a set or subset of MHC alleles found in a patient preferably having the modification(s) the immunogenicity of which is to be determined according to the invention.

According to the invention, ascertaining a score for binding of a modified peptide when present in a MHC-peptide complex to one or more T cell receptors includes determining the likelihood of binding of a peptide when present in a complex with an MHC molecule to T cell receptors.

Predictions may be made against one T cell receptor such as a T cell receptor found in a patient or preferably against a set of T cell receptors such as an unknown set of different T cell receptors or a set or subset of T cell receptors found in a patient preferably having the modification(s) the immunogenicity of which is to be determined according to the invention.

Furthermore, predictions are usually made against a set of MHC molecules such as a set of different MHC alleles such as all possible MHC alleles or a set or subset of MHC alleles found in a patient preferably having the modification(s) the immunogenicity of which is to be determined according to the invention.

A score for binding of a modified peptide when present in a MHC-peptide complex to one or more T cell receptors may be ascertained by estimating the effect of the modification on the binding of a T cell receptor-peptide-MHC complex given an (unknown) T cell receptor repertoire. The score for binding of a modified peptide when present in a MHC-peptide complex to one or more T cell receptors may generally be defined as a kind of a proxy for the recognition a given peptide-MHC molecule to a matching T cell receptor.

The score for binding of a modified peptide when present in a MHC-peptide complex to one or more T cell receptors may be ascertained by ascertaining the physico-chemical differences between the modified and the non-modified amino acid. For example, substitution matrices may be used. Such matrices describe the rate at which one amino acid in a sequence changes to other amino acid states over time.

For example log-odds matrices such as evolutionary based log-odds matrices may be used: a substitution with a low log odds score has a better chance of finding a matching T cell receptor from the pool of (unknown) T cell receptor molecules than a substitution with a high log odds score (due to negative selection of T cell receptor matching non-modified peptides). However there are other ways of ascertaining this score. For example, considering the position of the mutation in the peptide (some positions may have a lower impact on binding than others), taking into account the nearest neighbors of the substituted amino acid (which could impact the secondary structure of the substituted amino acid), taking into account the entire peptide sequence, taking into account the complete structural information of the peptide in the MHC molecule, an so on. Ascertaining the score could also involve determination of a T cell receptor repertoire (such as the T cell receptor repertoire of a patient or a subset thereof) e.g. via NGS and performing docking simulations of T cell receptor-peptide-MHC complexes.

The present invention also may comprise performing the method of the invention on different peptides comprising the same modification(s) and/or different modifications.

The term "different peptides comprising the same modification(s)" in one embodiment relates to peptides comprising or consisting of different fragments of a modified protein, said different fragments comprising the same modification(s) present in the protein but differing in length and/or position of the modification(s). If a protein has a modification at position x, two or more fragments of said protein each comprising a different sequence window of said protein covering said position x are considered different peptides comprising the same modification(s).

The term "different peptides comprising different modifications" in one embodiment relates to peptides either of the same and/or differing lengths comprising different modifications of either of the same and/or different proteins. If a protein has modifications at positions x and y, two fragments of said protein each comprising a sequence window of said protein covering either position x or position y are considered different peptides comprising different modifications.

The present invention also may comprise breaking of protein sequences having modifications the immunogenicity of which is to be determined according to the invention into appropriate peptide lengths for MHC binding and ascertaining scores for binding to one or more MHC molecules of different modified peptides comprising the same and/or different modifications of either the same and/or different proteins. Outputs may be ranked and may consist of a list of peptides and their predicted scores, indicating their likelihood of binding.

The step of ascertaining a score for binding of the non-modified peptide to one or more MHC molecules and/or the step of ascertaining a score for binding of the modified peptide when present in a MHC-peptide complex to one or more T cell receptors may subsequently performed with all different modified peptides comprising the same and/or different modifications, a subset thereof, e.g. those modified peptides comprising the same and/or different modifications scoring best for binding to one or more MHC molecules, or only with the one modified peptide scoring best for binding to one or more MHC molecules.

Following said further steps, the results may be ranked and may consist of a list of peptides and their predicted scores, indicating their likelihood of being immunogenic.

Preferably, in such ranking, a score for binding of the modified peptide to one or more MHC molecules is weighted higher than a score for binding of the modified peptide when present in a MHC-peptide complex to one or more T cell receptors, preferably a score for the chemical and physical similarities between the non-modified and modified amino acids and a score for binding of the modified peptide when present in a MHC-peptide complex to one or more T cell receptors, preferably a score for the chemical and physical similarities between the non-modified and modified amino acids is weighted higher than a score for binding of the non-modified peptide to one or more MHC molecules.

The amino acid modifications the immunogenicity of which is to be determined according to the present invention may result from mutations in the nucleic acid of a cell. Such mutations may be identified by known sequencing techniques.

In one embodiment, the mutations are cancer specific somatic mutations in a tumor specimen of a cancer patient which may be determined by identifying sequence differences between the genome, exome and/or transcriptome of a tumor specimen and the genome, exome and/or transcriptome of a non-tumorigenous specimen.

According to the invention a tumor specimen relates to any sample such as a bodily sample derived from a patient containing or being expected of containing tumor or cancer cells. The bodily sample may be any tissue sample such as blood, a tissue sample obtained from the primary tumor or from tumor metastases or any other sample containing tumor or cancer cells. Preferably, a bodily sample is blood and cancer specific somatic mutations or sequence differences are determined in one or more circulating tumor cells (CTCs) contained in the blood. In another embodiment, a tumor specimen relates to one or more isolated tumor or cancer cells such as circulating tumor cells (CTCs) or a sample containing one or more isolated tumor or cancer cells such as circulating tumor cells (CTCs).

A non-tumorigenous specimen relates to any sample such as a bodily sample derived from a patient or another individual which preferably is of the same species as the patient, preferably a healthy individual not containing or not being expected of containing tumor or cancer cells. The bodily sample may be any tissue sample such as blood or a sample from a non-tumorigenous tissue.

The invention may involve the determination of the cancer mutation signature of a patient. The term "cancer mutation signature" may refer to all cancer mutations present in one or more cancer cells of a patient or it may refer to only a portion of the cancer mutations present in one or more cancer cells of a patient. Accordingly, the present invention may involve the identification of all cancer specific mutations present in one or more cancer cells of a patient or it may involve the identification of only a portion of the cancer specific mutations present in one or more cancer cells of a patient. Generally, the methods of the invention provides for the identification of a number of mutations which provides a sufficient number of modifications or modified peptides to be included in the methods of the invention.

Preferably, the mutations identified according to the present invention are non-synonymous mutations, preferably non-synonymous mutations of proteins expressed in a tumor or cancer cell.

In one embodiment, cancer specific somatic mutations or sequence differences are determined in the genome, preferably the entire genome, of a tumor specimen. Thus, the invention may comprise identifying the cancer mutation signature of the genome, preferably the entire genome of one or more cancer cells. In one embodiment, the step of identifying cancer specific somatic mutations in a tumor specimen of a cancer patient comprises identifying the genome-wide cancer mutation profile.

In one embodiment, cancer specific somatic mutations or sequence differences are determined in the exome, preferably the entire exome, of a tumor specimen. Thus, the invention may comprise identifying the cancer mutation signature of the exome, preferably the entire exome of one or more cancer cells. In one embodiment, the step of identifying cancer specific somatic mutations in a tumor specimen of a cancer patient comprises identifying the exome-wide cancer mutation profile.

In one embodiment, cancer specific somatic mutations or sequence differences are determined in the transcriptome, preferably the entire transcriptome, of a tumor specimen. Thus, the invention may comprise identifying the cancer mutation signature of the transcriptome, preferably the entire transcriptome of one or more cancer cells. In one embodiment, the step of identifying cancer specific somatic mutations in a tumor specimen of a cancer patient comprises identifying the transcriptome-wide cancer mutation profile.

In one embodiment, the step of identifying cancer specific somatic mutations or identifying sequence differences comprises single cell sequencing of one or more, preferably 2, 3, 4, 5, 6, 7, 8, 9, 10, 11, 12, 13, 14, 15, 16, 17, 18, 19, 20 or even more cancer cells. Thus, the invention may comprise identifying a cancer mutation signature of said one or more cancer cells. In one embodiment, the cancer cells are circulating tumor cells. The cancer cells such as the circulating tumor cells may be isolated prior to single cell sequencing.

In one embodiment, the step of identifying cancer specific somatic mutations or identifying sequence differences involves using next generation sequencing (NGS).

In one embodiment, the step of identifying cancer specific somatic mutations or identifying sequence differences comprises sequencing genomic DNA and/or RNA of the tumor specimen.

To reveal cancer specific somatic mutations or sequence differences the sequence information obtained from the tumor specimen is preferably compared with a reference such as sequence information obtained from sequencing nucleic acid such as DNA or RNA of normal non-cancerous cells such as germline cells which may either be obtained from the patient or a different individual. In one embodiment, normal genomic germline DNA is obtained from peripheral blood mononuclear cells (PBMCs)

The term "genome" relates to the total amount of genetic information in the chromosomes of an organism or a cell.

The term "exome" refers to part of the genome of an organism formed by exons, which are coding portions of expressed genes. The exome provides the genetic blueprint used in the synthesis of proteins and other functional gene products. It is the most functionally relevant part of the genome and, therefore, it is most likely to contribute to the phenotype of an organism. The exome of the human genome is estimated to comprise 1.5% of the total genome (Ng, P C et al., *PLoS Gen.*, 4(8): 1-15, 2008).

The term "transcriptome" relates to the set of all RNA molecules, including mRNA, rRNA, tRNA, and other non-coding RNA produced in one cell or a population of cells. In context of the present invention the transcriptome means the set of all RNA molecules produced in one cell, a population of cells, preferably a population of cancer cells, or all cells of a given individual at a certain time point.

A "nucleic acid" is according to the invention preferably deoxyribonucleic acid (DNA) or ribonucleic acid (RNA), more preferably RNA, most preferably in vitro transcribed RNA (IVT RNA) or synthetic RNA. Nucleic acids include according to the invention genomic DNA, cDNA, mRNA, recombinantly produced and chemically synthesized molecules. According to the invention, a nucleic acid may be present as a single-stranded or double-stranded and linear or covalently circularly closed molecule. A nucleic acid can, according to the invention, be isolated. The term "isolated nucleic acid" means, according to the invention, that the nucleic acid (i) was amplified in vitro, for example via polymerase chain reaction (PCR), (ii) was produced recombinantly by cloning, (iii) was purified, for example, by cleavage and separation by gel electrophoresis, or (iv) was synthesized, for example, by chemical synthesis. A nucleic can be employed for introduction into, i.e. transfection of, cells, in particular, in the form of RNA which can be prepared by in vitro transcription from a DNA template. The RNA can moreover be modified before application by stabilizing sequences, capping, and polyadenylation.

The term "genetic material" refers to isolated nucleic acid, either DNA or RNA, a section of a double helix, a section of a chromosome, or an organism's or cell's entire genome, in particular its exome or transcriptome.

The term "mutation" refers to a change of or difference in the nucleic acid sequence (nucleotide substitution, addition or deletion) compared to a reference. A "somatic mutation" can occur in any of the cells of the body except the germ cells (sperm and egg) and therefore are not passed on to children. These alterations can (but do not always) cause cancer or other diseases. Preferably a mutation is a non-synonymous mutation. The term "non-synonymous mutation" refers to a mutation, preferably a nucleotide substitution, which does result in an amino acid change such as an amino acid substitution in the translation product.

According to the invention, the term "mutation" includes point mutations, Indels, fusions, chromothripsis and RNA edits.

According to the invention, the term "Indel" describes a special mutation class, defined as a mutation resulting in a colocalized insertion and deletion and a net gain or loss in nucleotides. In coding regions of the genome, unless the length of an indel is a multiple of 3, they produce a frameshift mutation. Indels can be contrasted with a point mutation; where an Indel inserts and deletes nucleotides from a sequence, a point mutation is a form of substitution that replaces one of the nucleotides.

Fusions can generate hybrid genes formed from two previously separate genes. It can occur as the result of a translocation, interstitial deletion, or chromosomal inversion. Often, fusion genes are oncogenes. Oncogenic fusion genes may lead to a gene product with a new or different function from the two fusion partners. Alternatively, a proto-oncogene is fused to a strong promoter, and thereby the oncogenic function is set to function by an upregulation caused by the strong promoter of the upstream fusion partner. Oncogenic fusion transcripts may also be caused by trans-splicing or read-through events.

According to the invention, the term "chromothripsis" refers to a genetic phenomenon by which specific regions of the genome are shattered and then stitched together via a single devastating event.

According to the invention, the term "RNA edit" or "RNA editing" refers to molecular processes in which the information content in an RNA molecule is altered through a chemical change in the base makeup. RNA editing includes nucleoside modifications such as cytidine (C) to uridine (U) and adenosine (A) to inosine (I) deaminations, as well as non-templated nucleotide additions and insertions. RNA editing in mRNAs effectively alters the amino acid sequence of the encoded protein so that it differs from that predicted by the genomic DNA sequence.

The term "cancer mutation signature" refers to a set of mutations which are present in cancer cells when compared to non-cancerous reference cells.

According to the invention, a "reference" may be used to correlate and compare the results obtained in the methods of the invention from a tumor specimen. Typically the "reference" may be obtained on the basis of one or more normal specimens, in particular specimens which are not affected by a cancer disease, either obtained from a patient or one or more different individuals, preferably healthy individuals, in particular individuals of the same species. A "reference" can be determined empirically by testing a sufficiently large number of normal specimens.

Any suitable sequencing method can be used according to the invention for determining mutations, Next Generation Sequencing (NGS) technologies being preferred. Third Generation Sequencing methods might substitute for the NGS technology in the future to speed up the sequencing step of the method. For clarification purposes: the terms "Next Generation Sequencing" or "NGS" in the context of the present invention mean all novel high throughput sequencing technologies which, in contrast to the "conventional" sequencing methodology known as Sanger chemistry, read nucleic acid templates randomly in parallel along the entire genome by breaking the entire genome into small pieces. Such NGS technologies (also known as massively parallel sequencing technologies) are able to deliver nucleic acid sequence information of a whole genome, exome, transcriptome (all transcribed sequences of a genome) or methylome (all methylated sequences of a genome) in very short time periods, e.g. within 1-2 weeks, preferably within 1-7 days or most preferably within less than 24 hours and allow, in principle, single cell sequencing approaches. Multiple NGS platforms which are commercially available or which are mentioned in the literature can be used in the context of the present invention e.g. those described in detail in Zhang et al. 2011: *The impact of next-generation sequencing on genomics. J. Genet Genomics* 38 (3), 95-109; or in Voelkerding et al. 2009: *Next generation sequencing: From basic research to diagnostics. Clinical chemistry* 55, 641-658. Non-limiting examples of such NGS technologies/platforms are 1) The sequencing-by-synthesis technology known as pyrosequencing implemented e.g. in the GS-FLX 454 Genome Sequencer™ of Roche-associated company 454 Life Sciences (Branford, Conn.), first described in Ronaghi et al. 1998: *A sequencing method based on real-time pyrophosphate". Science* 281 (5375), 363-365. This technology uses an emulsion PCR in which single-stranded DNA binding beads are encapsulated by vigorous vortexing into aqueous micelles containing PCR reactants surrounded by oil for emulsion PCR amplification. During the pyrosequencing process, light emitted from phosphate molecules during nucleotide incorporation is recorded as the polymerase synthesizes the DNA strand.

2) The sequencing-by-synthesis approaches developed by Solexa (now part of Illumina Inc., San Diego, Calif.) which is based on reversible dye-terminators and implemented e.g. in the Illumina/Solexa Genome Analyzer™ and in the Illumina HiSeq 2000 Genome Analyzer™. In this technology, all four nucleotides are added simultaneously into oligo-primed cluster fragments in flow-cell channels along with DNA polymerase. Bridge amplification extends cluster strands with all four fluorescently labeled nucleotides for sequencing.

3) Sequencing-by-ligation approaches, e.g. implemented in the SOLid™ platform of Applied Biosystems (now Life Technologies Corporation, Carlsbad, Calif.). In this technology, a pool of all possible oligonucleotides of a fixed length are labeled according to the sequenced position. Oligonucleotides are annealed and ligated; the preferential ligation by DNA ligase for matching sequences results in a signal informative of the nucleotide at that position. Before sequencing, the DNA is amplified by emulsion PCR. The resulting bead, each containing only copies of the same DNA molecule, are deposited on a glass slide. As a second example, he Polonator™ G.007 platform of Dover Systems (Salem, N.H.) also employs a sequencing-by-ligation approach by using a randomly arrayed, bead-based, emulsion PCR to amplify DNA fragments for parallel sequencing.

4) Single-molecule sequencing technologies such as e.g. implemented in the PacBio RS system of Pacific Biosciences (Menlo Park, Calif.) or in the HeliScope™ platform of Helicos Biosciences (Cambridge, Mass.). The distinct characteristic of this technology is its ability to sequence single DNA or RNA molecules without amplification, defined as Single-Molecule Real Time (SMRT) DNA sequencing. For example, HeliScope uses a highly sensitive fluorescence detection system to directly detect each nucleotide as it is synthesized. A similar approach based on fluorescence resonance energy transfer (FRET) has been developed from Visigen Biotechnology (Houston, Tex.). Other fluorescence-based single-molecule techniques are from U.S. Genomics (GeneEngine™) and Genovoxx (AnyGene™).

5) Nano-technologies for single-molecule sequencing in which various nanostructures are used which are e.g. arranged on a chip to monitor the movement of a polymerase molecule on a single strand during replication. Non-limiting examples for approaches based on nano-technologies are the GridON™ platform of Oxford Nanopore Technologies (Oxford, UK), the hybridization-assisted nano-pore sequencing (HANS™) platforms developed by Nabsys (Providence, R.I.), and the proprietary ligase-based DNA sequencing platform with DNA nanoball (DNB) technology called combinatorial probe-anchor ligation (cPAL™)

6) Electron microscopy based technologies for single-molecule sequencing, e.g. those developed by LightSpeed Genomics (Sunnyvale, Calif.) and Halcyon Molecular (Redwood City, Calif.)

7) Ion semiconductor sequencing which is based on the detection of hydrogen ions that are released during the polymerisation of DNA. For example, Ion Torrent Systems (San Francisco, Calif.) uses a high-density array of micro-machined wells to perform this biochemical process in a massively parallel way. Each well holds a different DNA template. Beneath the wells is an ion-sensitive layer and beneath that a proprietary Ion sensor.

Preferably, DNA and RNA preparations serve as starting material for NGS. Such nucleic acids can be easily obtained from samples such as biological material, e.g. from fresh, flash-frozen or formalin-fixed paraffin embedded tumor tissues (FFPE) or from freshly isolated cells or from CTCs which are present in the peripheral blood of patients. Normal non-mutated genomic DNA or RNA can be extracted from normal, somatic tissue, however germline cells are preferred in the context of the present invention. Germline DNA or RNA may be extracted from peripheral blood mononuclear cells (PBMCs) in patients with non-hematological malignancies. Although nucleic acids extracted from FFPE tissues or freshly isolated single cells are highly fragmented, they are suitable for NGS applications.

Several targeted NGS methods for exome sequencing are described in the literature (for review see e.g. Teer and Mullikin 2010: *Human Mol Genet* 19 (2), R145-51), all of which can be used in conjunction with the present invention. Many of these methods (described e.g. as genome capture, genome partitioning, genome enrichment etc.) use hybridization techniques and include array-based (e.g. Hodges et al. 2007: *Nat. Genet.* 39, 1522-1527) and liquid-based (e.g. Choi et al. 2009: *Proc. Natl. Acad. Sci USA* 106, 19096-19101) hybridization approaches. Commercial kits for DNA sample preparation and subsequent exome capture are also available: for example, Illumina Inc. (San Diego, Calif.) offers the TruSee™ DNA Sample Preparation Kit and the Exome Enrichment Kit TruSeq™ Exome Enrichment Kit.

In order to reduce the number of false positive findings in detecting cancer specific somatic mutations or sequence differences when comparing e.g. the sequence of a tumor sample to the sequence of a reference sample such as the sequence of a germ line sample it is preferred to determine the sequence in replicates of one or both of these sample types. Thus, it is preferred that the sequence of a reference sample such as the sequence of a germ line sample is determined twice, three times or more. Alternatively or additionally, the sequence of a tumor sample is determined twice, three times or more. It may also be possible to determine the sequence of a reference sample such as the sequence of a germ line sample and/or the sequence of a tumor sample more than once by determining at least once the sequence in genomic DNA and determining at least once the sequence in RNA of said reference sample and/or of said tumor sample. For example, by determining the variations between replicates of a reference sample such as a germ line sample the expected rate of false positive (FDR) somatic mutations as a statistical quantity can be estimated. Technical repeats of a sample should generate identical results and any detected mutation in this "same vs. same comparison" is a false positive. In particular, to determine the false discovery rate for somatic mutation detection in a tumor sample relative to a reference sample, a technical repeat of the reference sample can be used as a reference to estimate the number of false positives. Furthermore, various quality related metrics (e.g. coverage or SNP quality) may be combined into a single quality score using a machine learning approach. For a given somatic variation all other variations with an exceeding quality score may be counted, which enables a ranking of all variations in a dataset.

In the context of the present invention, the term "RNA" relates to a molecule which comprises at least one ribonucleotide residue and preferably being entirely or substantially composed of ribonucleotide residues. "Ribonucleotide" relates to a nucleotide with a hydroxyl group at the 2'-position of a β-D-ribofuranosyl group. The term "RNA" comprises double-stranded RNA, single-stranded RNA, isolated RNA such as partially or completely purified RNA, essentially pure RNA, synthetic RNA, and recombinantly generated RNA such as modified RNA which differs from naturally occurring RNA by addition, deletion, substitution and/or alteration of one or more nucleotides. Such alterations can include addition of non-nucleotide material, such as to the end(s) of a RNA or internally, for example at one or more nucleotides of the RNA. Nucleotides in RNA molecules can also comprise non-standard nucleotides, such as non-naturally occurring nucleotides or chemically synthesized nucleotides or deoxynucleotides. These altered RNAs can be referred to as analogs or analogs of naturally-occurring RNA.

According to the present invention, the term "RNA" includes and preferably relates to "mRNA". The term "mRNA" means "messenger-RNA" and relates to a "transcript" which is generated by using a DNA template and encodes a peptide or polypeptide. Typically, an mRNA comprises a 5'-UTR, a protein coding region, and a 3'-UTR. mRNA only possesses limited half-life in cells and in vitro. In the context of the present invention, mRNA may be generated by in vitro transcription from a DNA template. The in vitro transcription methodology is known to the skilled person. For example, there is a variety of in vitro transcription kits commercially available.

According to the invention, the stability and translation efficiency of RNA may be modified as required. For example, RNA may be stabilized and its translation increased by one or more modifications having a stabilizing effects and/or increasing translation efficiency of RNA. Such modifications are described, for example, in PCT/EP2006/009448 incorporated herein by reference. In order to increase expression of the RNA used according to the present invention, it may be modified within the coding region, i.e. the sequence encoding the expressed peptide or protein, preferably without altering the sequence of the expressed peptide or protein, so as to increase the GC-content to increase mRNA stability and to perform a codon optimization and, thus, enhance translation in cells.

The term "modification" in the context of the RNA used in the present invention includes any modification of an RNA which is not naturally present in said RNA.

In one embodiment of the invention, the RNA used according to the invention does not have uncapped 5'-triphosphates. Removal of such uncapped 5'-triphosphates can be achieved by treating RNA with a phosphatase.

The RNA according to the invention may have modified ribonucleotides in order to increase its stability and/or decrease cytotoxicity. For example, in one embodiment, in the RNA used according to the invention 5-methylcytidine is substituted partially or completely, preferably completely, for cytidine. Alternatively or additionally, in one embodiment, in the RNA used according to the invention pseudouridine is substituted partially or completely, preferably completely, for uridine.

In one embodiment, the term "modification" relates to providing an RNA with a 5'-cap or 5'-cap analog. The term "5'-cap" refers to a cap structure found on the 5'-end of an mRNA molecule and generally consists of a guanosine nucleotide connected to the mRNA via an unusual 5' to 5' triphosphate linkage. In one embodiment, this guanosine is methylated at the 7-position. The term "conventional 5'-cap" refers to a naturally occurring RNA 5'-cap, preferably to the 7-methylguanosine cap ($m^7G$). In the context of the present invention, the term "5'-cap" includes a 5'-cap analog that resembles the RNA cap structure and is modified to possess the ability to stabilize RNA and/or enhance translation of RNA if attached thereto, preferably in vivo and/or in a cell.

Providing an RNA with a 5'-cap or 5'-cap analog may be achieved by in vitro transcription of a DNA template in presence of said 5'-cap or 5'-cap analog, wherein said 5'-cap is co-transcriptionally incorporated into the generated RNA strand, or the RNA may be generated, for example, by in vitro transcription, and the 5'-cap may be attached to the RNA post-transcriptionally using capping enzymes, for example, capping enzymes of vaccinia virus.

The RNA may comprise further modifications. For example, a further modification of the RNA used in the present invention may be an extension or truncation of the naturally occurring poly(A) tail or an alteration of the 5'- or 3'-untranslated regions (UTR) such as introduction of a UTR which is not related to the coding region of said RNA, for example, the exchange of the existing 3'-UTR with or the insertion of one or more, preferably two copies of a 3'-UTR derived from a globin gene, such as alpha2-globin, alpha1-globin, beta-globin, preferably beta-globin, more preferably human beta-globin.

RNA having an unmasked poly-A sequence is translated more efficiently than RNA having a masked poly-A sequence. The term "poly(A) tail" or "poly-A sequence" relates to a sequence of adenyl (A) residues which typically is located on the 3'-end of a RNA molecule and "unmasked poly-A sequence" means that the poly-A sequence at the 3' end of an RNA molecule ends with an A of the poly-A sequence and is not followed by nucleotides other than A located at the 3' end, i.e. downstream, of the poly-A sequence. Furthermore, a long poly-A sequence of about 120 base pairs results in an optimal transcript stability and translation efficiency of RNA.

Therefore, in order to increase stability and/or expression of the RNA used according to the present invention, it may be modified so as to be present in conjunction with a poly-A sequence, preferably having a length of 10 to 500, more preferably 30 to 300, even more preferably 65 to 200 and especially 100 to 150 adenosine residues. In an especially preferred embodiment the poly-A sequence has a length of approximately 120 adenosine residues. To further increase stability and/or expression of the RNA used according to the invention, the poly-A sequence can be unmasked.

In addition, incorporation of a 3'-non translated region (UTR) into the 3'-non translated region of an RNA molecule can result in an enhancement in translation efficiency. A synergistic effect may be achieved by incorporating two or more of such 3'-non translated regions. The 3'-non translated regions may be autologous or heterologous to the RNA into which they are introduced. In one particular embodiment the 3'-non translated region is derived from the human β-globin gene.

A combination of the above described modifications, i.e. incorporation of a poly-A sequence, unmasking of a poly-A sequence and incorporation of one or more 3'-non translated regions, has a synergistic influence on the stability of RNA and increase in translation efficiency.

The term "stability" of RNA relates to the "half-life" of RNA. "Half-life" relates to the period of time which is needed to eliminate half of the activity, amount, or number of molecules. In the context of the present invention, the half-life of an RNA is indicative for the stability of said RNA. The half-life of RNA may influence the "duration of expression" of the RNA. It can be expected that RNA having a long half-life will be expressed for an extended time period.

Of course, if according to the present invention it is desired to decrease stability and/or translation efficiency of RNA, it is possible to modify RNA so as to interfere with the function of elements as described above increasing the stability and/or translation efficiency of RNA.

The term "expression" is used according to the invention in its most general meaning and comprises the production of RNA and/or peptides, polypeptides or proteins, e.g. by transcription and/or translation. With respect to RNA, the term "expression" or "translation" relates in particular to the production of peptides, polypeptides or proteins. It also comprises partial expression of nucleic acids. Moreover, expression can be transient or stable.

According to the invention, the term expression also includes an "aberrant expression" or "abnormal expression". "Aberrant expression" or "abnormal expression" means according to the invention that expression is altered, preferably increased, compared to a reference, e.g. a state in a subject not having a disease associated with aberrant or abnormal expression of a certain protein, e.g., a tumor antigen. An increase in expression refers to an increase by at least 10%, in particular at least 20%, at least 50% or at least 100%, or more. In one embodiment, expression is only found in a diseased tissue, while expression in a healthy tissue is repressed.

The term "specifically expressed" means that a protein is essentially only expressed in a specific tissue or organ. For example, a tumor antigen specifically expressed in gastric mucosa means that said protein is primarily expressed in gastric mucosa and is not expressed in other tissues or is not expressed to a significant extent in other tissue or organ types. Thus, a protein that is exclusively expressed in cells of the gastric mucosa and to a significantly lesser extent in any other tissue, such as testis, is specifically expressed in cells of the gastric mucosa. In some embodiments, a tumor antigen may also be specifically expressed under normal conditions in more than one tissue type or organ, such as in 2 or 3 tissue types or organs, but preferably in not more than 3 different tissue or organ types. In this case, the tumor antigen is then specifically expressed in these organs. For example, if a tumor antigen is expressed under normal conditions preferably to an approximately equal extent in lung and stomach, said tumor antigen is specifically expressed in lung and stomach.

In the context of the present invention, the term "transcription" relates to a process, wherein the genetic code in a DNA sequence is transcribed into RNA. Subsequently, the RNA may be translated into protein. According to the present invention, the term "transcription" comprises "in vitro transcription", wherein the term "in vitro transcription" relates to a process wherein RNA, in particular mRNA, is in vitro synthesized in a cell-free system, preferably using appropriate cell extracts. Preferably, cloning vectors are applied for the generation of transcripts. These cloning vectors are generally designated as transcription vectors and are according to the present invention encompassed by the term "vector". According to the present invention, the RNA used in the present invention preferably is in vitro transcribed RNA (IVT-RNA) and may be obtained by in vitro transcription of an appropriate DNA template. The promoter for controlling transcription can be any promoter for any RNA polymerase. Particular examples of RNA polymerases are the T7, T3, and SP6 RNA polymerases. Preferably, the in vitro transcription according to the invention is controlled by a T7 or SP6 promoter. A DNA template for in vitro transcription may be obtained by cloning of a nucleic acid, in particular cDNA, and introducing it into an appropriate vector for in vitro transcription. The cDNA may be obtained by reverse transcription of RNA.

The term "translation" according to the invention relates to the process in the ribosomes of a cell by which a strand of messenger RNA directs the assembly of a sequence of amino acids to make a peptide, polypeptide or protein.

Expression control sequences or regulatory sequences, which according to the invention may be linked functionally with a nucleic acid, can be homologous or heterologous with respect to the nucleic acid. A coding sequence and a regulatory sequence are linked together "functionally" if they are bound together covalently, so that the transcription or translation of the coding sequence is under the control or under the influence of the regulatory sequence. If the coding sequence is to be translated into a functional protein, with functional linkage of a regulatory sequence with the coding sequence, induction of the regulatory sequence leads to a transcription of the coding sequence, without causing a reading frame shift in the coding sequence or inability of the coding sequence to be translated into the desired protein or peptide.

The term "expression control sequence" or "regulatory sequence" comprises, according to the invention, promoters, ribosome-binding sequences and other control elements, which control the transcription of a nucleic acid or the translation of the derived RNA. In certain embodiments of the invention, the regulatory sequences can be controlled. The precise structure of regulatory sequences can vary depending on the species or depending on the cell type, but generally comprises 5'-untranscribed and 5'- and 3'-untranslated sequences, which are involved in the initiation of transcription or translation, such as TATA-box, capping-sequence, CAAT-sequence and the like. In particular, 5'-untranscribed regulatory sequences comprise a promoter region that includes a promoter sequence for transcriptional control of the functionally bound gene. Regulatory sequences can also comprise enhancer sequences or upstream activator sequences.

Preferably, according to the invention, RNA to be expressed in a cell is introduced into said cell. In one embodiment of the methods according to the invention, the RNA that is to be introduced into a cell is obtained by in vitro transcription of an appropriate DNA template.

According to the invention, terms such as "RNA capable of expressing" and "RNA encoding" are used interchangeably herein and with respect to a particular peptide or polypeptide mean that the RNA, if present in the appropriate environment, preferably within a cell, can be expressed to produce said peptide or polypeptide. Preferably, RNA according to the invention is able to interact with the cellular translation machinery to provide the peptide or polypeptide it is capable of expressing.

Terms such as "transferring", "introducing" or "transfecting" are used interchangeably herein and relate to the introduction of nucleic acids, in particular exogenous or heterologous nucleic acids, in particular RNA into a cell. According to the present invention, the cell can form part of an organ, a tissue and/or an organism. According to the present invention, the administration of a nucleic acid is either achieved as naked nucleic acid or in combination with an administration reagent. Preferably, administration of nucleic acids is in the form of naked nucleic acids. Preferably, the RNA is administered in combination with stabilizing substances such as RNase inhibitors. The present invention also envisions the repeated introduction of nucleic acids into cells to allow sustained expression for extended time periods.

Cells can be transfected with any carriers with which RNA can be associated, e.g. by forming complexes with the RNA or forming vesicles in which the RNA is enclosed or encapsulated, resulting in increased stability of the RNA compared to naked RNA. Carriers useful according to the invention include, for example, lipid-containing carriers such as cationic lipids, liposomes, in particular cationic liposomes, and micelles, and nanoparticles. Cationic lipids may form complexes with negatively charged nucleic acids. Any cationic lipid may be used according to the invention.

Preferably, the introduction of RNA which encodes a peptide or polypeptide into a cell, in particular into a cell present in vivo, results in expression of said peptide or polypeptide in the cell. In particular embodiments, the targeting of the nucleic acids to particular cells is preferred. In such embodiments, a carrier which is applied for the administration of the nucleic acid to a cell (for example, a retrovirus or a liposome), exhibits a targeting molecule. For example, a molecule such as an antibody which is specific for a surface membrane protein on the target cell or a ligand for a receptor on the target cell may be incorporated into the nucleic acid carrier or may be bound thereto. In case the nucleic acid is administered by liposomes, proteins which bind to a surface membrane protein which is associated with endocytosis may be incorporated into the liposome formulation in order to enable targeting and/or uptake. Such proteins encompass capsid proteins of fragments thereof which are specific for a particular cell type, antibodies against proteins which are internalized, proteins which target an intracellular location etc.

The term "cell" or "host cell" preferably is an intact cell, i.e. a cell with an intact membrane that has not released its normal intracellular components such as enzymes, organelles, or genetic material. An intact cell preferably is a viable cell, i.e. a living cell capable of carrying out its normal metabolic functions. Preferably said term relates according to the invention to any cell which can be transformed or transfected with an exogenous nucleic acid. The term "cell" includes according to the invention prokaryotic cells (e.g., *E. coli*) or eukaryotic cells (e.g., dendritic cells, B cells, CHO cells, COS cells, K562 cells, HEK293 cells, HELA cells, yeast cells, and insect cells). The exogenous nucleic acid may be found inside the cell (i) freely dispersed as such, (ii) incorporated in a recombinant vector, or (iii) integrated into the host cell genome or mitochondrial DNA. Mammalian cells are particularly preferred, such as cells from humans, mice, hamsters, pigs, goats, and primates. The cells may be derived from a large number of tissue types and include primary cells and cell lines. Specific examples include keratinocytes, peripheral blood leukocytes, bone marrow stem cells, and embryonic stem cells. In further embodiments, the cell is an antigen-presenting cell, in particular a dendritic cell, a monocyte, or macrophage.

A cell which comprises a nucleic acid molecule preferably expresses the peptide or polypeptide encoded by the nucleic acid.

The term "clonal expansion" refers to a process wherein a specific entity is multiplied. In the context of the present invention, the term is preferably used in the context of an immunological response in which lymphocytes are stimulated by an antigen, proliferate, and the specific lymphocyte recognizing said antigen is amplified. Preferably, clonal expansion leads to differentiation of the lymphocytes.

Terms such as "reducing" or "inhibiting" relate to the ability to cause an overall decrease, preferably of 5% or greater, 10% or greater, 20% or greater, more preferably of 50% or greater, and most preferably of 75% or greater, in the level. The term "inhibit" or similar phrases includes a complete or essentially complete inhibition, i.e. a reduction to zero or essentially to zero.

Terms such as "increasing", "enhancing", "promoting" or "prolonging" preferably relate to an increase, enhancement, promotion or prolongation by about at least 10%, preferably at least 20%, preferably at least 30%, preferably at least 40%, preferably at least 50%, preferably at least 80%, preferably at least 100%, preferably at least 200% and in particular at least 300%. These terms may also relate to an increase, enhancement, promotion or prolongation from zero or a non-measurable or non-detectable level to a level of more than zero or a level which is measurable or detectable.

The present invention provides vaccines such as cancer vaccines designed on the basis of amino acid modifications or modified peptides predicted as being immunogenic by the methods of the present invention.

According to the invention, the term "vaccine" relates to a pharmaceutical preparation (pharmaceutical composition) or product that upon administration induces an immune response, in particular a cellular immune response, which recognizes and attacks a pathogen or a diseased cell such as a cancer cell. A vaccine may be used for the prevention or treatment of a disease. The term "personalized cancer vaccine" or "individualized cancer vaccine" concerns a particular cancer patient and means that a cancer vaccine is adapted to the needs or special circumstances of an individual cancer patient.

In one embodiment, a vaccine provided according to the invention may comprise a peptide or polypeptide comprising one or more amino acid modifications or one or more modified peptides predicted as being immunogenic by the methods of the invention or a nucleic acid, preferably RNA, encoding said peptide or polypeptide.

The cancer vaccines provided according to the invention when administered to a patent provide one or more T cell epitopes suitable for stimulating, priming and/or expanding T cells specific for the patient's tumor. The T cells are preferably directed against cells expressing antigens from which the T cell epitopes are derived. Thus, the vaccines described herein are preferably capable of inducing or promoting a cellular response, preferably cytotoxic T cell activity, against a cancer disease characterized by presentation of one or more tumor-associated neoantigens with class I MHC. Since a vaccine provided according to the present invention will target cancer specific mutations it will be specific for the patient's tumor.

A vaccine provided according to the invention relates to a vaccine which when administered to a patent preferably provides one or more T cell epitopes, such as 2 or more, 5 or more, 10 or more, 15 or more, 20 or more, 25 or more, 30 or more and preferably up to 60, up to 55, up to 50, up to 45, up to 40, up to 35 or up to 30 T cell epitopes, incorporating amino acid modifications or modified peptides predicted as being immunogenic by the methods of the invention. Such T cell epitopes are also termed "neo-epitopes" herein. Presentation of these epitopes by cells of a patient, in particular antigen presenting cells, preferably results in T cells targeting the epitopes when bound to MHC and thus, the patient's tumor, preferably the primary tumor as well as tumor metastases, expressing antigens from which the T cell epitopes are derived and presenting the same epitopes on the surface of the tumor cells.

The methods of the invention may comprise the further step of determining the usability of the identified amino acid modifications or modified peptides for cancer vaccination.

Thus further steps can involve one or more of the following: (i) assessing whether the modifications are located in known or predicted MHC presented epitopes, (ii) in vitro and/or in silico testing whether the modifications are located in MHC presented epitopes, e.g. testing whether the modifications are part of peptide sequences which are processed into and/or presented as MHC presented epitopes, and (iii) in vitro testing whether the envisaged modified epitopes, in particular when present in their natural sequence context, e.g. when flanked by amino acid sequences also flanking said epitopes in the naturally occurring protein, and when expressed in antigen presenting cells are able to stimulate T cells such as T cells of the patient having the desired specificity. Such flanking sequences each may comprise 3 or more, 5 or more, 10 or more, 15 or more, 20 or more and preferably up to 50, up to 45, up to 40, up to 35 or up to 30 amino acids and may flank the epitope sequence N-terminally and/or C-terminally.

Modified peptides determined according to the invention may be ranked for their usability as epitopes for cancer vaccination. Thus, in one aspect, the method of the invention comprises a manual or computer-based analytical process in which the identified modified peptides are analyzed and selected for their usability in the respective vaccine to be provided. In a preferred embodiment, said analytical process is a computational algorithm-based process. Preferably, said analytical process comprises determining and/or ranking epitopes according to a prediction of their capacity of being immunogenic.

The neo-epitopes identified according to the invention and provided by a vaccine of the invention are preferably present in the form of a polypeptide comprising said neo-epitopes such as a polyepitopic polypeptide or a nucleic acid, in particular RNA, encoding said polypeptide. Furthermore, the neo-epitopes may be present in the polypeptide in the form of a vaccine sequence, i.e. present in their natural sequence context, e.g. flanked by amino acid sequences also flanking said epitopes in the naturally occurring protein. Such flanking sequences each may comprise 5 or more, 10 or more, 15 or more, 20 or more and preferably up to 50, up to 45, up to 40, up to 35 or up to 30 amino acids and may flank the epitope sequence N-terminally and/or C-terminally. Thus, a vaccine sequence may comprise 20 or more, 25 or more, 30 or more, 35 or more, 40 or more and preferably up to 50, up to 45, up to 40, up to 35 or up to 30 amino acids. In one embodiment, the neo-epitopes and/or vaccine sequences are lined up in the polypeptide head-to-tail.

In one embodiment, the neo-epitopes and/or vaccine sequences are spaced by linkers, in particular neutral linkers. The term "linker" according to the invention relates to a peptide added between two peptide domains such as epitopes or vaccine sequences to connect said peptide domains. There is no particular limitation regarding the linker sequence. However, it is preferred that the linker sequence reduces steric hindrance between the two peptide domains, is well translated, and supports or allows processing of the epitopes. Furthermore, the linker should have no or only little immunogenic sequence elements. Linkers preferably should not create non-endogenous neo-epitopes like those generated from the junction suture between adjacent neo-epitopes, which might generate unwanted immune reactions. Therefore, the polyepitopic vaccine should preferably contain linker sequences which are able to reduce the number of unwanted MHC binding junction epitopes. Hoyt et al. (*EMBO J.* 25(8), 1720-9, 2006) and Zhang et al. (*J. Biol. Chem.*, 279(10), 8635-41, 2004) have shown that glycine-rich sequences impair proteasomal processing and thus the use of glycine rich linker sequences act to minimize the number of linker-contained peptides that can be processed by the proteasome. Furthermore, glycine was observed to inhibit a strong binding in MHC binding groove positions (Abastado et al., *J. Immunol.* 151(7), 3569-75, 1993). Schlessinger et al. (*Proteins,* 61(1), 115-26, 2005) had found that amino acids glycine and serine included in an amino acid sequence result in a more flexible protein that is more efficiently translated and processed by the proteasome, enabling better access to the encoded neo-epitopes. The linker each may comprise 3 or more, 6 or more, 9 or more, 10 or more, 15 or more, 20 or more and preferably up to 50, up to 45, up to 40, up to 35 or up to 30 amino acids. Preferably the linker is enriched in glycine and/or serine amino acids. Preferably, at least 50%, at least 60%, at least 70%, at least 80%, at least 90%, or at least 95% of the amino acids of the linker are glycine and/or serine. In one preferred embodiment, a linker is substantially composed of the amino acids glycine and serine. In one embodiment, the linker comprises the amino acid sequence $(GGS)_a(GSS)_b(GGG)_c(SSG)_d(GSG)_e$ wherein a, b, c, d and e is independently a number selected from 0, 1, 2, 3, 4, 5, 6, 7, 8, 9, 10, 11, 12, 13, 14, 15, 16, 17, 18, 19, or 20 and wherein a+b+c+d+e are different from 0 and preferably are 2 or more, 3 or more, 4 or more or 5 or more. In one embodiment, the linker comprises a sequence as described herein including the linker sequences described in the examples such as the sequence GGSGGGGSG.

In one particularly preferred embodiment, a polypeptide incorporating one or more neo-epitopes such as a polyepitopic polypeptide according to the present invention is administered to a patient in the form of a nucleic acid, preferably RNA such as in vitro transcribed or synthetic RNA, which may be expressed in cells of a patient such as antigen presenting cells to produce the polypeptide. The present invention also envisions the administration of one or more multiepitopic polypeptides which for the purpose of the present invention are comprised by the term "polyepitopic polypeptide", preferably in the form of a nucleic acid, preferably RNA such as in vitro transcribed or synthetic RNA, which may be expressed in cells of a patient such as antigen presenting cells to produce the one or more polypeptides. In the case of an administration of more than one multiepitopic polypeptide the neo-epitopes provided by the different multiepitopic polypeptides may be different or partially overlapping. Once present in cells of a patient such as antigen presenting cells the polypeptide according to the invention is processed to produce the neo-epitopes identified according to the invention. Administration of a vaccine provided according to the invention may provide MHC class II-presented epitopes that are capable of eliciting a CD4+ helper T cell response against cells expressing antigens from which the MHC presented epitopes are derived. Alternatively or additionally, administration of a vaccine provided according to the invention may provide MHC class I-presented epitopes that are capable of eliciting a CD8+ T cell response against cells expressing antigens from which the MHC presented epitopes are derived. Furthermore, administration of a vaccine provided according to the invention may provide one or more neo-epitopes (including known neo-epitopes and neo-epitopes identified according to the invention) as well as one or more epitopes not containing cancer specific somatic mutations but being expressed by cancer cells and preferably inducing an immune response against cancer cells, preferably a cancer specific immune response. In one embodiment, administration of a vaccine provided according to the invention provides neo-epitopes that are MHC class II-presented epitopes and/or are capable of eliciting a CD4+ helper T cell response against cells expressing antigens from which the MHC presented epitopes are derived as well as epitopes not containing cancer-specific somatic mutations that are MHC class I-presented epitopes and/or are capable of eliciting a CD8+ T cell response against cells expressing antigens from which the MHC presented epitopes are derived. In one embodiment, the epitopes not containing cancer-specific somatic mutations are derived from a tumor antigen. In one embodiment, the neo-epitopes and epitopes not containing cancer-specific somatic mutations have a synergistic effect in the treatment of cancer. Preferably, a vaccine provided according to the invention is useful for polyepitopic stimulation of cytotoxic and/or helper T cell responses.

The vaccine provided according to the invention may be a recombinant vaccine.

The term "recombinant" in the context of the present invention means "made through genetic engineering". Preferably, a "recombinant entity" such as a recombinant polypeptide in the context of the present invention is not occurring naturally, and preferably is a result of a combination of entities such as amino acid or nucleic acid sequences which are not combined in nature. For example, a recombinant polypeptide in the context of the present invention may contain several amino acid sequences such as neo-epitopes or vaccine sequences derived from different proteins or different portions of the same protein fused together, e.g., by peptide bonds or appropriate linkers.

The term "naturally occurring" as used herein refers to the fact that an object can be found in nature. For example, a peptide or nucleic acid that is present in an organism (including viruses) and can be isolated from a source in nature and which has not been intentionally modified by man in the laboratory is naturally occurring.

Agents, compositions and methods described herein can be used to treat a subject with a disease, e.g., a disease characterized by the presence of diseased cells expressing an antigen and presenting a fragment thereof. Particularly preferred diseases are cancer diseases. Agents, compositions and methods described herein may also be used for immunization or vaccination to prevent a disease described herein.

According to the invention, the term "disease" refers to any pathological state, including cancer diseases, in particular those fauns of cancer diseases described herein.

The term "normal" refers to the healthy state or the conditions in a healthy subject or tissue, i.e., non-pathological conditions, wherein "healthy" preferably means non-cancerous.

"Disease involving cells expressing an antigen" means according to the invention that expression of the antigen in cells of a diseased tissue or organ is detected. Expression in cells of a diseased tissue or organ may be increased compared to the state in a healthy tissue or organ. An increase refers to an increase by at least 10%, in particular at least 20%, at least 50%, at least 100%, at least 200%, at least 500%, at least 1000%, at least 10000% or even more. In one embodiment, expression is only found in a diseased tissue, while expression in a healthy tissue is repressed. According to the invention, diseases involving or being associated with cells expressing an antigen include cancer diseases.

According to the invention, the term "tumor" or "tumor disease" refers to an abnormal growth of cells (called neoplastic cells, tumorigenous cells or tumor cells) preferably forming a swelling or lesion. By "tumor cell" is meant an abnormal cell that grows by a rapid, uncontrolled cellular proliferation and continues to grow after the stimuli that initiated the new growth cease. Tumors show partial or complete lack of structural organization and functional coordination with the normal tissue, and usually form a distinct mass of tissue, which may be either benign, pre-malignant or malignant.

Cancer (medical term: malignant neoplasm) is a class of diseases in which a group of cells display uncontrolled growth (division beyond the normal limits), invasion (intrusion on and destruction of adjacent tissues), and sometimes metastasis (spread to other locations in the body via lymph or blood). These three malignant properties of cancers differentiate them from benign tumors, which are self-limited, and do not invade or metastasize. Most cancers form a tumor but some, like leukemia, do not. Malignancy, malignant neoplasm, and malignant tumor are essentially synonymous with cancer.

Neoplasm is an abnormal mass of tissue as a result of neoplasia. Neoplasia (new growth in Greek) is the abnormal proliferation of cells. The growth of the cells exceeds, and is uncoordinated with that of the normal tissues around it. The growth persists in the same excessive manner even after cessation of the stimuli. It usually causes a lump or tumor. Neoplasms may be benign, pre-malignant or malignant.

"Growth of a tumor" or "tumor growth" according to the invention relates to the tendency of a tumor to increase its size and/or to the tendency of tumor cells to proliferate.

For purposes of the present invention, the terms "cancer" and "cancer disease" are used interchangeably with the terms "tumor" and "tumor disease".

Cancers are classified by the type of cell that resembles the tumor and, therefore, the tissue presumed to be the origin of the tumor. These are the histology and the location, respectively.

The term "cancer" according to the invention comprises carcinomas, adenocarcinomas, blastomas, leukemias, seminomas, melanomas, teratomas, lymphomas, neuroblastomas, gliomas, rectal cancer, endometrial cancer, kidney cancer, adrenal cancer, thyroid cancer, blood cancer, skin cancer, cancer of the brain, cervical cancer, intestinal cancer, liver cancer, colon cancer, stomach cancer, intestine cancer, head and neck cancer, gastrointestinal cancer, lymph node cancer, esophagus cancer, colorectal cancer, pancreas cancer, ear, nose and throat (ENT) cancer, breast cancer, prostate cancer, cancer of the uterus, ovarian cancer and lung cancer and the metastases thereof. Examples thereof are lung carcinomas, mamma carcinomas, prostate carcinomas, colon carcinomas, renal cell carcinomas, cervical carcinomas, or metastases of the cancer types or tumors described above. The term cancer according to the invention also comprises cancer metastases and relapse of cancer.

By "metastasis" is meant the spread of cancer cells from its original site to another part of the body. The formation of metastasis is a very complex process and depends on detachment of malignant cells from the primary tumor, invasion of the extracellular matrix, penetration of the endothelial basement membranes to enter the body cavity and vessels, and then, after being transported by the blood, infiltration of target organs. Finally, the growth of a new tumor, i.e. a secondary tumor or metastatic tumor, at the target site depends on angiogenesis. Tumor metastasis often occurs even after the removal of the primary tumor because tumor cells or components may remain and develop metastatic potential. In one embodiment, the term "metastasis" according to the invention relates to "distant metastasis" which relates to a metastasis which is remote from the primary tumor and the regional lymph node system.

The cells of a secondary or metastatic tumor are like those in the original tumor. This means, for example, that, if ovarian cancer metastasizes to the liver, the secondary tumor is made up of abnormal ovarian cells, not of abnormal liver cells. The tumor in the liver is then called metastatic ovarian cancer, not liver cancer.

The term "circulating tumor cells" or "CTCs" relates to cells that have detached from a primary tumor or tumor metastases and circulate in the bloodstream. CTCs may constitute seeds for subsequent growth of additional tumors (metastasis) in different tissues. Circulating tumor cells are found in frequencies in the order of 1-10 CTC per mL of whole blood in patients with metastatic disease. Research methods have been developed to isolate CTC. Several research methods have been described in the art to isolate CTCs, e.g. techniques which use of the fact that epithelial cells commonly express the cell adhesion protein EpCAM, which is absent in normal blood cells. Immunomagnetic bead-based capture involves treating blood specimens with antibody to EpCAM that has been conjugated with magnetic particles, followed by separation of tagged cells in a magnetic field. Isolated cells are then stained with antibody to another epithelial marker, cytokeratin, as well as a common leukocyte marker CD45, so as to distinguish rare CTCs from contaminating white blood cells. This robust and semi-automated approach identifies CTCs with an average yield of approximately 1 CTC/mL and a purity of 0.1% (Allard et al., 2004: Clin Cancer Res 10, 6897-6904). A second method for isolating CTCs uses a microfluidic-based CTC capture device which involves flowing whole blood through a chamber embedded with 80,000 microposts that have been rendered functional by coating with antibody to EpCAM. CTCs are then stained with secondary antibodies against either cytokeratin or tissue specific markers, such as PSA in prostate cancer or HER2 in breast cancer and are visualized by automated scanning of microposts in multiple planes along three dimensional coordinates. CTC-chips are able to identifying cytokerating-positive circulating tumor cells in patients with a median yield of 50 cells/mi and purity ranging from 1-80% (Nagrath et al., 2007: Nature 450, 1235-1239). Another possibility for isolating CTCs is using the CellSearch™ Circulating Tumor Cell (CTC) Test from Veridex, LLC (Raritan, N.J.) which captures, identifies, and counts CTCs in a tube of blood. The CellSearch™ system is a U.S. Food and Drug Administration (FDA) approved methodology for enumeration of CTC in whole blood which is based on a combination of immunomagnetic labeling and automated digital microscopy. There are other methods for isolating CTCs described in the literature all of which can be used in conjunction with the present invention.

A relapse or recurrence occurs when a person is affected again by a condition that affected them in the past. For example, if a patient has suffered from a tumor disease, has received a successful treatment of said disease and again develops said disease said newly developed disease may be considered as relapse or recurrence. However, according to the invention, a relapse or recurrence of a tumor disease may but does not necessarily occur at the site of the original tumor disease. Thus, for example, if a patient has suffered from ovarian tumor and has received a successful treatment a relapse or recurrence may be the occurrence of an ovarian tumor or the occurrence of a tumor at a site different to ovary. A relapse or recurrence of a tumor also includes situations wherein a tumor occurs at a site different to the site of the original tumor as well as at the site of the original tumor. Preferably, the original tumor for which the patient has received a treatment is a primary tumor and the tumor at a site different to the site of the original tumor is a secondary or metastatic tumor.

By "treat" is meant to administer a compound or composition as described herein to a subject in order to prevent or eliminate a disease, including reducing the size of a tumor or the number of tumors in a subject; arrest or slow a disease in a subject; inhibit or slow the development of a new disease in a subject; decrease the frequency or severity of symptoms and/or recurrences in a subject who currently has or who previously has had a disease; and/or prolong, i.e. increase the lifespan of the subject. In particular, the term "treatment of a disease" includes curing, shortening the duration, ameliorating, preventing, slowing down or inhibiting progression or worsening, or preventing or delaying the onset of a disease or the symptoms thereof.

By "being at risk" is meant a subject, i.e. a patient, that is identified as having a higher than normal chance of developing a disease, in particular cancer, compared to the general population. In addition, a subject who has had, or who currently has, a disease, in particular cancer, is a subject who has an increased risk for developing a disease, as such a subject may continue to develop a disease. Subjects who currently have, or who have had, a cancer also have an increased risk for cancer metastases.

The term "immunotherapy" relates to a treatment involving activation of a specific immune reaction. In the context of the present invention, terms such as "protect", "prevent", "prophylactic", "preventive", or "protective" relate to the prevention or treatment or both of the occurrence and/or the propagation of a disease in a subject and, in particular, to minimizing the chance that a subject will develop a disease or to delaying the development of a disease. For example, a person at risk for a tumor, as described above, would be a candidate for therapy to prevent a tumor.

A prophylactic administration of an immunotherapy, for example, a prophylactic administration of a vaccine of the invention, preferably protects the recipient from the development of a disease.

A therapeutic administration of an immunotherapy, for example, a therapeutic administration of a vaccine of the invention, may lead to the inhibition of the progress/growth of the disease. This comprises the deceleration of the progress/growth of the disease, in particular a disruption of the progression of the disease, which preferably leads to elimination of the disease.

Immunotherapy may be performed using any of a variety of techniques, in which agents provided herein function to remove diseased cells from a patient. Such removal may take place as a result of enhancing or inducing an immune response in a patient specific for an antigen or a cell expressing an antigen.

Within certain embodiments, immunotherapy may be active immunotherapy, in which treatment relies on the in vivo stimulation of the endogenous host immune system to react against diseased cells with the administration of immune response-modifying agents (such as polypeptides and nucleic acids as provided herein).

The agents and compositions provided herein may be used alone or in combination with conventional therapeutic regimens such as surgery, irradiation, chemotherapy and/or bone marrow transplantation (autologous, syngeneic, allogeneic or unrelated).

The term "immunization" or "vaccination" describes the process of treating a subject with the purpose of inducing an immune response for therapeutic or prophylactic reasons.

The term "in vivo" relates to the situation in a subject.

The terms "subject", "individual", "organism" or "patient" are used interchangeably and relate to vertebrates, preferably mammals. For example, mammals in the context of the present invention are humans, non-human primates, domesticated animals such as dogs, cats, sheep, cattle, goats, pigs, horses etc., laboratory animals such as mice, rats, rabbits, guinea pigs, etc. as well as animals in captivity such as animals of zoos. The teen "animal" as used herein also includes humans. The term "subject" may also include a patient, i.e., an animal, preferably a human having a disease, preferably a disease as described herein.

The term "autologous" is used to describe anything that is derived from the same subject. For example, "autologous transplant" refers to a transplant of tissue or organs derived from the same subject. Such procedures are advantageous because they overcome the immunological barrier which otherwise results in rejection.

The term "heterologous" is used to describe something consisting of multiple different elements. As an example, the transfer of one individual's bone marrow into a different individual constitutes a heterologous transplant. A heterologous gene is a gene derived from a source other than the subject.

As part of the composition for an immunization or a vaccination, preferably one or more agents as described herein are administered together with one or more adjuvants for inducing an immune response or for increasing an immune response. The term "adjuvant" relates to compounds which prolongs or enhances or accelerates an immune response. The composition of the present invention preferably exerts its effect without addition of adjuvants. Still, the composition of the present application may contain any known adjuvant. Adjuvants comprise a heterogeneous group of compounds such as oil emulsions (e.g., Freund's adjuvants), mineral compounds (such as alum), bacterial products (such as *Bordetella pertussis* toxin), liposomes, and immune-stimulating complexes. Examples for adjuvants are monophosphoryl-lipid-A (MPL SmithKline Beecham). Saponins such as QS21 (SmithKline Beecham), DQS21 (SmithKline Beecham; WO 96/33739), QS7, QS17, QS18, and QS-L1 (So et al., 1997, Mol. Cells 7: 178-186), incomplete Freund's adjuvants, complete Freund's adjuvants, vitamin E, montanid, alum, CpG oligonucleotides (Krieg et al., 1995, Nature 374: 546-549), and various water-in-oil emulsions which are prepared from biologically degradable oils such as squalene and/or tocopherol.

Other substances which stimulate an immune response of the patient may also be administered. It is possible, for example, to use cytokines in a vaccination, owing to their regulatory properties on lymphocytes. Such cytokines comprise, for example, interleukin-12 (IL-12) which was shown to increase the protective actions of vaccines (cf. *Science* 268:1432-1434, 1995), GM-CSF and IL-18.

There are a number of compounds which enhance an immune response and which therefore may be used in a vaccination. Said compounds comprise co-stimulating molecules provided in the form of proteins or nucleic acids such as B7-1 and B7-2 (CD80 and CD86, respectively).

According to the invention, a bodily sample may be a tissue sample, including body fluids, and/or a cellular sample. Such bodily samples may be obtained in the conventional manner such as by tissue biopsy, including punch biopsy, and by taking blood, bronchial aspirate, sputum, urine, feces or other body fluids. According to the invention, the term "sample" also includes processed samples such as fractions or isolates of biological samples, e.g. nucleic acid or cell isolates.

The agents such as vaccines and compositions described herein may be administered via any conventional route, including by injection or infusion. The administration may be carried out, for example, orally, intravenously, intraperitoneally, intramuscularly, subcutaneously or transdermally. In one embodiment, administration is carried out intranodally such as by injection into a lymph node. Other forms of administration envision the in vitro transfection of antigen presenting cells such as dendritic cells with nucleic acids described herein followed by administration of the antigen presenting cells.

The agents described herein are administered in effective amounts. An "effective amount" refers to the amount which achieves a desired reaction or a desired effect alone or together with further doses. In the case of treatment of a particular disease or of a particular condition, the desired reaction preferably relates to inhibition of the course of the disease. This comprises slowing down the progress of the disease and, in particular, interrupting or reversing the progress of the disease. The desired reaction in a treatment of a disease or of a condition may also be delay of the onset or a prevention of the onset of said disease or said condition.

An effective amount of an agent described herein will depend on the condition to be treated, the severeness of the disease, the individual parameters of the patient, including age, physiological condition, size and weight, the duration of treatment, the type of an accompanying therapy (if present), the specific route of administration and similar factors. Accordingly, the doses administered of the agents described herein may depend on various of such parameters. In the case that a reaction in a patient is insufficient with an initial dose, higher doses (or effectively higher doses achieved by a different, more localized route of administration) may be used.

The pharmaceutical compositions described herein are preferably sterile and contain an effective amount of the therapeutically active substance to generate the desired reaction or the desired effect.

The pharmaceutical compositions described herein are generally administered in pharmaceutically compatible amounts and in pharmaceutically compatible preparation. The term "pharmaceutically compatible" refers to a nontoxic material which does not interact with the action of the active component of the pharmaceutical composition. Preparations of this kind may usually contain salts, buffer substances, preservatives, carriers, supplementing immunity-enhancing substances such as adjuvants, e.g. CpG oligonucleotides, cytokines, chemokines, saponin, GM-CSF and/or RNA and, where appropriate, other therapeutically active compounds. When used in medicine, the salts should be pharmaceutically compatible. However, salts which are not pharmaceutically compatible may used for preparing pharmaceutically compatible salts and are included in the invention. Pharmacologically and pharmaceutically compatible salts of this kind comprise in a non-limiting way those prepared from the following acids: hydrochloric, hydrobromic, sulfuric, nitric, phosphoric, maleic, acetic, salicylic, citric, formic, malonic, succinic acids, and the like. Pharmaceutically compatible salts may also be prepared as alkali metal salts or alkaline earth metal salts, such as sodium salts, potassium salts or calcium salts.

A pharmaceutical composition described herein may comprise a pharmaceutically compatible carrier. The term "carrier" refers to an organic or inorganic component, of a natural or synthetic nature, in which the active component is combined in order to facilitate application. According to the invention, the term "pharmaceutically compatible carrier" includes one or more compatible solid or liquid fillers, diluents or encapsulating substances, which are suitable for administration to a patient. The components of the pharmaceutical composition of the invention are usually such that no interaction occurs which substantially impairs the desired pharmaceutical efficacy.

The pharmaceutical compositions described herein may contain suitable buffer substances such as acetic acid in a salt, citric acid in a salt, boric acid in a salt and phosphoric acid in a salt.

The pharmaceutical compositions may, where appropriate, also contain suitable preservatives such as benzalkonium chloride, chlorobutanol, paraben and thimerosal.

The pharmaceutical compositions are usually provided in a uniform dosage form and may be prepared in a manner known per se. Pharmaceutical compositions of the invention may be in the form of capsules, tablets, lozenges, solutions, suspensions, syrups, elixirs or in the form of an emulsion, for example.

Compositions suitable for parenteral administration usually comprise a sterile aqueous or nonaqueous preparation of the active compound, which is preferably isotonic to the blood of the recipient. Examples of compatible carriers and solvents are Ringer solution and isotonic sodium chloride solution. In addition, usually sterile, fixed oils are used as solution or suspension medium.

The present invention is described in detail by the figures and examples below, which are used only for illustration purposes and are not meant to be limiting. Owing to the description and the examples, further embodiments which are likewise included in the invention are accessible to the skilled worker.

FIGURES

FIG. 1. MHC binding prediction overview

Figure 2:
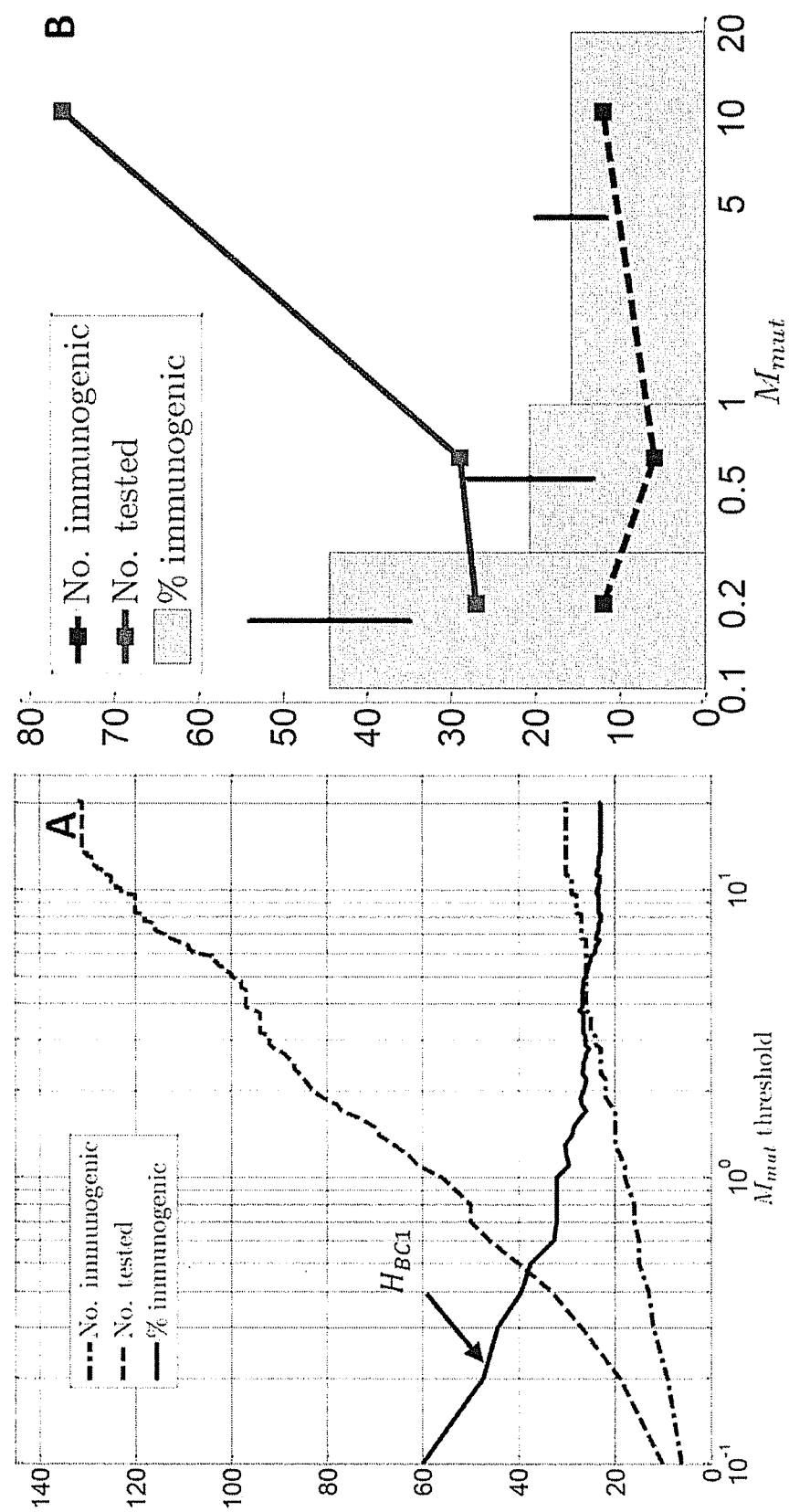

FIG. 2. Analysis of immunogenicity as a function of the $M_{mut}$ score for 50 prioritized B16F10 mutations and 82 prioritized CT26.WT mutations (132 mutations in total), of which 30 were immunogenic. All vaccinations were performed with RNA. For B16F10 immunogenicity was assayed by challenging BMDCs with RNA and measuring the immune response of splenocytes with ELISPOT and FACS. For CT26.WT immunogenicity was assayed by challenging BMDCs with RNA and peptides separately and measuring the immune response of splenocytes with ELISPOT; a mutation was considered immunogenic if either peptide or RNA registered an immune response. A Cumulative distribution of immunogenic mutations as a function of the $M_{mut}$ score. The graph shows the total number of mutations below a given $M_{mut}$ score (red), of these, the number of mutations that were immunogenic (blue), and the percent of immunogenic mutations from the total (black). B Histogram of percent of immunogenic mutations per $M_{mut}$ bin for the following ranges: ≤0.3, (0.3, 1], >1. Errors shown are standard errors.

Figure 3:
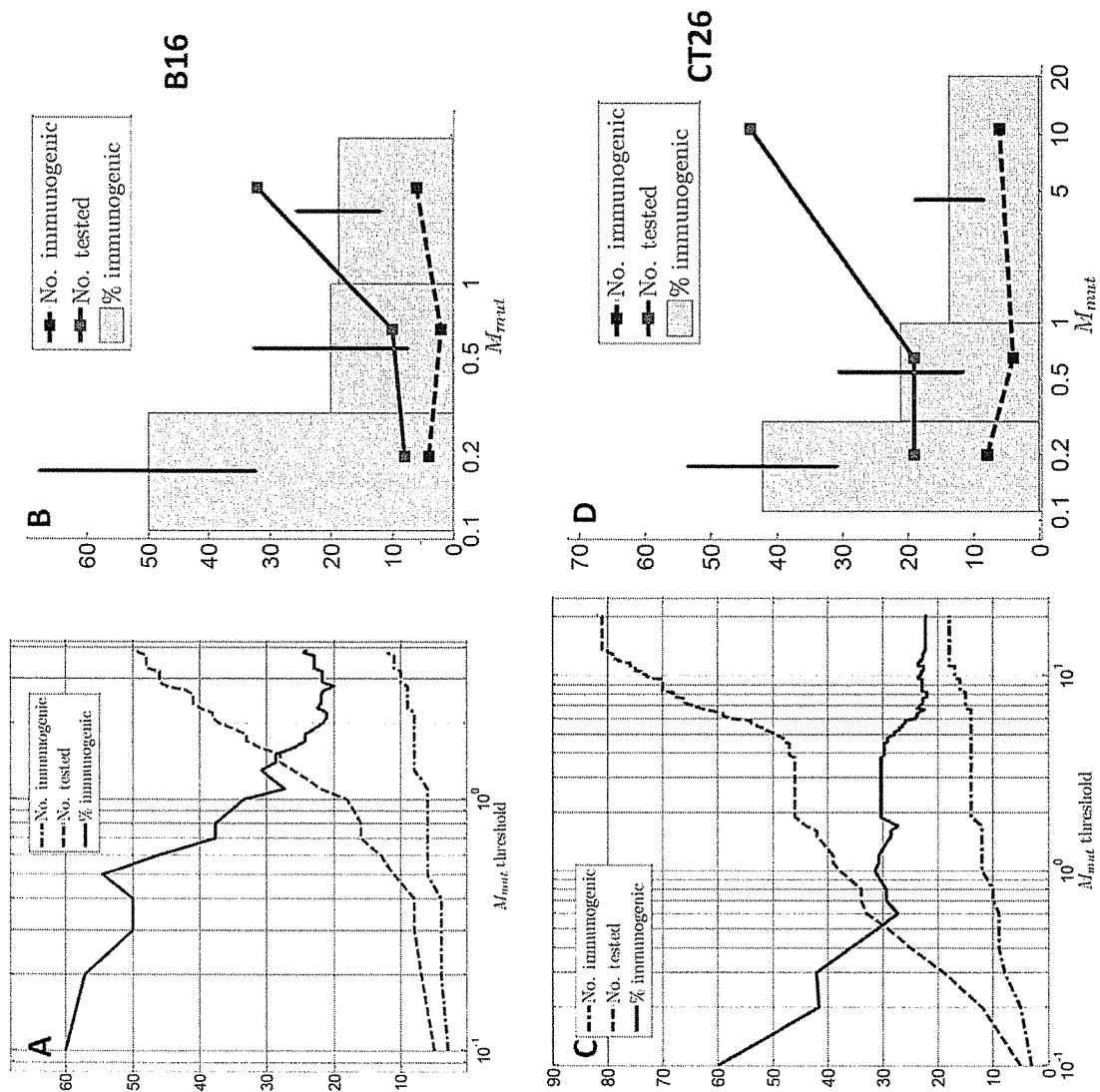

FIG. 3. Analysis of B16F10 and CT26.WT immunogenicity as a function of $M_{mut}$. Cumulative distribution of immunogenic mutations as a function of the $M_{mut}$ score for B 16 (A) and CT26 (C). Histogram of percent of immunogenic mutations per $M_{mut}$ bin for the following ranges: [0.1, 0.3], (0.3, 1], (1,∞) for B16 (B) and CT26 (D). Figures A and B are based on analysis of 50 B16F10 prioritized mutations, of which 12 were immunogenic. Figures C and D are based on analysis of 82 B16F10 prioritized mutations, of which 30 were immunogenic. For more details see legend of FIG. 2. Errors are standard errors.

Figure 4:
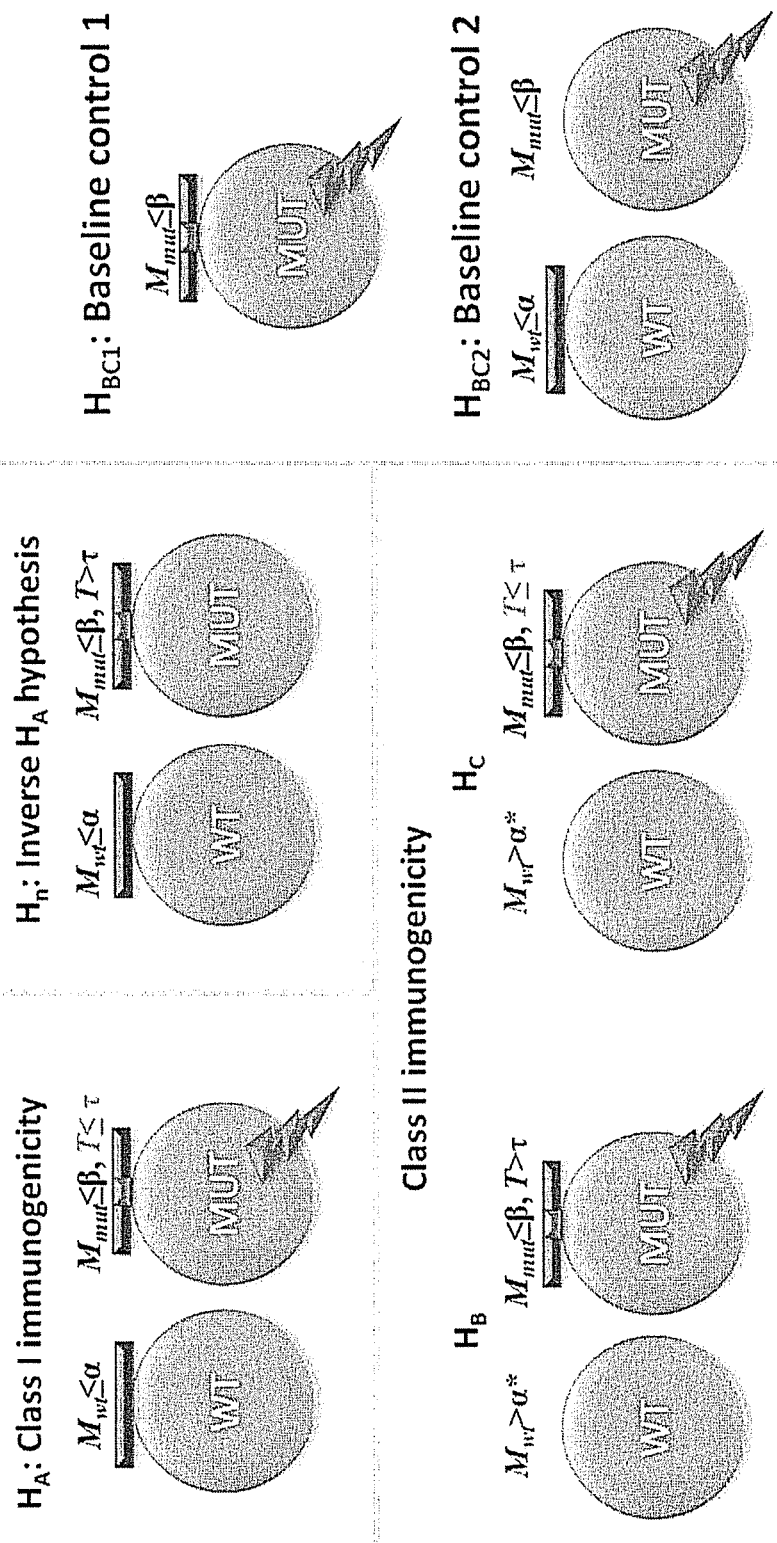

FIG. 4. Models of immunogenicity and control hypotheses. Class I immunogenicity, denoted by $H_A$, makes the assumption that both the WT and MUT epitopes are presented by cells, and that the mutation sufficiency altered the physico-chemical properties of the amino acid so that the immune system registers this change and generates an immune response (denoted by the lightning bolt). The $H_n$ hypothesis, serving as a control for $H_A$, is simply the inverted $H_A$ hypothesis, namely, that the mutation did not significantly alter the physico-chemical properties of the amino acid and therefore has a lower likelihood of being "detected" by the immune system and generating an immune response. In class II immunogenicity ($H_B \cup H_C$) the WT epitope is not presented but the MUT epitope is presented. $H_B$ and $H_C$ are distinguished by high (T>τ) versus low (T≤τ) T scores, respectively. Note that for $\alpha^*=\alpha$, the $H_{BC1}$ model for immunogenicity ($M_{mut}<\beta$) is a composite of all four groups: $H_{BC1}=U[H_A, H_B, H_C, H_n]$.

Figure 5:
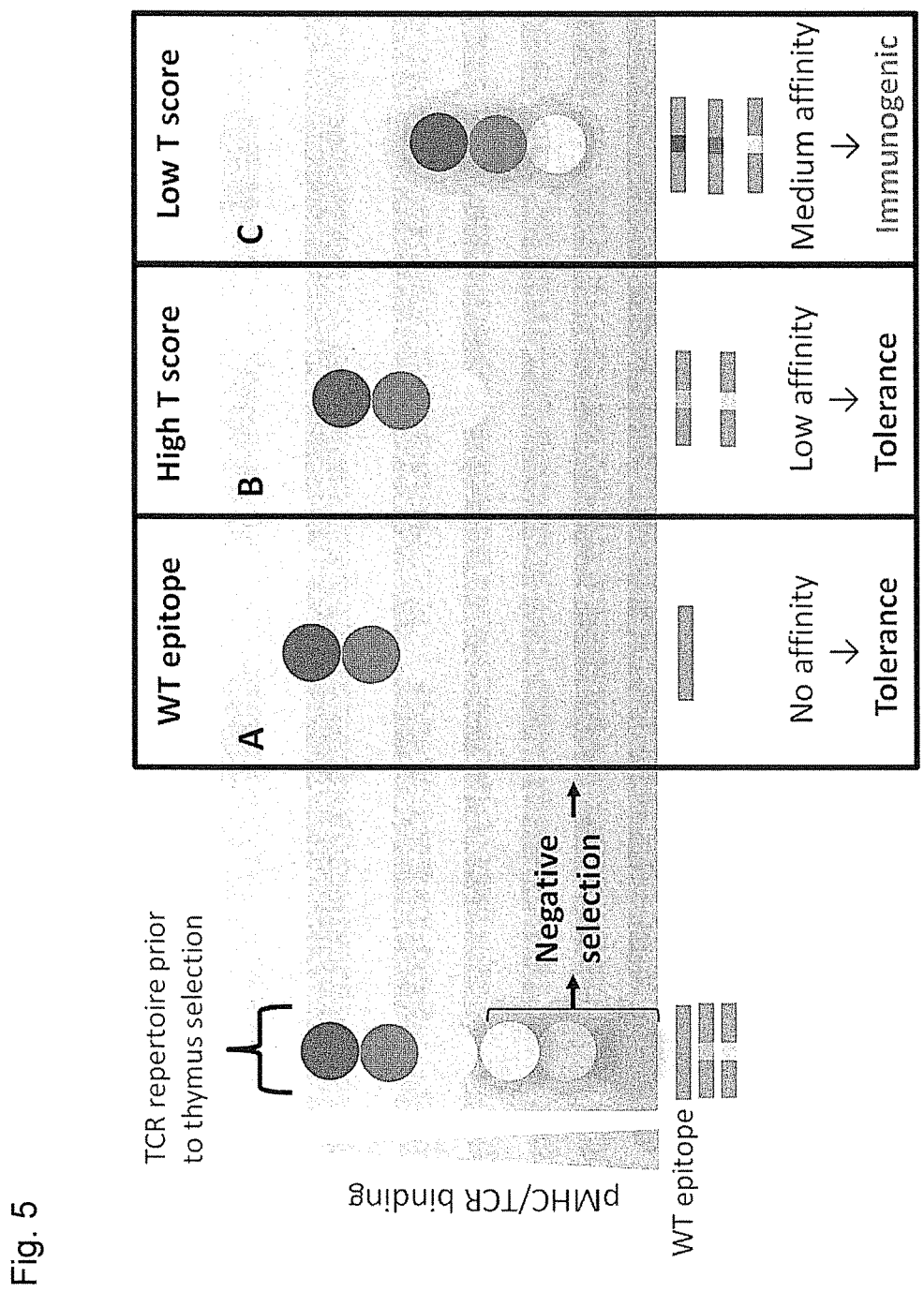

FIG. 5. Hypothesized relation of the T score to immunogenincity. According to the class I immunogenicity model, during T cell development TCRs that bound strongly to the wild type epitope were deleted. Extant TCRs should exhibit only weak or no binding affinity to the wild type epitope (A). Epitopes that contain an amino acid substituion that has a high T score have similar physico-chemical properties to the wild type amino acid and therefore will likely have little impact on the binding affinity to extant TCRs (B). Epitopes that contain an amino acid substituion with a T score have a greater chance to increase the binding affinity to exact TCRs and therefore a greater likelihood to be immunogenic (C). In this schematic illustration, color coding is used to pair T cells with a matching peptide. Orange/yellow mutations represent mutations with high T scores (similar to the WT), where as blue/purple mutiations represent mutations with low T scores (significant physico-chemical difference compared to the WT).

Figure 6:
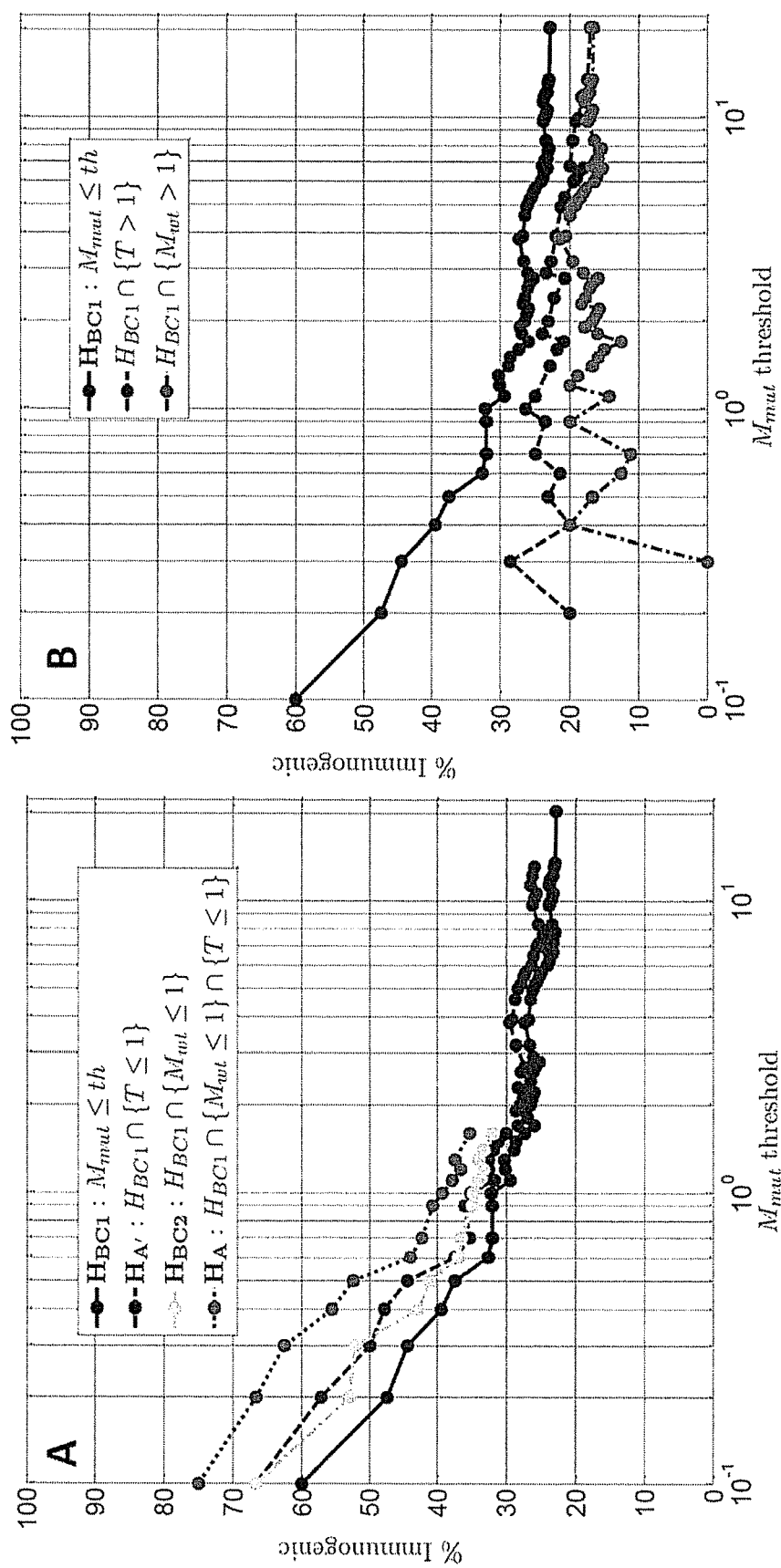

FIG. 6. Cumulative distribution of immunogenic mutations as a function of $M_{mut}$. A Comparison of the percent of immunogenic mutations that satisfy the baseline control hypothesis $H_{BC1}$: $\{M_{mut} \leq \beta\}$, with the percent of immunogenic mutations that satisfy the partial hypothesis $H_A$: $H_{BC1} \cap \{T \leq \tau\}$, the partial hypothesis $H_{BC2}$: $H_{BC1} \cap \{M_{mut} \leq \alpha\}$ and the full hypothesis $H_A$: $H_{BC1} \cap \{M_{mut} \leq \alpha\} \cap \{T \leq \tau\}$, for $\alpha=1$, $\tau=1$. B Comparison of the percent of immunogenic mutations that satisfy the baseline control hypotheses $H_{BC1}$: $\{M_{mut} \leq \beta\}$ with the percent of immunogenic mutations that satisfy the inverse partial hypotheses: $H_{BC1} \cap \{T > \tau\}$ and $H_{BC1} \cap \{M_{mut} > \alpha\}$. The analysis in A and B are based on the pooled B16F10 and CT26.WT datasets, comprising of 132 mutations, of which 30 were immunogenic. Each data point in the graphs is based on ≥4 mutations.

Figure 7:
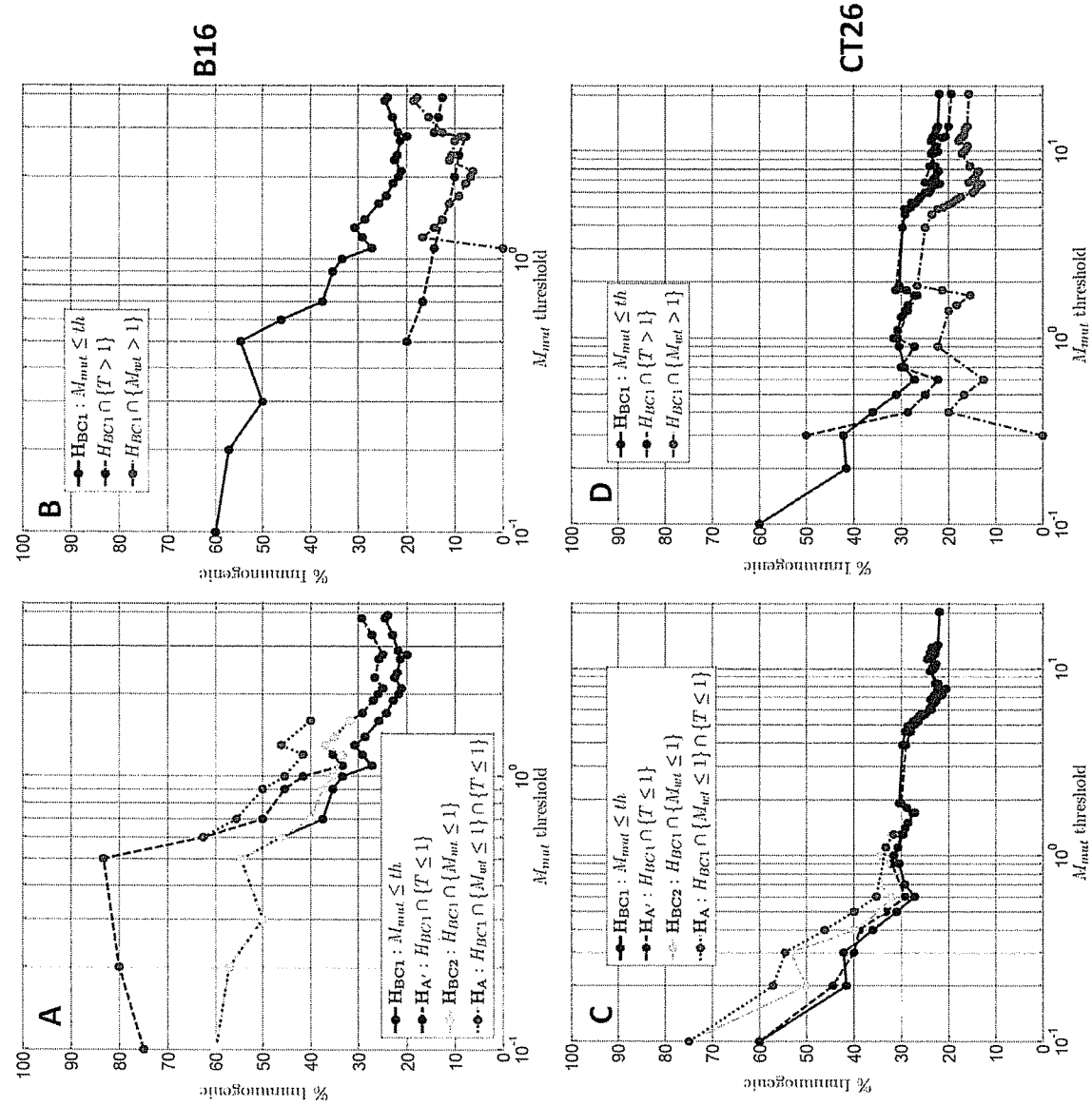

FIG. 7. Cumulative distribution of immunogenic mutations as a function of the $M_{mut}$ score. Comparison of the percent of immunogenic mutations that satisfy the baseline control hypothesis $H_{BC1}$: $\{M_{mut} \leq \beta\}$, with the percent of immunogenic mutations that satisfy the partial hypothesis $H_A$: $H_{BC1} \cap \{T \leq \tau\}$, the partial hypothesis $H_{BC2}$: $H_{BC1} \cap \{M_{mut} \leq \alpha\}$ and the full hypothesis $H_A$: $H_{BC1} \cap \{M_{mut} \leq \alpha\} \cap \{T \leq \tau\}$, given $\alpha=1$, $\tau=1$ for B16 (A) and CT26 (C). Comparison of the percent of immunogenic mutations that satisfy the baseline control hypotheses $H_{BC1}$: $\{M_{mut} \leq \beta\}$ with the percent of immunogenic mutations that satisfy the inverse partial hypotheses: $H_{BC1} \cap \{T>\tau\}$ and $H_{BC1} \cap \{M_{mut}>\alpha\}$ for B16 (B) and CT26 (D). Figures A and B are based on analysis of the 50 B16F10 prioritized mutations, of which 12 were immunogenic. Figures C and D are based on the 82 B16F10 prioritized mutations, of which 30 were immunogenic. Each data point in the graphs is based on ≥4 mutations.

Figure 8:
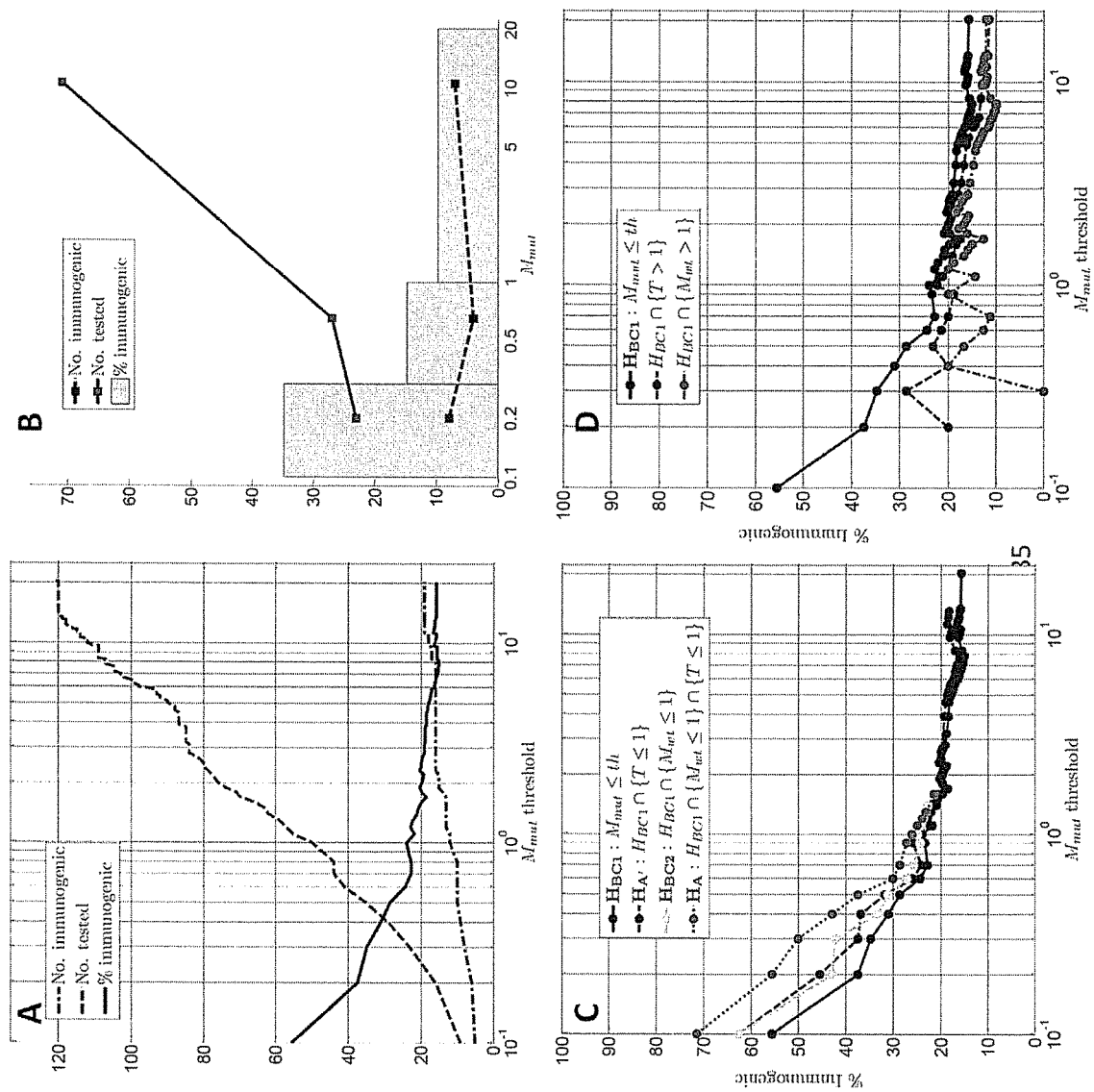

FIG. 8. Controlling for WT immunogenicity. To check whether omitting MUT+/WT+ solutions had an impact on these findings we excluded from the dataset 9 MUT+/WT+ mutations and 2 mutations for which the WT has not been measured, leaving in total 121 mutations (43 B16 and 78 CT26) of which 19 were MUT+/WT− (5 for B16 and 14 for CT26). We again found the same trends as in the complete dataset, namely, highly non-linear response as a function of the $M_{mut}$ score, superiority of the $H_A$ hypothesis over partial hypothesis, and inferiority of inverted hypotheses compared to the baseline control $H_{BC1}$. A Cumulative distribution of immunogenicity as a function of the $M_{mut}$ score. B Histogram of percent of immunogenic mutations per $M_{mut}$ bin. C Comparison of the percent of immunogenic mutations that satisfy the baseline control hypotheses $H_{BC1}$ with $H_A$, $H_{BC2}$ and $H_A$. D Comparison of the percent of immunogenic mutations that satisfy the baseline control hypotheses $H_{BC1}$ with the inverse hypotheses. See FIG. 5 legend for additional details.

Figure 9:
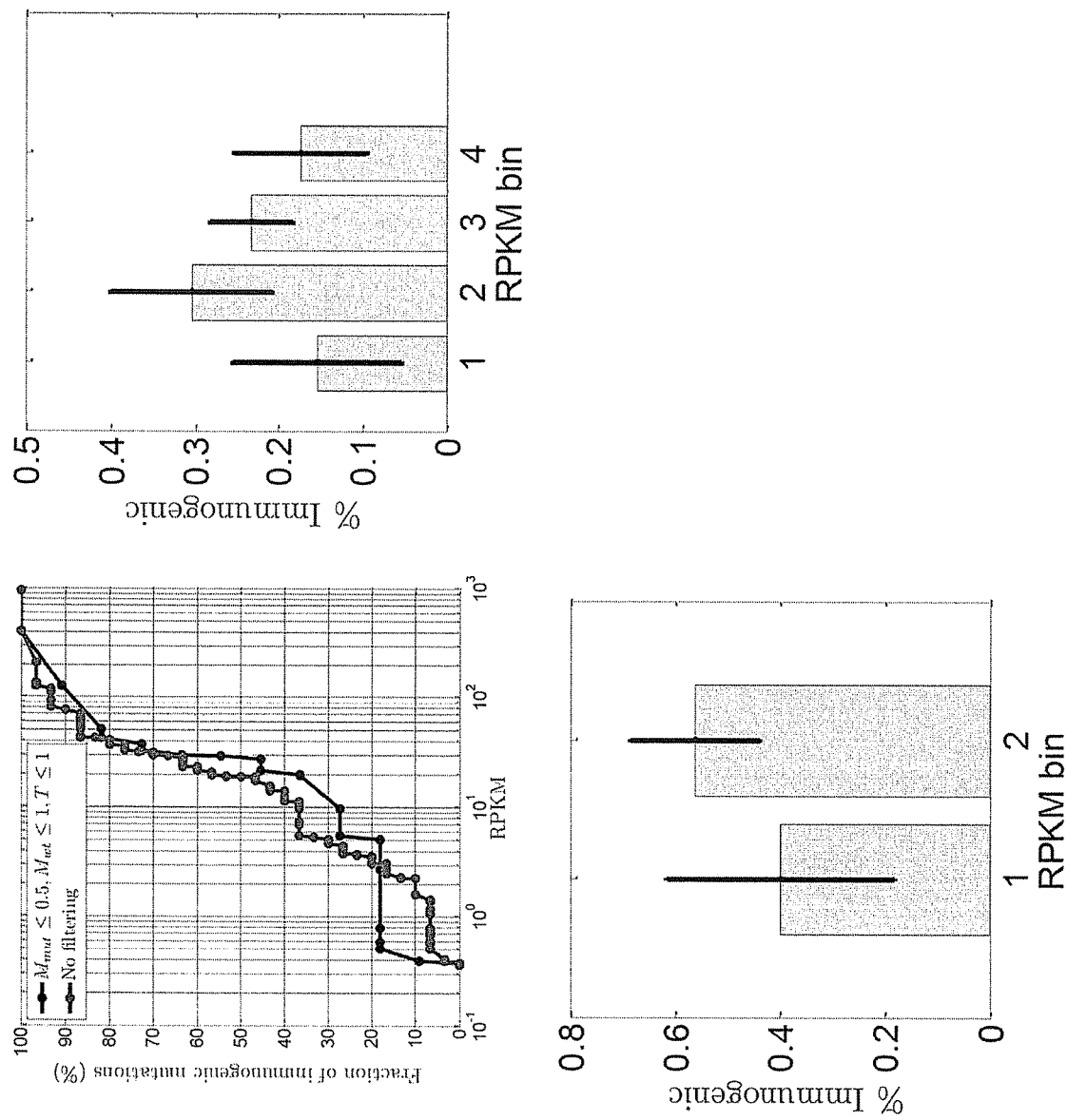

FIG. 9. Fraction of immunogenic mutations as a function of RPKM. Red: all 50 B16 mutations and 82 CT26 mutations with no filtering (132 mutations in total). Blue: mutations passing the $H_A$ hypothesis with $\alpha=1$, $\beta=0.5$, $\tau=1$. B. Percent of immunogenic mutations for different RPKM ranges with no filtering. RPKM bins are: 1=(0,1],2=(1,5], 3=(5,50],4=(50,∞). C Percent of immunogenic mutations for different RPKM ranges under the $H_A$ hypothesis with $\alpha=1$, $\beta=0.5$, $\tau=1$. RPKM bins are: 1=(0,1], 2=(1, ∞). Errors are S.E.

FIG. 10. Anchor and non-anchor position mutated class II immunogenic epitopes. Anchor position motifs were analyzed using SYFPEITHI.

FIG. 11. Proposed models for immunogenic tumor-associated epitopes.

Figure 12:
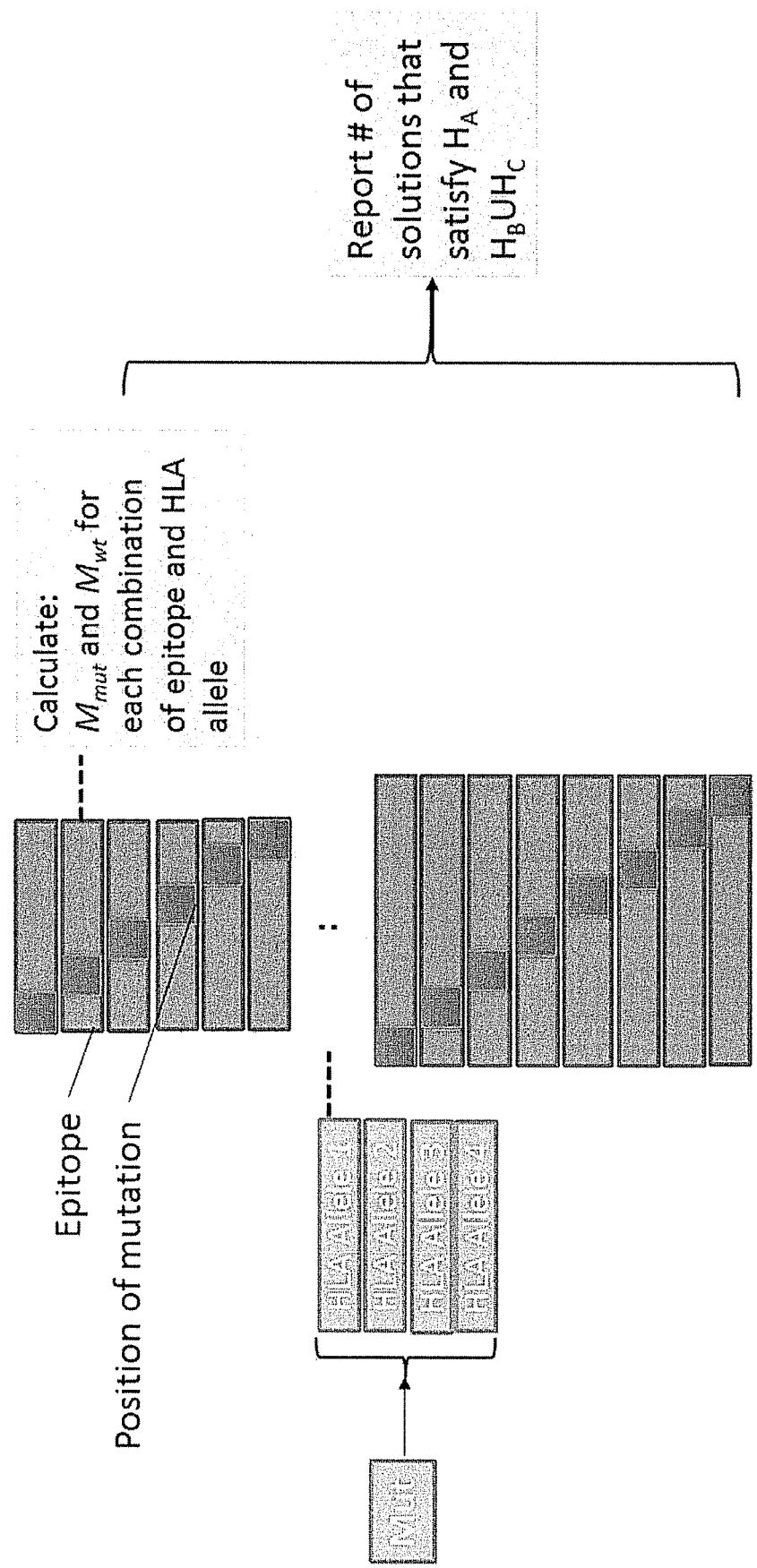

FIG. 12. Example of a method for weighing rank position of mutations. For each mutation the rank position in the list of ranked mutations can be further weighed by the number of solutions for which the combination of HLA types for the patient, possible window lengths for the HLA type and mutation position within the epitope resulted in a solution with low $M_{mut}$ or resulted in a $H_A$ and/or $H_BUH_C$ classification. Since all solutions per mutation potentially can be presented in parallel, this weighing factor may be an important contributor to the rank position of the mutation.

Figure 13:
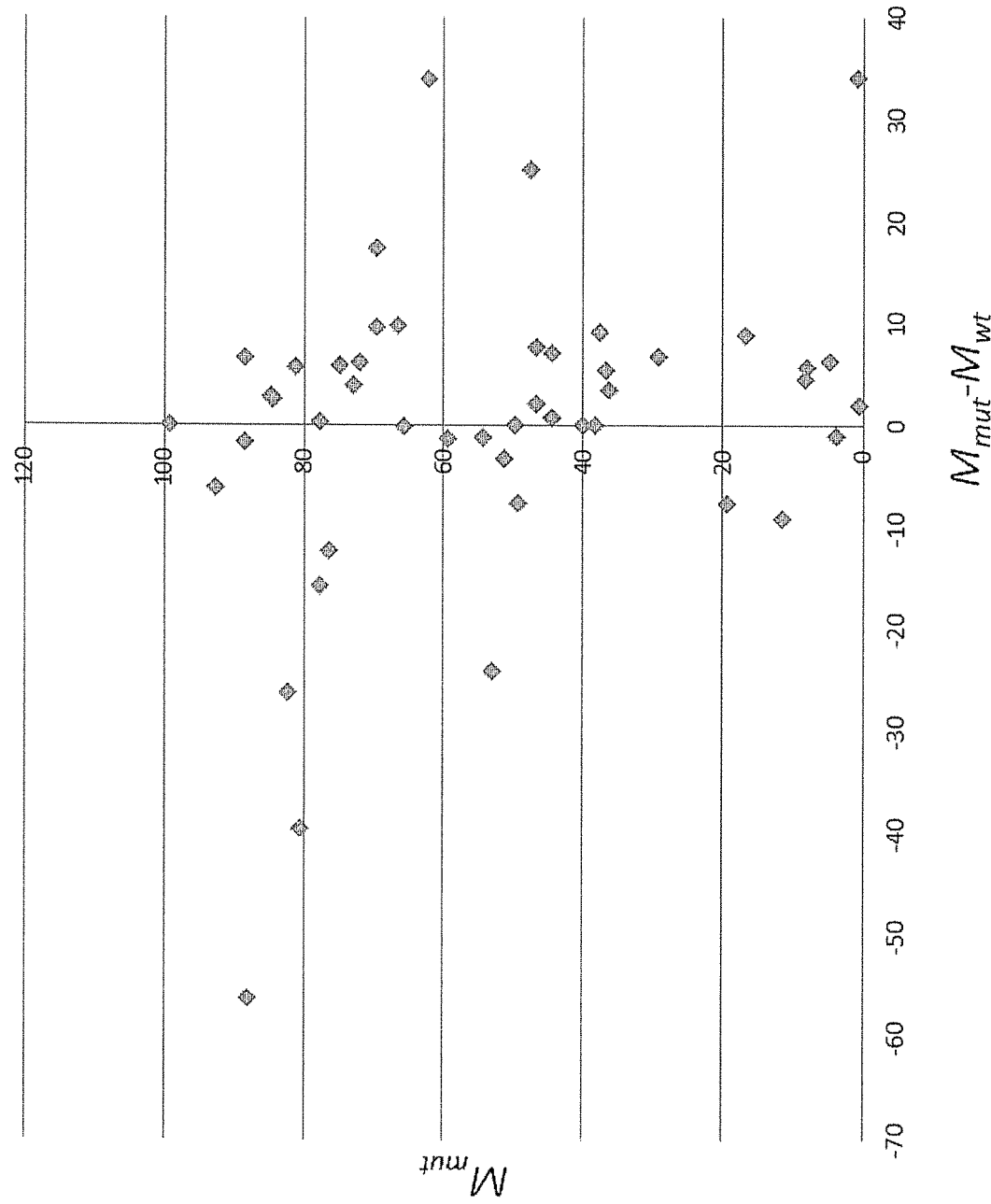

FIG. 13. Example of scatter plot of all epitope solutions for mutation chr14_52837882 from CT26 against $M_{mut}$ and $\Delta M=M_{mut}-M_{wt}$.

EXAMPLES

The techniques and methods used herein are described herein or carried out in a manner known per se and as described, for example, in Sambrook et al., Molecular Cloning: A Laboratory Manual, $2^{nd}$ Edition (1989) Cold Spring Harbor Laboratory Press, Cold Spring Harbor, N.Y. All methods including the use of kits and reagents are carried out according to the manufacturers' information unless specifically indicated.

Example 1

Establishing a Model for Predicting Immunogenicity of T Cell Epitopes

Previously we explored the immunogenicity of 50 somatic mutations identified in the B16F10 murine melanoma cell line (J. C. Castle et al., Exploiting the mutanome for tumor vaccination. Cancer Research 72, 1081 (2012)). These 50 mutations were selected from a pool of 563 expressed nonsynonymous somatic mutations primarily to maximize MHC class I expression (J. C. Castle et al., Exploiting the mutanome for tumor vaccination. Cancer Research 72, 1081 (2012)) (see also Example 2). For each mutation we predicted the minimal epitope, i.e., the epitope scoring the lowest MHC class I consensus score (Y. Kim et al., Nucleic Acids Research 40, W525 (2012)) (defined here as $M_{mut}$) when searching the space of all possible MHC class I alleles, potential epitope lengths and sequence windows (where to position the mutation) (J. C. Castle et al., Exploiting the mutanome for tumor vaccination. Cancer Research 72, 1081 (2012)). Measuring the immunogenicity of these mutations using RNA vaccination followed by peptide readout (see Example 2) confirmed earlier findings using peptide vaccination (J. C. Castle et al., Exploiting the mutanome for tumor vaccination. Cancer Research 72, 1081 (2012)), and showed that only 12 out of 50 mutations (24%) were immunogenic (Table 1), with MUT+/WT− sequences comprising only 10% for of all mutations tested.

TABLE 1

Number of immunogenic mutations after RNA vaccination of B16F10 and CT26.WT murine strains.

|  | MUT/WT immunogenicity | | | | | % immunogenic |
|---|---|---|---|---|---|---|
|  | +/+ | +/− | −/+ | −/− | Total | MUT+/total |
| B16F10 | 7 | 5 | 0 | 38 | 50 | 24% |
| CT26 | 2* | 14* | 1 | 63 | 80 | 20% |
| Total | 9 | 19 | 1 | 101 | 130 | 21.50% |

*Two CT26 MUT+ mutations were excluded from this table because their WT reactivity has not been measured yet. In total there were 18 MUT+ mutations out of 82 CT26 mutations measured thus far, resulting in 22% success rate.

The results of the B16F10 murine test case demonstrate that naively selecting expressed nonsynonymous mutations with low $M_{mut}$ scores (≤3.9) yields rather low success rates for predicting immunogenicity. Hence a better understanding of the mechanisms driving immunogenicity is required if personalized vaccines targeting tumor-specific neoantigens are to become effective therapies. In an effort to uncover additional variables that contribute to immunogenicity we explored the immunogenicity of expressed non-synonymous somatic mutations identified in a colorectal murine cell line CT26.WT. In total, 96 mutations were selected based on their $M_{mut}$ scores (low vs. high), mean RPKM (low vs. high), and cellular localization (intra- vs. extra-cellular), and tested for immunogenicity using RNA vaccination with both peptide and RNA readout (see Example 2 for further details). Together with the B16F10 cell line, our dataset comprised of 132 epitopes, whose immunogenicity was measured ex vivo on murine splenocytes.

The MHC consensus score. To investigate the dependence of immunogenicity on $M_{mut}$, we plotted the cumulative percent of immunogenic mutations as a function of $M_{mut}$, that is, the percent of mutations with an $M_{mut}$ score smaller than a given threshold (denoted by β) that were immunogenic. An analysis of the combined B16 and CT26 datasets spanning a total of 132 mutations reveals a highly nonlinear dependence of the immunogenicity success rate on $M_{mut}$ (FIG. 2A). FIG. 2A shows that immunogenic mutations are enriched for extremely low $M_{mut}$ scores (≤~0.2). For $M_{mut}$≤0.1 the percent of immunogenic mutations peaks at ~60%, and quickly decays as $M_{mut}$ increases, dropping below ~25% for $M_{mut}$≥2. The percent of immunogenic mutations with $M_{mut}$≤0.3 versus >0.3 was 44.4% compared with 17.1%, a statistically significant difference (P value=0.004, Fisher's exact test, one tailed). A histogram of the percent of immunogenic mutations for three $M_{mut}$ bins: ≤0.3, (0.3, 1] and >1 shows that the percent of immunogenic mutations drops as $M_{mut}$ increases (FIG. 2B). The differences between the success rate of the lowest bin ($M_{mut}$≤50.3), 44.4%, and both the central bin, 20.7%, and the highest bin ($M_{mut}$>1), 15.8%, in FIG. 2B were statistically significant (P values=0.05 and 0.004, respectively, Fisher's exact test, one tailed), indicating that for $M_{mut}$>~0.3 the success rate drops in a statistically significant manner. A similar trend in the success rate is also observed when analyzing B16 and CT26 mutanomes separately (FIG. 3).

Thus far our criteria for selecting mutations focused on presentation, and we have seen that restricting the MHC binding score of the mutated epitope allows prediction of immunogenic epitopes with up to 60% precision. Presentation, however, is a necessary but not sufficient condition to induce immunogenicity. By identifying additional criteria for TCR recognition we may be able to further improve the precision of our prediction. We hypothesized two mutually exclusive mechanisms for driving immunogenicity, which we refer to as the class I and class II immunogenicity models.

Class I immunogenicity. In order for the TCR repertoire to recognize a mutated epitope and generate an immune response we hypothesized that three conditions must be satisfied ($H_A$ FIG. 4): (i) the wild type epitope, at some point during the development of the organism, was presented to the immune system leading to deletion of matching TCRs via strong TCR/pMHC binding, (ii) the mutated epitope is presented, and (iii) the physico-chemical properties of the mutated amino acid are sufficiently "different" from the wild type amino acid (by some metric that we shall define below) so that the TCR repertoire is able to "detect" or "register" this substitution. Conditions (i) and (ii) ensure that the immune system is actually exposed to the change, i.e., the mutation. Condition (iii) requires that the mutation significantly change the physico-chemical character of the wild type amino acid so that the binding affinity of the mutated epitope to extant (undeleted) TCR potentially increases, thereby turning on the signaling cascade that leads to an immune response (FIG. 5).

The TCR recognition score. Class I immunogenicity models requires a metric to estimate the physico-chemical difference between two amino acids. It is well known in molecular evolution that amino acids that interchange frequently are likely to have chemical and physical similarities whereas amino acids that interchange rarely are likely to have different physico-chemical properties. The likelihood for a given substitution to occur in nature compared with the likelihood for this substitution to occur by chance is measured by log-odds matrices. The patterns observed in log-odd matrices imposed by natural selection "reflect the similarity of the functions of the amino acid residues in their weak interactions with one another in the three dimensional conformation of proteins" (M. O. Dayhoff, R. M. Schwartz, B. C. Orcutt, A model for evolutionary change. M O Dayhoff, ed. Atlas of protein sequence and structure Vol. 5, 345 (1978)). We therefore used evolutionary based log-odds matrices, which we refer to here as "T scores" to reflect TCR recognition, as effective scoring matrices for cancer associated amino acid substitutions. Substitutions with positive T scores (i.e., log-odds) are likely to occur in nature, and hence correspond to two amino acids that have similar physicochemical properties. The class I model predicts that substitutions with positive T scores would have a lower likelihood of being immunogenic. Conversely, substitutions with negative T scores reflect substitutions that are unlikely to occur in nature and hence correspond to two amino acids that have significantly different physico-chemical properties. According to our model, such substitutions would have a greater chance of being immunogenic. We compared different methods of estimating log-odds matrices and found results to be largely robust to the exact method chosen. The maximum likelihood (ML) based estimation approach known as WAG (S. Whelan, N. Goldman, Molecular biology and evolution 18, 691 (2001)), using a PAM (point accepted mutation) distance of 250 appeared to separate predicted immunogenic from non-immunogenic mutations best, and therefore we present results with this matrix (see Example 2 for further details).

Class II immunogenicity. In the class II model for immunogenicity we hypothesize that a mutation is likely to be immunogenic if the immune system has never before seen the wild type epitope, and is therefore challenged by the mutated epitope. Therefore in order for a mutation to be immunogenic in this model we hypothesized that two conditions must be satisfied: (i) the wild-type epitope was never presented to the immune system, (ii) the mutated peptide is presented. These conditions can be co-satisfied if, for example, the mutation hits an anchor position thereby changing a "nonbinder" epitope into a "binder". Formally, class II immunogenicity can be separated into two sub-hypotheses: high T scores ($H_B$ in FIG. 4) and low T scores ($H_C$ in FIG. 4). However, since the assumption is that the wild type epitope is not presented, the nature of the amino acid substitution is not expected to have an impact on TCR recognition and we shall therefore equate class II immunogenicity with the united hypothesis: $H_B \cup H_C$.

Testing class I immunogenicity. The assumptions of class I immunogenicity ($H_A$ in FIG. 4) can be restated mathematically as follows: we require that the wild type epitope is presented ($M_{wt}$≤α), the mutated epitope is presented ($M_{mut}$≤β), and the amino acid substitution is non-trivial (T≤τ), where $M_{wt}$ is defined as the MHC consensus score of the mutated epitope (same HLA allele and window length) replacing the mutated amino acid with the wild type amino acid, and T denotes the T score. Since all three conditions are necessary, we expect that the precision of the $H_A$ classifier will be higher compared to a classifier based on $M_{mut}$ alone ($H_{BC1}$ in FIG. 4) or compared to the partial hypotheses: $H_{BC1} \cap \{M_{wt} \le \alpha\}$ and $H_{BC1} \cap \{T \le \tau\}$. We therefore calculated the percent of immunogenic mutations (number of true positives divided by the sum of true positives and false positives) as a function of β for $H_{BC1}$ for the partial hypothesis $H_A$: $H_{BC1} \cap \{T \le \tau\}$ and for the partial hypothesis $H_{BC2}$: $H_{BC1} \cap \{M_{wt} \le \alpha\}$. We found that a conservative threshold for τ in the range of ≈0.5 to 1 performed best (the range of the WAG250 matrix is from −5.1 (F⇔G substitution) to +5.4 (F⇔Y substitution). We also found that a can be restricted conservatively compared to β, setting α√1. FIG. 6A indeed shows that, when considering the pooled mutanome of B16 and CT26, classifiers based on $H_{BC2}$, and $H_A$ attained greater precision than the baseline control hypothesis $H_{BC1}$. Moreover, a classifier based on the complete hypothesis $H_A$ attained greater precision than the partial hypotheses $H_{BC1}$, and $H_{BC2}$, thereby demonstrating an additive effect. The same conclusions hold when analyzing the B 16 and CT26 datasets separately (FIG. 7).

Since the conditions $M_{wt} \leq \alpha$ and $T \leq \tau$ are postulated to be necessary conditions for immunogenicity, one would except that a classifier based on either the condition $H_{BC1} \cap \{T > \tau\}$ or the condition $H_{BC1} \cap \{M_{wt} > \alpha\}$ (i.e., negating the secondary condition) would perform worse than $H_{BC1}$. Indeed we found that this is the case for B 16 and CT26 when analyzed together (FIG. 6B) or separately (FIG. 7). Therefore we conclude that the B16 and CT26 datasets support both together and separately the $H_A$ hypothesis. Omitting mutations where the WT RNA also showed reactivity did not affect these conclusions (FIG. 8).

Controlling for the $H_A$ hypothesis. Although mutations with high T scores may still be immunogenic, a hypothesis that enriches for such mutations should statistically enrich for non-immunogenic mutations. Therefore if we compare the $H_A$ hypothesis ($H_{BC2} \cap \{T \leq \tau\}$) with its inverse, $H_{BC2} \cap \{T > \tau\}$ ($H_n$ in FIG. 4), we should observe a statistically significant depletion of immunogenic mutations. Table 2 indeed shows that for $M_{mut} \leq \beta = 0.5$, $M_{wt} \leq \alpha = 1$, and $T \leq \tau = 1$, $H_A$ outperforms $H_n$, with a success rate of 52.5% (n=21) compared to 21.4% (n=14; P=0.068, one tailed Fisher's exact test).

$H_A$ also performs better than the baseline control $H_{BC2}$, which achieves 41.2% (n=35). As we decrease β the difference between the success rates of $H_A$ and $H_n$ become larger since the more stringent the condition on β, the more false positives are removed from the $H_A$ group. For example, for β=0.25 the success rate of the $H_A$ group was 67% (n=14) compared to a success rate of 17% (n=6) for group $H_n$ (P=0.066, one tailed Fisher's exact test)—see Table 3.

TABLE 2

Percent of immunogenic mutations under various hypotheses based on the B16 and CT26 pooled datasets comprising 133 mutations.

| | | Hypothesis parameters | | | |
|---|---|---|---|---|---|
| | | $M_{mut}$ threshold (β) | $M_{wt}$ threshold (α) | T score threshold (τ) | % of immunogenic mutations |
| Hypothesis | $H_{BC1}$ | ≤2 | | | 22/83 (26.5%) |
| | | ≤1 | | | 18/56 (32.1%) |
| | | ≤0.1 | | | 6/10 (60%) |
| | $H_{A'}$ | ≤0.1 | | ≤1 | 6/9 (66.7%) |
| | $H_{BC2}$ | | ≤1 | | 6/9 (66.7%) |
| | $H_A$ | | | ≤1 | 6/8 (75%) |
| | $H_{A'}$ | ≤0.2 | | ≤1 | 8/14 (57.1%) |
| | $H_{BC2}$ | | ≤1 | | 9/17 (52.9%) |
| | $H_n$ | | | >1 | 1/6 (16.7%) |
| | $H_A$ | | | ≤1 | 8/12 (66.7%) |
| | $H_{BC2}$ | ≤0.5 | ≤1 | | 14/34 (41.2%) |
| | $H_n$ | | | >1 | 3/14 (21.4%) |
| | $H_A$ | | | ≤1 | 11/21 (52.4%) |
| | $H_B UH_C$ | ≤0.5 | >1 | | 1/6 (16.7%) |

TABLE 3

Ranked list of 133 measured B16F10/CT26.WT mutations that satisfy the basic control hypothesis $H_{BC1}$ ($M_{mut} \leq 0.25$) broken down into the three disjoint hypothesis classes: $H_A$ hypothesis for immunogenic mutations ($M_{wt} \leq 0.8$, T ≤ 0.5), $H_n$/inverse $H_A$ hypothesis enriching for non-immunogenic mutations ($M_{wt} \leq 0.8$, T > 0.5), and $H_B UH_C$ hypothesis for immunogenic mutations ($M_{wt} > 0.8$). $H_A$ and $H_B UH_C$ candidates are proposed to be ranked based on the relative importance of distinguishing variables. For $H_A$ the proposed order is: $M_{mut}$ (descending) → T score (descending) → $M_{WT}$ descending. For $H_B UH_C$ the proposed order is: $M_{mut}$ (descending) → $M_{WT}$ (ascending). Errors are standard errors.

| Sample | Mut | Response | RNA response (MUT) | RNA response (WT) | Symbol (Ingenuity) | MHC I allele | epitope (MUT) | epitope (WT) | Mean Expression | $M_{mut}$ | $M_{wt}$ | T score (WAG250) |
|---|---|---|---|---|---|---|---|---|---|---|---|---|
| Class I immunogenicity ($H_A$): 67 ± 14% success rate ||||||||||||
| B16 | 33 | CD8 | yes | no | PBK | H-2-Db | AAVILRDALHM | AAVILRVALHM | 19.6 | 0.1 | 0.1 | -2.7 |
| CT26 | 14 | | no | no | Nphp3 | H-2-Dd | GGPGSEKSL | GGPGSGKSL | 0.6 | 0.1 | 0.1 | -0.5 |
| B16 | 37 | | no | no | DPF2 | H-2-Db | LALPNNYCDV | LALPNNYCDF | 20.0 | 0.1 | 0.1 | -0.1 |
| B16 | 25 | CD4 | yes | yes | PLOD2 | H-2-Db | SHLNNDVWQI | SHLNNDFWQI | 21.7 | 0.1 | 0.1 | -0.1 |
| CT26 | 37 | CD4 | yes | no | Dhx35 | H-2-Kd | YYMRDVIAI | YYMRDVTAI | 5.5 | 0.1 | 0.1 | -0.1 |
| CT26 | 26 | CD8 | yes | no | E2f8 | H-2-Kd | TYLQPAQAQM | IYLQPAQAQM | 29.5 | 0.1 | 0.1 | -0.1 |
| B16 | 21 | CD4 | yes | no | ATP11A | H-2-Db | QSLGFTYL | QRLGFTYL | 42.7 | 0.1 | 0.8 | -0.1 |
| CT26 | 13 | | yes | no | Nphp3 | H-2-Kd | EYWASRALDS | EYWASRALGS | 0.5 | 0.1 | 0.1 | 0.1 |
| CT26 | 16 | | no | no | H2-Q8 | H-2-Kd | GYLQFAYEGC | GYLQFAYEGR | 5.1 | 0.2 | 0.2 | -1.7 |
| B16 | 46 | CD4 | yes | yes | ACTN4 | H-2-Kb | VTFQAFIDVMS | VTFQAFIDFMS | 125.6 | 0.2 | 0.1 | -0.1 |
| CT26 | 15 | | no | no | Slc41a2 | H-2-Kd | PYLTALDDLL | PYLTALGDLL | 2.8 | 0.2 | 0.2 | 0.1 |
| CT26 | 27 | | yes | | Agxt2l2 | H-2-Dd | AGGLFVADAI | AGGLFVADEI | 29.7 | 0.2 | 0.3 | 0.1 |
| Class II immunogencity ($H_B UH_C$): 0% success rate ||||||||||||
| CT26 | 25 | | no | no | Pcdhga8 | H-2-Dd | VGINFLQSYQ | VGINSLQSYQ | 26.2 | 0.1 | 2.7 | -2.1 |
| CT26 | 1 | | no | no | Gm8909 | H-2-Dd | TRPARDGTF | TRPAGDGTF | 11.0 | 0.2 | 1.6 | -1.0 |
| CT26 | 40 | | no | no | Zfp449 | H-2-Ld | EPQIAMDDM | EPQIDMDDM | 0.7 | 0.25 | 1.25 | -0.2 |
| $H_n$: 17 ± 15% success rate ||||||||||||
| B16 | 49 | | no | no | FAT1 | H-2-Db | IAMQNTTQL | IAIQNTTQL | 18.8 | 0.1 | 0.1 | 2.6 |
| B16 | 36 | | no | no | TM9SF3 | H-2-Kb | AIYHHASRAI | AIYYHASRAI | 51.1 | 0.2 | 0.3 | 2.7 |
| CT26 | 39 | CD8 | yes | no | Als2 | H-2-Kd | SYIALVDKNI | SYLALVDKNI | 4.7 | 0.2 | 0.1 | 2.7 |
| CT26 | 2 | | no | no | Snap47 | H-2-Dd | VIPILEMQF | VIPILEVQF | 15.5 | 0.2 | 0.2 | 1.8 |
| CT26 | 17 | | no | no | H2-Q8 | H-2-Kd | GYLQFAYDGR | GYLQFAYEGR | 5.1 | 0.2 | 0.2 | 2.9 |
| CT26 | 38 | | no | | Cspp1 | H-2-Kd | VYLNLLLKFT | VYLNLFLKFT | 0.7 | 0.2 | 0.1 | 2.0 |

An Example of additional weighing factors that may further improve immunogenicity ranking is given in Example 3.

More generally the list of mutations that satisfy $H_{BC1}$ ($M_{mut} \leq \beta$) can be classified into the three categories: $H_A$, $H_n$, and $H_B UH_C$ (Table 3), where $H_A$ enriches for immunogenic mutations, $H_n$ enriches for non-immunogenic mutations. In the case of B16 and CT26, all three candidates in the $H_B UH_C$ group were non-immunogenic, contrary to our expectation. However, if a more realistic threshold $\alpha^*$ for $M_{wt}$ is chosen such that $\alpha^* >> \alpha$, then there would be no predictions that could be tested for $H_B UH_C$.

the $H_A$ filtering hypothesis), although suggestive, it should be noted that these results are within the range of error.

Survey of published CD8+ epitopes. We were next interested to see if published T cell-defined tumor antigens with single amino acid substitutions eliciting CD8+ restricted response fulfilled our models for immunogenicity. Of the 17 epitopes that were published (P. Van der Bruggen, V. Stroobant, N. Vigneron, B. Van den Eynde. (Cancer Immun, http://www.cancerimmunity.org/peptide/, 2013)) (Table 4), five satisfied the criteria for $H_A$ ($\alpha=0.7$, $\beta=0.2$, $\tau=0.5$), four satisfied the criteria for $H_C UH_B$ ($\alpha=2.2$, $\beta=0.4$), and two satisfied the $H_n$ criterion ($\alpha=0.6$, $\beta=0.3$, $\tau=1.7$).

TABLE 4

Published epitopes with single amino acid substitution generating CD8+ responses. See Example 2 for list of references. Anchor position mutations in the $H_B UH_C$ group are highlighted in red.

| Hypothesis | $M_{mut}$ threshold | $M_{wt}$ threshold | T score threshold | $M_{mut}$ | $M_{wt}$ | T score* | Gene | MUT epitope | WT epitope | Source | |
|---|---|---|---|---|---|---|---|---|---|---|---|
| $H_A$ | ≤0.2 | ≤0.7 | ≤0.5 | 0.10 | 0.10 | −2.1 | SIRT2 | KIFSEVTLK | KIFSEVTPK | 1 | ←MZ7-MEL |
| | | | | 0.10 | 0.10 | −0.1 | SNRPD | SHETVIIEL | SHETVTIEL | 1 | ←MZ7-MEL |
| | | | | 0.14 | 0.22 | 0.5 | ME1 | FLDEFMEGV | FLDEFMEAV | 2 | |
| | | | | 0.20 | 0.70 | −1.0 | RBAF600 | RPHVPESAF | GPHVPESAF | 1 | ←MZ7-MEL |
| | | | | 0.15 | 0.20 | −2.1 | PRDX5 | LLLDDLLVSI | LLLDDSLVSI | 3 | |
| $H_n$ | ≤0.3 | ≤0.6 | ≥1.7 | 0.25 | 0.20 | 1.7 | N-ras | ILDTAGREEY | ILDTAGQEEY | 4 | |
| | | | | 0.30 | 0.60 | 1.9 | EEF2 | ETVSEQSNV | ETVSEESNV | 10 | |
| $H_B$ | ≤0.25 | ≥2.25 | >0.5 | 0.15 | 10.20 | 1.2 | EFTUD2 | KILDAVVAQK | KILDAVVAQE | 1 | ←MZ7-MEL |
| | | | | 0.25 | 2.25 | 1.2 | MYO1B | KINKNPKYK | EINKNPKYK | 5 | |
| $H_C$ | <0.4 | >10 | ≤0.5 | 0.20 | 10.95 | −2.3 | FLT3 | YVDFREYEYY | YVDFREYEYD | 6 | |
| | | | | 0.38 | 10.58 | −2.1 | CTNNB1 | SYLDSGIHF | SYLDSGIHS | 7 | |
| other | ≥0.65 | ≥1 | | 0.65 | 2.70 | −2.1 | OS-9 | KELEGILLL | KELEGILLP | 8 | |
| | | | | 1.20 | 1.00 | 0.1 | GPNMB | TLDWLLQTPK | TLGWLLQTPK | 1 | ←MZ7-MEL |
| | | | | 2.68 | 3.58 | 1.0 | ACTN4 | FIASNGVKLV | FIASKGVKLV | 9 | |
| | | | | 4.20 | 4.60 | −1.2 | P53 | VVPCEPPEV | VVPYEPPEV | 11 | |
| | | | | 26.40 | 29.75 | −1.7 | CDK4 | ACDPHSGHFV | ARDPHSGHFV | 12 | |
| | | | | 33.30 | 29.80 | −2.9 | K-ras | VVVGAVGVG | VVVGAGGVG | 13 | |

*Based on WAG250 log-odds matrix, color legend: T ≤ 0.5, 0.5 < T ≤ 1, T > 1

Maximal precision of immunogenicity classifiers. According to Table 1 the average success rate for prediction immunogenicity in the combined B16 and CT26 datasets was 22.7% (=30/132). By applying the most stringent threshold on the $M_{mut}$ score ($\beta=0.1$), the precision of an immunogenicity classifier increases to 60% (=6/10; $H_{BC1}$ in Table 2). By combining $H_{BC1}$ with either the $M_{wt} \leq \alpha$ condition or the T≤τ condition ($\alpha=1$, $\tau=1$) precision is increased to 66.7% (=6/9). The $H_A$ based classifier, which combines both criteria, results in an additive response, which increases the precision to 75% (=6/8) (Table 2).

B16 epitope MUT33. The $H_A$-class epitope that was ranked the highest by all evolutionary models (except the PAM matrix) in the pooled B16/CT26 dataset was B16's MUT33 (see Table 3). Further analysis revealed that MUT33 indeed invoked an MHC class I restricted CD8+ response and exhibited ex vivo immunogenicity against the minimal predicted epitope (data not shown).

Role of gene expression. Plotting the fraction of immunogenic mutations (no. of immunogenic mutations with RPKM values below a given threshold over the total no. of immunogenic mutations) as a function of RPKM values for B16 and CT26 indicates that this ratio somewhat stagnates at very low RPKM values (FIG. 9A). This effect is observed whether the $H_A$ criterion is applied or not. Plotting the percent immunogenic mutations for different RPKM bins (FIG. 9B and C) suggests that RPKM values≤~1 have a somewhat lower success rate (both with or without applying Thus, the $H_A$ and $H_C UH_B$ hypotheses together accounted for roughly 50% of the published epitopes. Interestingly, 3 out of the 4 published epitopes that satisfied the $H_C UH_B$ condition (red boxes in Table 4) had an $M_{wt}$ score that was larger than 10 due to anchor position mutations (FIG. 10). Since the requirement for the $H_C UH_B$ hypothesis is that the probability that any cell present the wild type epitope during the development of the organism is kept negligibly small it is expected that the threshold for $M_{wt}$ should be kept high, i.e., $\alpha^* >> \alpha$. Indeed when increasing $\alpha$ from 0.8 to >3 the false positives for B16/CT26 in Table 3 disappear. Therefore a more realistic threshold for $M_{wt}$ under the $H_C UH_B$ hypothesis may be somewhere between 3 and 10.

The MZ7-MEL cell line. To test the ability of our immunogenicity models to predict immunogenic epitopes in a human tumor model setting, we explored the MZ7-MEL cell line, established in 1988 from a splenic metastasis of a patient with malignant melanoma (V. Lennerz et al., Proceedings of the National Academy of Sciences of the United States of America 102, 16013 (2005)). Screening of a cDNA library from MZ7-MEL cells with autologous tumor-reactive T cells revealed at least five neoantigens capable of generating CD8+ responses (V. Lennerz et al., Proceedings of the National Academy of Sciences of the United States of America 102, 16013 (2005)). This constitutes the largest set of CD8+ neoantigens derived from a patient to date. Applying our immunogenicity models to these epitopes we found that three neoantigens were classified as $H_A$ epitopes, and one neoantigen, an anchor position mutation, was classified as an $H_BUH_C$ epitope (arrows in Table 4, and FIG. 10). Thus, four of the five epitopes could be explained by our immunogenicity models.

To test our ability to predict these epitopes de novo in the MZ7-MEL cell line we sequenced the exome of the MZ7-MEL cell line (see Methods). In total 743 expressed nonsynonymous mutations were identified. All five mutations previously identified by Lennerz et al. (V. Lennerz et al., Proceedings of the National Academy of Sciences of the United States of America 102, 16013 (2005)) were found. We then calculated for each mutation the T score, $M_{mut}$ and $M_{wt}$, reporting also the HLA allele and epitope that resulted in the minimal MHC consensus score for the given mutation. Mutations were classified into one of three groups: $H_A$, $H_BUH_C$, and $H_n$ using the thresholds $\alpha=0.8$, $\beta=0.2$, $\tau=0.5$ (plus the condition RPKM>0.2), and then ranked based on their potential to be immunogenic, as explained in Table 3. We found that out of 743 mutations, 32 mutations satisfied the $H_A$ criteria (Table 5), 12 satisfied the $H_BUH_C$ criterion (Table 6) and 15 satisfied the $H_n$ criterion.

TABLE 5

$H_A$-classified MZ7-MEL cell mutations. 32 of the 743 expressed nonsynonymous mutations in MZ7-MEL were classified as $H_A$-immunogenic using the thresholds: $\alpha = 0.8$, $\beta = 0.2$ and $\tau = 0.5$. Rank is based on an $M_{mut}$ (descending) → T score (descending) sorting scheme. Immunogenic neoantigens identified by Lennerz et al. are highlighted in yellow. In addition RPKM was required to exceed 0.2.

| Rank* | Gene | $M_{mut}$ | T score** | $M_{wt}$ | Mean exp | |
|---|---|---|---|---|---|---|
| 1 | DPH2 | 0.1 | −2.9 | 0.1 | 10.7 | |
|  | ADHFE1 | 0.1 | −2.9 | 0.1 | 2.7 | |
| 2 | DDX41 | 0.1 | −2.1 | 0.1 | 24.8 | |
|  | SIRT2 | 0.1 | −2.1 | 0.1 | 15.7 | ←MZ7-MEL |
| 3 | PRIC285 | 0.1 | −1.0 | 0.4 | 5.4 | |
| 4 | CSTF3 | 0.1 | −0.5 | 0.1 | 11.2 | |
|  | ETFDH | 0.1 | −0.5 | 0.1 | 10.8 | |
| 5 | MED12 | 0.1 | −0.1 | 0.1 | 21.9 | |
|  | SNRPD1 | 0.1 | −0.1 | 0.1 | 18.0 | ←MZ7-MEL |
|  | MLLT6 | 0.1 | −0.1 | 0.2 | 14.7 | |
|  | AFAP1 | 0.1 | −0.1 | 0.2 | 5.1 | |
| 6 | MAP3K11 | 0.1 | 0.1 | 0.1 | 41.9 | |
| 7 | DHX30 | 0.1 | 0.3 | 0.1 | 34.4 | |
|  | ALK | 0.1 | 0.3 | 0.1 | 0.4 | |
|  | CHMP4B | 0.1 | 0.3 | 0.7 | 52.8 | |
| 8 | HADHB | 0.1 | 0.5 | 0.1 | 60.6 | |
|  | SUPT6H | 0.1 | 0.5 | 0.1 | 25.4 | |
|  | C12orf35 | 0.1 | 0.5 | 0.1 | 3.1 | |
|  | ZDHHC5 | 0.1 | 0.5 | 0.4 | 27.6 | |
| 9 | WIPF1 | 0.15 | −2.1 | 0.15 | 37.2 | |
|  | ZNF740 | 0.15 | −2.1 | 0.5 | 9.7 | |
| 10 | MLL | 0.15 | 0.5 | 0.3 | 3.7 | |
| 11 | KIAA1715 | 0.2 | −2.1 | 0.1 | 6.3 | |
|  | CHD8 | 0.2 | −2.1 | 0.2 | 10.3 | |
| 12 | DDX28 | 0.2 | −1.7 | 0.2 | 7.2 | |
| 13 | MAPK1IP1L | 0.2 | −1.0 | 0.2 | 12.1 | |
|  | UBR4 (RBAF600) | 0.2 | −1.0 | 0.7 | 11.8 | ←MZ7-MEL |
| 14 | TRAK2 | 0.2 | −0.1 | 0.5 | 21.8 | |
| 15 | MAEA | 0.2 | 0.0 | 0.25 | 25.3 | |
| 16 | KLHL13 | 0.2 | 0.1 | 0.2 | 3.4 | |
| 17 | FOSL2 | 0.2 | 0.3 | 0.2 | 9.4 | |
| 18 | UTRN | 0.2 | 0.5 | 0.15 | 6.3 | |

*Rank is based on $M_{mut}$ and the T score
**T score is based on the WAG250 log-odds matrix

TABLE 6

$H_BUH_C$-classified MZ7-MEL cell mutations. 12 of the 743 expressed nonsynonymous mutations in MZ7-MEL were classified as $H_BUH_C$-immunogenic using the thresholds: $\alpha^* = 0.8$, $\beta = 0.2$ and RPKM >2. Rank is based on a $M_{mut}$ (descending) → $M_{wt}$ (ascending) sorting scheme. Immunogenic neoantigens identified by Lennerz et al. are highlighted in yellow.

| Rank* | Gene | $M_{mut}$ | $M_{wt}$ | Mean exp | |
|---|---|---|---|---|---|
| 1 | NF1 | 0.1 | 1.4 | 6.8 | |
| 2 | MESP2 | 0.1 | 1.3 | 0.3 | |
| 3 | EFTUD2 (SNRP116) | 0.15 | 10.2 | 22.0 | ←MZ7-MEL |
| 4 | SEC31A | 0.15 | 2.55 | 33.3 | |
| 5 | ZNF335 | 0.2 | 18.35 | 8.3 | |
| 6 | CPEB1 | 0.2 | 4.2 | 6.0 | |
| 7 | UBAC2 | 0.2 | 2.8 | 7.5 | |
| 8 | FANCF | 0.2 | 2.4 | 3.9 | |
|  | RAPH1 | 0.2 | 2.4 | 3.0 | |
| 9 | ZNF557 | 0.2 | 1.4 | 1.5 | |

TABLE 6-continued $H_BUH_C$-classified MZ7-MEL cell mutations. 12 of the 743 expressed nonsynonymous mutations in MZ7-MEL were classified as $H_BUH_C$-immunogenic using the thresholds: $\alpha^* = 0.8$, $\beta = 0.2$ and RPKM >2. Rank is based on a $M_{mut}$ (descending) → $M_{wt}$ (ascending) sorting scheme. Immunogenic neoantigens identified by Lennerz et al. are highlighted in yellow.

| Rank* | Gene | $M_{mut}$ | $M_{wt}$ | Mean exp |
|---|---|---|---|---|
| 10 | TLK2 | 0.2 | 1.35 | 2.9 |
| 11 | ST7 | 0.2 | 1.15 | 10.9 |

*Rank is based on $M_{mut}$ and $M_{wt}$

Of the 32 mutations classified as $H_A$, the three $H_A$-class mutations identified by Lennerz et al. (SIRT2, SNRPD1 and RBAF600) were ranked in $2^{nd}$, $4^{th}$ and $13^{th}$ positions out of 18 rank-classes, using a $M_{mut}$→T score ranking scheme (see Table 3). Of the 12 mutations classified as $H_BUH^C$, the forth Lennerz et al. mutation (SNRP116) ranked in the $3^{rd}$ position. Moreover, if a higher (more realistic) threshold for $M_{wt}$ was employed (e.g., $\alpha^*$~5) then the forth Lennerz et al. mutation is ranked in the $1^{st}$ position (together with just one additional anchor position mutation—Table 7). Finally, the four Lennerz et al. mutations were predicted to have the correct HLA allele, epitope length and mutation position as reported by the authors.

TABLE 7

$H_BUH_C$-classified MZ7-MEL cell mutations. 2 of the 743 expressed nonsynonymous mutations in MZ7-MEL were classified as $H_BUH_C$-immunogenic using the thresholds: $\alpha^* = 5$, $\beta = 0.2$ and RPKM >2. Rank is based on a $M_{mut}$ (descending) → $M_{wt}$ (ascending) sorting scheme. Immunogenic neoantigens identified by Lennerz et al. are highlighted in yellow.

| Rank* | Gene | $M_{mut}$ | $M_{wt}$ | Mean exp | |
|---|---|---|---|---|---|
| 1 | EFTUD2 (SNRP116) | 0.15 | 10.2 | 22.0 | ←MZ7-MEL |
| 2 | ZNF335 | 0.2 | 18.35 | 8.3 | |

*Rank is based on $M_{mut}$ and $M_{wt}$

Conclusions

The analysis of the B 16 and CT26 datasets support a model where immunogenicity is conferred if three conditions are satisfied: the wild type peptide is presented, the mutated peptide is presented, and the amino acid substitution has a sufficiently low log-odds score (FIG. 11A). This model for immunogenicity, which we refer to as class I immunogenicity, is further supported in the human melanoma cell line model, MZ7-MEL. The MZ7-MEL model and published CD8+ restricted neoantigens support a second model, which we refer to as class II immunogenicity, in which the wild type epitope is not presented, but a substitution (e.g., in an anchor position) leads to a significant increase in the MHC consensus score (>5 to 10), resulting in a novel, never-before-seen epitope (FIG. 11B). This framework for defining immunogenicity is captured with a three-variable classification scheme ($M_{mut}$, $M_{wt}$, T score). Using this classification scheme we were able to reduce the MZ7-MEL 743 mutations to a list of 34 mutations, with 3 of the 5 Lennerz et al. epitopes ranking in the top 5 classes.

Table 7 demonstrates that class II immunogenic mutations are rare. Out of 743 mutations only 2 were classified as class. II immunogenic (using a realistic threshold for $M_{wt}$) compared with roughly 30 class I immunogenic mutations. A paucity of $H_BUH_C$-class mutations was also observed in the mouse melanoma models (Table 8). This observation underscores the importance of class I immunogenic of mutations for personalize vaccines, which are expected to be the dominate type mutations found in patient samples that can be used for vaccination. At the same time, the fact that one of the five epitopes found by Lennerz et al. was class II immunogenic may indicate that class II immunogenic mutations are more potent or somehow selected by the immune system.

TABLE 8

Number of candidate $H_A$ and $H_BUH_C$ mutations in different tumor models. ($\alpha = 0.8$, $\alpha^* = 5$, $\beta = 0.2$, $\tau = 0.5$).

| | | Hypothesis | |
|---|---|---|---|
| | | $H_A$ | $H_BUH_C$ |
| Strain | B16 | 27 | 0 |
| | CT26 | 13 | 0 |
| | MZ7-MEL | 35 | 2 |

Example 2

Materials and Methods

The materials and methods used in Example 1 are described below:

Animals

C57BL/6J and Balb/cJ mice (CRL) were kept in accordance with federal and state policies on animal research at the University of Mainz.

Cells for Melanoma and Colorectal Murine Tumor Model

B16F10 melanoma cell line (Product: ATCC CRL-6475, Lot Number: 58078645) and CT26.WT colon carcinoma cell line (Product: ATCC CRL-2638, Lot Number: 58494154) were purchased in 2010 from the American Type Culture Collection. Early (3rd, 4th) passages of cells were used for sequencing experiments. Cells were routinely tested for Mycoplasma. Re-authentification of cells has not been performed since receipt. MZ7-MEL cell line (established January 1988) and an autologous Epstein-Barr virus-transformed B cell line were obtained from Dr. Thomas Wölfel (Department of Medicine, Hematology Oncology, Johannes Gutenberg University).

Synthetic Peptides

Peptides were purchased from Jerini Peptide Technologies (Berlin, Germany) or synthesized from the TRON peptide facility. Synthetic peptides were 27 amino acids long with the mutated (MUT) or wild-type (WT) amino acid on position 14.

Immunization of Mice

Age-matched female C57BL/6 or Balb/c mice were injected intravenously with 20 µg in vitro transcribed mRNA formulated with 20 µl Lipofectamine™ RNAiMAX (Invitrogen) in PBS in a total injection volume of 200 µl (3 mice per group). The mice were immunized on day 0, 3, 7, 14 and 18. Twenty-three days after the initial injection mice were sacrificed and splenocytes were isolated for immunological testing (see ELISPOT assay). DNA-sequences representing one (Monoepitope) or two mutations (Biepitope) were constructed using the sequence of 27 amino acids (aa) with the mutation on position 14 and cloned into the pST1-2BgUTR-A120 backbone (S. Holtkamp et al., Blood 108, 4009 (2006)). In vitro transcription from this template and purification were previously described (S. Kreiter et al., Cancer Immunology, Immunotherapy 56, 1577 (2007)).

Enzyme-Linked Immunospot Assay

Enzyme-linked immunospot (ELISPOT) assay (S. Kreiter et al., Cancer Research 70, 9031 (2010)) and generation of syngeneic bone marrow derived dendritic cells (BMDCs) as stimulators were previously described (L. MB et al., J. Immunol. Methods 223, 77 (1999)). For the B16F10 model BMDCs were peptide pulsed (6 µg/ml), with the indicated mutation, the corresponding wild-type or with control peptide (VSV-NP). For the CT26 model in addition to the restimulation with peptides BMDCs were transfected with the corresponding in vitro transcribed mRNA and used for restimulation, as well. For the assay, $5 \times 10^4$ BMDCs were coincubated with $5 \times 10^5$ freshly isolated splenocytes in a microtiter plate coated with anti-IFN-γ antibody (10 µg/mL, clone AN18; Mabtech). After 18 hours at 37° C., cytokine secretion was detected with an anti-IFN-γ antibody (clone R4-6A2; Mabtech). Spot numbers were counted and analyzed with the ImmunoSpot® S5 Versa ELISPOT Analyzer, the ImmunoCapture™ Image Acquisition software and the ImmunoSpot® Analysis software Version 5. Statistical analysis was done by student's t-test and Mann-Whitney test (non-parametric test). Responses were considered significant with a p-value <0.05.

Intracellular Cytokine Assay

Aliquots of the splenocytes prepared for the ELISPOT assay were subjected to analysis of cytokine production by intracellular flow cytometry. To this end $2 \times 10^6$ splenocytes per sample were plated in culture medium (RPMI+10% FCS) supplemented with the Golgi inhibitor Brefeldin A (10 µg/mL) in a 96-well plate. Cells from each animal were restimulated for 5 h at 37° C. with $2 \times 10^5$ peptide pulsed or RNA-transfected BMDCs. After incubation the cells were washed with PBS, resuspended in 50 µl PBS and extracellularly stained with the following anti-mouse antibodies for 20 min at 4° C.: anti-CD4 FITC, anti-CD8 APC-Cy7 (BD Pharmingen). After incubation the cells were washed with PBS and subsequently resuspended in 100 µl Cytofix/Cytoperm (BD Bioscience) solution for 20 min at 4° C. for permeabilization of the outer membrane. After permeabilization the cells were washed with Perm/Wash-Buffer (BD Bioscience), resuspended in 50 µL/sample in Perm/Wash-Buffer and intracellularly stained with the following anti-mouse antibodies for 30 min at 4° C.: anti-IFN-γ PE, anti-TNF-α PE-Cy7, anti-IL2 APC (BD Pharmingen). After washing with Perm/Wash-Buffer the cells were resuspended in PBS containing 1% paraformyldehyde for flow cytometry analysis. The samples were analyzed using a BD FACSCanto™ II cytometer and FlowJo (Version 7.6.3).

Next Generation Sequencing

Nucleic acid extraction: DNA and RNA from bulk cells and DNA from mouse tissues were extracted using Qiagen DNeasy Blood and Tissue kit (for DNA) and Qiagen RNeasy Micro kit (for RNA).

DNA exome sequencing: Exome capture for B16F10, C57BL/6J and CT26.WT and DNA re-sequencing for Balb/cJ were performed in triplicates as previously described (J. C. Castle et al., Exploiting the mutanome for tumor vaccination. Cancer Research 72, 1081 (2012)). Exome capture for MZ7-MEL/EBV-B DNA re-sequencing was performed in duplicates using Agilent XT Human all Exon 50 Mb solution-based capture assay, designed to capture all protein coding regions. 3 µg purified genomic DNA (gDNA) was fragmented to 150-200 bp using a Covaris S2 ultrasound device. Fragments were end repaired, 5' phosphorylated and 3' adenylated according to the maufacturer's instructions. Agilent indexing specific paired-end adapters were ligated to the gDNA fragments using a 10:1 molar ratio of adapter to gDNA. 4 cycle pre-capture amplification was done using Agilent's InPE 1.0 and SureSelect indexing pre-capture PCR primers and Herculasell polymerase. 500 ng of adapter ligated, PCR enriched gDNA fragments were hybridized to Agilent's exome capture baits for 24 hrs at 65° C. Hybridized gDNA/RNA bait complexes where removed using streptavidin coated magnetic beads, washed and the RNA baits cleaved off during elution in SureSelect elution buffer. The eluted gDNA fragments were PCR amplified post-capture for 10 cycles using SureSelect Indexing Post-Capture PCR and index PCR primers and HerculaseII polymerase. All cleanups were done with 1.8× volume of Agencourt AMPure XP magnetic beads. All quality controls were done using Invitrogen's Qubit HS assay and fragment size was determined using Agilent's 2100 Bioanalyzer HS DNA assay. Exome enriched gDNA libraries were clustered on the cBot using Truseq SR cluster kit v2.5 using 7 pM library and 1×100 bps were sequenced on the Illumina HiSeq2000 using Truseq SBS kits.

RNA gene expression profiling (RNA-Seq): Barcoded mRNA-seq cDNA libraries were prepared in duplicate, from 5 µg of total RNA (modified Illumina mRNA-seq protocol using NEB reagents) mRNA was isolated using Seramag Oligo(dT) magnetic beads (Thermo Scientific) and fragmented using divalent cations and heat. Resulting fragments (160-220 bp) were converted to cDNA using random primers and SuperScriptll (Invitrogen) followed by second strand synthesis using DNA polymerase I and RNaseH. cDNA was end repaired, 5' phosphorylated and 3' adenylated according to NEB RNA library kit instructions. 3' single T-overhang Illumina multiplex specific adapters were ligated with T4 DNA ligase using a 10:1 molar ratio of adapter to cDNA insert. cDNA libraries were purified and size selected at 300 bp (E-Gel 2% SizeSelect gel, Invitrogen). Enrichment, adding of Illumina six base index and flow cell specific sequences was done by PCR using Phusion DNA polymerase and Illumina specific PCR primers. All cleanups up to this step were done with 1.8× volume of Agencourt AMPure XP magnetic beads. All quality controls were done using Invitrogen's Qubit HS assay and fragment size was determined using Agilent's 2100 Bioanalyzer HS DNA assay. Barcoded RNA-Seq libraries were clustered and 50 bps were sequenced as described above.

NGS data analysis, gene expression: The output sequence reads from RNA samples were preprocessed according to the Illumina standard protocol, including filtering for low quality reads. Sequence reads were aligned to the mm9 (A. T. Chinwalla et al., Nature 420, 520 (2002)) or hg18 (F. Collins, E. Lander, J. Rogers, R. Waterston, I. Conso, Nature 431, 931 (2004)) reference genomic sequence with bowtie (version 0.12.5) (B. Langmead, C. Trapnell, M. Pop, S. L. Salzberg, Genome Biol 10, R25 (2009)). For genome alignments two mismatches were allowed and only the best alignment ("-v2-best") reported, for transcript alignments default parameters were used. Reads not alignable to the genomic sequence were aligned to a database of all possible exon-exon junction sequences of the UCSC known genes (F. Hsu et al., Bioinformatics 22, 1036 (2006)). Expression values were determined by intersecting read coordinates with those of RefSeq transcripts, counting overlapping exon and junction reads, and normalizing to RPKM expression units (Reads which map per Kilobase of exon model per million mapped reads) (A. Mortazavi, B. A. Williams, K. McCue, L. Schaeffer, B. Wold, Nature methods 5, 621 (2008)).

NGS data analysis, somatic mutation discovery: Somatic mutations were identified as previously described (J. C.

Castle et al., Exploiting the mutanome for tumor vaccination. Cancer Research 72, 1081 (2012)). Sequence reads aligned to the mm9 or hg18 reference genome using bwa (default options, version 0.5.8c) (H. Li, R. Durbin, Bioinformatics 25, 1754 (2009)). Ambiguous reads mapping to multiple locations of the genome were removed. Mutations were identified using a consensus of two software programs: samtools (version 0.1.8) (H. Li, Bioinformatics 27, 1157 (2011)) and SomaticSniper (A. McKenna et al., Genome Research 20, 1297 (2010)). For B16F10 and C57BL/6J, also GATK was included (A. McKenna et al., Genome Research 20, 1297 (2010)). Potential somatic variations identified in all respective replicates were assigned a "false discovery rate" (FDR) confidence value (M. Löwer et al., PLoS computational biology 8, e1002714 (2012)) (CT26 and MZ7-MEL only).

Mutation Selection and Validation

The criteria for selecting the 50 B16F10 mutations for immunogenicity testing were previously described (J. C. Castle et al., Exploiting the mutanome for tumor vaccination. Cancer Research 72, 1081 (2012)). These criteria for the mutations included: (i) presence in all three B16F10 replicates and absence from all C57BL/6 triplicates, (ii) occur in a RefSeq transcript, (iii) cause nonsynonymous change, (iv) occurrence in B16F10-expressed genes (median RPKM across replicates >10, exon expression >0) and (v) for each mutation the $M_{mut}$ score (see below) was required to be <5. Of the 59 remaining mutations, the product of the quantile ranks of MHC class I score, MHC class II score and transcript expression was formed, and the first 50 mutations ($0.1 \leq M_{mut} \leq 3.9$) were selected for confirmation by PCR (see (J. C. Castle et al., Exploiting the mutanome for tumor vaccination. Cancer Research 72, 1081 (2012)) for further details). The criteria for the 96 CT26.WT mutations selected for immunogenicity testing were further refined and included the following: (i) presence in all CT26.WT three replicates and absence from all Balb/cJ three replicates, (ii) FDR≤0.05, (iii) occur in a UCSC known gene transcript, (iv) cause nonsynonymous change, (v) not present in dbSNP database (vi) not in a genomic repeat region. From the remaining 493 mutations, eight 12-member groups were defined according to three features: $M_{mut}$ score (lowest—[0.1,1.9] versus highest—[3.9-20.3]), compartment of the protein (extra-cellular, intra-cellular), and gene expression (below versus above the median of 7.1 RPKM), selecting mutations according to a greedy algorithm, and adjusting thresholds accordingly. 94 of the resultant 96 mutations were confirmed by PCR followed by Sanger sequencing.

The criteria for selecting MZ7-ML mutations for analysis included: (i) presence in two MZ7-MEL replicates and absence from two autologous EBV-B replicates, followed by steps (ii) to (vi) describe above for CT26.WT. Applying steps (i)-(vi) reduced the initial list of ~8000 mutations to 743.

MHC Binding Prediction and Calculation of the $M_{mut}$ Score

MHC binding predictions are performed using the IEDB analysis resource Consensus tool (http://tools.immuneepitope.org/analyze/html/mhc_binding.html) (Y. Kim et al., Nucleic Acids Research 40, W525 (2012)), which combines the best performing prediction methods based on benchmarking studies (H. H. Lin, S. Ray, S. Tongchusak, E. L. Reinherz, V. Brusic, BMC immunology 9, 8 (2008); B. Peters et al., PLoS computational biology 2, e65 (2006)) from ANN (C. Lundegaard et al., Nucleic Acids Research 36, W509 (2008); M. Nielsen et al., Protein Science 12, 1007 (2009)), SMM (B. Peters, A. Sette, BMC bioinformatics 6, 132 (2005)) and for some allele models also comblib (J. Sidney et al., Immunome Research 4, 2 (2008)). The consensus approach combines the prediction scores of all tools by generating a percentile rank, which reflects the binding prediction scores of the given peptide against peptide scores of five million random peptides from SWISSPROT.

For each mutation we calculated the predicted MHC consensus scores for all possible (i) sequence windows (where to position the mutation), (ii) epitope lengths and (iii) possible murine MHC class I alleles. The minimum of all MHC consensus scores was defined to be the $M_{mut}$ score.

Calculation of Log-Odds Matrices and the T Score

Log-odds matrices can be estimated from sequence alignment comparisons of large protein databases. The early log-odds matrices were based on pairwise comparison of sequences (BLOSUM62 (S. Kreiter et al., Cancer Immunology, Immunotherapy 56, 1577 (2007))) and the maximum parsimony (MP) estimation method (e.g., PAM250 (M. O. Dayhoff, R. M. Schwartz, B. C. Orcutt, A model for evolutionary change. M O Dayhoff, ed. Atlas of protein sequence and structure Vol. 5, 345 (1978)), JTT250 (S. Q. Le, O. Gascuel, Molecular biology and evolution 25, 1307 (2008)), and the Gonnet matrix (C. C. Dang, V. Lefort, V. S. Le, Q. S. Le, O. Gascuel, Bioinformatics 27, 2758 (2011))). More recently, maximum likelihood (ML) based methods were developed (e.g., VT160 (P. G. Higgs, T. K. Attwood, Bioinformatics and molecular evolution. (Wiley-Blackwell, 2009)), WAG (S. Whelan, N. Goldman, Molecular biology and evolution 18, 691 (2001)) and LG (V. Lennerz et al., Proceedings of the National Academy of Sciences of the United States of America 102, 16013 (2005))). Since ML is not limited to comparison of only closely related sequences, as is the case with MP based approaches, this estimation approach is expected to be the most accurate.

Calculation of log-odds matrix has been described in detail elsewhere (C. C. Dang, V. Lefort, V. S. Le, Q. S. Le, O. Gascuel, Bioinformatics 27, 2758 (2011)). Briefly, the standard model for amino acid substitution assumes a Markovian, time-continuous, time-reversible model represented by a 20×20 rate matrix $Q_{ij}$, where $q_{ij}$ (i≠j) is the number of substitutions from amino acid i to j per unit of time, and where diagonal elements are chosen to satisfy $$Q_{ii} = -\sum_{j \neq i} Q_{ij}.$$

Q can be decomposed such that $Q_{ij}=S_{ij} \cdot \pi_j$ for i≠j, where is a symmetric exchangeability matrix, and $\pi_i$ is the probability to observe amino acid i (C. C. Dang, V. Lefort, V. S. Le, Q. S. Le, O. Gascuel, Bioinformatics 27, 2758 (2011)). Finally, Q is normalized such that $$1 = -\sum_i \pi_i Q_{ii},$$

so that a time unit t=1.0 corresponds to 1.0 expected substitution per site, or one "accepted point mutation" per site, denoted by a PAM distance of 100 (M. O. Dayhoff, R. M. Schwartz, B. C. Orcutt, A model for evolutionary change. M O Dayhoff, ed. Atlas of protein sequence and structure Vol. 5, 345 (1978); S. Q. Le, O. Gascuel, Molecular biology and evolution 25, 1307 (2008); C. C. Dang, V. Lefort, V. S. Le, Q. S. Le, O. Gascuel, Bioinfoimatics 27, 2758 (2011)).

The probability for amino acid i to be replaced by amino acid j after time t, $Pr(i \to j|t) = P_{ij}(t)$, is given by the 20×20 probability matrix $P(t) = e^{tQ}$ (with notation denoting matrix exponentiation). The log-odds matrix calculated for time t is given by the log-odds 20×20 matrix $$T_{i,j} = 10\log_{10}\left(\frac{\pi_i P_{ij}(t)}{\pi_i \pi_j}\right)$$

(M. O. Dayhoff, R. M. Schwartz, B. C. Orcutt, A model for evolutionary change. M O Dayhoff, ed. Atlas of protein sequence and structure Vol. 5, 345 (1978, 1978)). A time-reversible mean that $\pi_i P_{ij}(t) = \pi_j P_{ji}(t)$, and therefore $T_{i,j}$ is symmetric (P. G. Higgs, T. K. Attwood, Bioinformatics and molecular evolution. (Wiley-Blackwell, 2009)).

The T score for the substitution i⇆j is defined here as $T_{i,j}$, and depends on the evolutionary model and the time t. We explored various models and PAM distances for the T score, including PAM, BLOSUM62, JTT, VT160, Gonnet, WAG, WAG*, and LG (see references above). The figures in this report were generated using a T score based on the WAG model and a PAM distance of 250. Such a large PAM distance means that there is substantial chance for the amino acid to change (P. G. Higgs, T. K. Attwood, Bioinformatics and molecular evolution. (Wiley-Blackwell, 2009)), and is useful in detecting distant relationships between sequences where residues may not be identical but the physico-chemical properties of the amino acids are conserved (M. O. Dayhoff, R. M. Schwartz, B. C. Orcutt, A model for evolutionary change. M O Dayhoff, ed. Atlas of protein sequence and structure Vol. 5, 345 (1978); P. G. Higgs, T. K. Attwood, Bioinformatics and molecular evolution. (Wiley-Blackwell, 2009)).

Using a t-distribution test statistic we compared the mean T scores of immunogenic versus non-immunogenic epitopes from Table 3 for the WAG matrix using various PAM scores (1, 10, 25, 50, 100, 150, 200, and 250). Analysis of the test statistic showed that the P value decreased monotonically with PAM distance, implying that a PAM distance of 250 was the optimal solution, as would be anticipated (data not shown). The classification into $H_A$ and $H_n$ was the same for all matrices except for the PAM matrix, which is the least accurate of all evolutionary models. Of all evolutionary models, the WAG250 model resulted in the maximum separation between $H_A$ and $H_n$ epitopes in Table 3, measuring separation with the test statistic: [max T score($H_A$)-min T score($H_n$)]/σ(T score ($H_A$), T score($H_n$)) (data not shown). The same test statistic was also maximal for a PAM distance 250 compared to smaller distance.

Published CD8+ Epitopes

CD8+ epitopes with single mutated amino acids were collected from the list of tumor antigens resulting from mutations published by the Cancer Immunity Journal (P. Van der Bruggen, V. Stroobant, N. Vigneron, B. Van den Eynde. (Cancer Immun, http://www.cancerimmunity.org/peptide/, 2013) (http://cancerimmunity.org/peptide/mutations/). HLA alleles were taken either from the published table or from the original paper if the latter was more precise. References listed in Table 4 are the following: (1) Lennerz et al. *PNAS* 102 (44), pp. 16013-16018 (2005); (2) Karanikas et al. *Cancer Res* 61 (9), pp. 3718-3724 (2001); (3) Sensi et al. *Cancer Res* 65 (2), pp. 632-640 (2005); (4) Linard et al. *J. Immunol* 168 (9), pp. 4802-4808 (2002); (5) Zorn et al. *Eur. J. Immunol* 29 (2), pp. 592-601 (1999); (6) Graf et al. *Blood* 109 (7), pp. 2985-2988 (2007); (7) Robbins et al. *J. Exp. Med* 183 (3), pp. 1185-1192 (1996); (8) Vigneron et al. *Cancer Immun* 2, pp. 9 (2002); (9) Echchakir et al. *Cancer Res* 61 (10), pp. 4078-1083 (2001); (10) Hogan et al. *Cancer Res* 58 (22), pp. 5144-5150 (1998); (11) Ito et al. *Int. J. Cancer* 120 (12), pp. 2618-2624 (2007); (12) Wölfel et al. *Science* 269 (5228), pp. 1281-1284 (1995); (13) Gjertsen et al. *Int. J. Cancer* 72 (5), pp. 784-790 (1997).

Example 3

Example of a Scheme for Weighing Mutation Scores to Improve Prioritization of Immunogenic Mutations RNA that is injected into the cell, once translated and cleaved into short peptides, can be presented on different HLA types within the cell. Therefore it stands to reason that the more HLA types that are predicted to have a low MHC consensus (or similar) score, the more likely a given mutation will be immunogenic since it can potentially be displayed on more than one HLA type in parallel. Thus, weighing mutations by the number of HLA types for which the mutation is classified as $H_A$ and/or $H_B UH_C$ or even weighing each mutation simply by the number of HLA types that have a low $M_{mut}$ score may improve immunogenicity ranking. In the most general solution, when we inject a 27 mer RNA or peptide into the cell, there is not just the freedom to select the HLA type, but also the length of the peptide and the position of the mutation within this peptide. Therefore, one can scan all possible HLA types, all possible window lengths and all possible positions for the mutation within the window and calculate the number of solutions (per given mutation) that are classified as $H_A$ and/or $H_B UH_C$ (FIG. 12). This may be an important weighing factor for mutation prioritization to select the most efficacious epitopes for vaccination. An example of a scatter plot of all these solutions as a function of $M_{mut}$ and $\Delta M=M_{mut}-M_{wt}$ is shown in FIG. 13.

The invention claimed is:

1. A method for producing a personalized cancer vaccine for a subject having a tumor, the method comprising the steps of:
   identifying from nucleic acid and/or peptide sequence data that is obtained from tumor and normal cells of a subject, a plurality of modified peptides expressed in the tumor, each comprising an amino acid substitution at a position, relative to a corresponding parent peptide expressed in the normal cells;
   ascertaining, for each of the plurality of modified peptides, via a computer-based analytical process each of:
   a) a first score for binding of the modified peptide to one or more MHC molecules by using a peptide:MHC binding predictive model, wherein the first score is indicative of a likelihood of the modified peptide binding to one or more MHC molecules, and
   b) a second score for binding of the corresponding parent peptide to the one or more MHC molecules by using the peptide:MHC binding predictive model, wherein the second score is indicative of a likelihood of the corresponding parent peptide binding to one or more MHC molecules, and thus the likelihood that TCRs binding the corresponding parent peptide would have been deleted during the subject's development, and
   c) a third score for chemical and physical dissimilarity between the amino acids at the position in the parent and modified peptides by referencing a substitution matrix that describes a rate at which one amino acid in a sequence changes over evolutionary time to determine the probability of observing the amino acid substitution over evolutionary time, and thus identifying those modified peptides in which the substituted amino acid has sufficiently different physico-chemical properties from the parent amino acid such that the subject's TCR repertoire is able to detect the modified peptide; and selecting, via a computer-based analytical process, from the plurality of modified peptides, as immunogenic to the subject's TCR repertoire at least one candidate modified peptide with respect to which:

(i) the first score satisfies a first pre-determined threshold indicating binding to the one or more MHC molecules such that the candidate modified peptide is MHC-presented; and (ii) the second score satisfies a second pre-determined threshold indicating binding to the one or more MHC molecules such that TCRs binding the corresponding parent peptide would have been deleted during the subject's development; and (iii) the third score for at least one amino acid substitution in the candidate modified peptide indicates a lower probability of observing the amino acid substitution over evolutionary time than at least one other modified peptides in the plurality; and producing a personalized cancer vaccine for the subject, which comprises a peptide or polypeptide comprising the at least one candidate modified peptide selected as immunogenic to the subject's TCR repertoire or a nucleic acid encoding the peptide or polypeptide.

2. The method of claim 1 further comprising the step: providing the vaccine to a patient in need thereof.

3. The method of claim 1 wherein the parent peptide has a germline amino acid at the position.

4. The method of claim 1 wherein the parent peptide and the modified peptide are each 8 to 15 amino acids in length.

5. The method of claim 1 wherein the first score and the second score are each ascertained for binding to more than one MHC molecule, and the MHC molecules comprise different MHC molecule types corresponding to different MHC alleles.

6. The method of claim 1 wherein the one or more MHC molecules are MHC class I molecules.

7. The method of claim 1 wherein the first score and/or the second score is/are ascertained by a computer-based analytical process comprising a sequence comparison with a database of MHC-binding motifs.

8. The method of claim 1 wherein the threshold applied with respect to the first score is different from the threshold applied with respect to the second score.

9. The method of claim 1 wherein the first and/or second pre-determined threshold reflects a probability for binding to one or more MHC molecules.

10. The method of claim 1 wherein the substitution matrix is or comprises an evolutionary based log-odds matrix.

11. The method of claim 1 wherein the modified peptide is selected as immunogenic if: (i) the parent peptide binds to one or more WIC molecules in standard assays, and (ii) the modified peptide binds to said one or more WIC molecules in standard assays, and (iii) the amino acids at the position in the modified and parent peptides are chemically and physically dissimilar.

12. The method of claim 1 wherein the position of the amino acid substitution is not an anchor position for binding to one or more WIC molecules.

13. The method of claim 1 wherein the position of the ammo acid substitution is an anchor position for binding to one or more WIC molecules.

14. The method of claim 1, wherein the plurality of modified peptides comprises two or more different modified peptides comprising the same amino acid substitution.

15. The method of claim 14 wherein the two or more different modified peptides comprising the same amino acid substitution comprise different fragments of a modified protein, said different fragments comprising the same amino acid substitution present in the modified protein.

16. The method of claim 14 wherein the two or more different modified peptides comprising the same amino acid substitution comprise all potential MHC binding fragments of a modified protein, said fragments comprising the same amino acid substitution present in the protein.

17. The method of claim 14 wherein the vaccine comprises at least one candidate modified peptides selected from the two or more different modified peptides comprising the same amino acid substitution.

18. The method of claim 14 wherein the two or more different modified peptides comprising the same amino acid substitution differ in length.

19. The method of claim 1, wherein the plurality of modified peptides comprises two or more different modified peptides each comprising a different amino acid substitution and the different amino acid substitutions are present in the same protein.

20. The method claim 14 which comprises comparing the first scores of two or more of said different modified peptides.

21. The method of claim 20 wherein the first score is weighted higher than the third score.

22. The method of claim 1 further comprising, prior to the step of identifying from the sequence data the plurality of modified peptides expressed in the tumor cells, identifying one or more non-synonymous mutations in one or more protein-coding regions encoding at least one of the modified peptides.

23. The method of claim 1 wherein the amino acid substitution is identified by sequencing a whole or partial genome or transcriptome of one or more cells.

24. The method of claim 22 wherein said mutations are somatic mutations.

25. The method of claim 22 wherein said mutations are cancer mutations.

26. The method of claim 1 wherein the one or more MHC molecules are MHC class II molecules.

27. The method of claim 1 wherein the first and the second scores are ascertained for binding to more than one MHC molecule, and the more than one MHC molecule comprise one or more MHC class I molecules and one or more MHC class II molecules.

28. The method of claim 1 wherein the subject is a human individual.

29. The method of claim 1 further comprising the step of determining that the tumor cells express the modified peptide.

30. The method of claim 1 further comprising the step of determining that the normal cells express the parent peptide.

31. The method of claim 29 further comprising the step of administering the vaccine to the subject.

32. The method of claim 30 further comprising the step of administering the vaccine to the subject, wherein the subject has a tumor that expresses the modified peptide.

33. The method of claim 14 wherein the two or more different modified peptides comprising the same amino acid substitution differ in the position of the amino acid substitution.

34. The method of claim 1, wherein the step of selecting comprises ranking at least two or more modified peptides in the plurality with reference to one or more of: their respective first scores, their respective second scores, and their respective third scores, thereby selecting, based on the ranking, at least one candidate modified peptide from the plurality of modified peptides that is more immunogenic to the subject's TCR repertoire than at least one other modified peptides in the plurality.

* * * * *

SEQUENCE LISTING

```
<160> NUMBER OF SEQ ID NOS: 94

<210> SEQ ID NO 1
<211> LENGTH: 15
<212> TYPE: PRT
<213> ORGANISM: Artificial Sequence
<220> FEATURE:
<223> OTHER INFORMATION: Linker sequence
<220> FEATURE:
<221> NAME/KEY: REPEAT
<222> LOCATION: (1)..(3)
<223> OTHER INFORMATION: Portion of sequence repeated a times, wherein a
``` is independently a number selected from 0, 1, 2, 3, 4, 5, 6, 7, 8,
       9, 10, 11, 12, 13, 14, 15, 16, 17, 18, 19, or 20
<220> FEATURE:
<221> NAME/KEY: MISC_FEATURE
<222> LOCATION: (1)..(15)
<223> OTHER INFORMATION: a + b + c + d + e are different from 0 and
       preferably are 2 or more, 3 or more, 4 or more or 5 or more
<220> FEATURE:
<221> NAME/KEY: REPEAT
<222> LOCATION: (4)..(6)
<223> OTHER INFORMATION: Portion of sequence repeated b times, wherein b
       is independently a number selected from 0, 1, 2, 3, 4, 5, 6, 7, 8,
       9, 10, 11, 12, 13, 14, 15, 16, 17, 18, 19, or 20
<220> FEATURE:
<221> NAME/KEY: REPEAT
<222> LOCATION: (7)..(9)
<223> OTHER INFORMATION: Portion of sequence repeated c times, wherein c
       is independently a number selected from 0, 1, 2, 3, 4, 5, 6, 7, 8,
       9, 10, 11, 12, 13, 14, 15, 16, 17, 18, 19, or 20
<220> FEATURE:
<221> NAME/KEY: REPEAT
<222> LOCATION: (10)..(12)
<223> OTHER INFORMATION: Portion of sequence repeated d times, wherein d
       is independently a number selected from 0, 1, 2, 3, 4, 5, 6, 7, 8,
       9, 10, 11, 12, 13, 14, 15, 16, 17, 18, 19, or 20
<220> FEATURE:
<221> NAME/KEY: REPEAT
<222> LOCATION: (13)..(15)
<223> OTHER INFORMATION: Portion of sequence repeated e times, wherein e
       is independently a number selected from 0, 1, 2, 3, 4, 5, 6, 7, 8,
       9, 10, 11, 12, 13, 14, 15, 16, 17, 18, 19, or 20

<400> SEQUENCE: 1

Gly Gly Ser Gly Ser Ser Gly Gly Gly Ser Ser Gly Gly Ser Gly
1               5                   10                  15

<210> SEQ ID NO 2
<211> LENGTH: 9
<212> TYPE: PRT
<213> ORGANISM: Artificial Sequence
<220> FEATURE:
<223> OTHER INFORMATION: Linker sequence

<400> SEQUENCE: 2

Gly Gly Ser Gly Gly Gly Gly Ser Gly
1               5

<210> SEQ ID NO 3
<211> LENGTH: 11
<212> TYPE: PRT
<213> ORGANISM: Artificial Sequence
<220> FEATURE:
<223> OTHER INFORMATION: Epitope

<400> SEQUENCE: 3

Ala Ala Val Ile Leu Arg Asp Ala Leu His Met
1               5                   10

<210> SEQ ID NO 4
<211> LENGTH: 11
<212> TYPE: PRT
<213> ORGANISM: Artificial Sequence
<220> FEATURE:
<223> OTHER INFORMATION: Epitope

<400> SEQUENCE: 4

Ala Ala Val Ile Leu Arg Val Ala Leu His Met
1               5                   10

<210> SEQ ID NO 5
<211> LENGTH: 9

```
<212> TYPE: PRT
<213> ORGANISM: Artificial Sequence
<220> FEATURE:
<223> OTHER INFORMATION: Epitope

<400> SEQUENCE: 5

Gly Gly Pro Gly Ser Glu Lys Ser Leu
1               5

<210> SEQ ID NO 6
<211> LENGTH: 9
<212> TYPE: PRT
<213> ORGANISM: Artificial Sequence
<220> FEATURE:
<223> OTHER INFORMATION: Epitope

<400> SEQUENCE: 6

Gly Gly Pro Gly Ser Gly Lys Ser Leu
1               5

<210> SEQ ID NO 7
<211> LENGTH: 10
<212> TYPE: PRT
<213> ORGANISM: Artificial Sequence
<220> FEATURE:
<223> OTHER INFORMATION: Epitope

<400> SEQUENCE: 7

Leu Ala Leu Pro Asn Asn Tyr Cys Asp Val
1               5                   10

<210> SEQ ID NO 8
<211> LENGTH: 10
<212> TYPE: PRT
<213> ORGANISM: Artificial Sequence
<220> FEATURE:
<223> OTHER INFORMATION: Epitope

<400> SEQUENCE: 8

Leu Ala Leu Pro Asn Asn Tyr Cys Asp Phe
1               5                   10

<210> SEQ ID NO 9
<211> LENGTH: 10
<212> TYPE: PRT
<213> ORGANISM: Artificial Sequence
<220> FEATURE:
<223> OTHER INFORMATION: Epitope

<400> SEQUENCE: 9

Ser His Leu Asn Asn Asp Val Trp Gln Ile
1               5                   10

<210> SEQ ID NO 10
<211> LENGTH: 10
<212> TYPE: PRT
<213> ORGANISM: Artificial Sequence
<220> FEATURE:
<223> OTHER INFORMATION: Epitope

<400> SEQUENCE: 10

Ser His Leu Asn Asn Asp Phe Trp Gln Ile
1               5                   10

<210> SEQ ID NO 11
<211> LENGTH: 9
<212> TYPE: PRT
```

```
<213> ORGANISM: Artificial Sequence
<220> FEATURE:
<223> OTHER INFORMATION: Epitope

<400> SEQUENCE: 11

Tyr Tyr Met Arg Asp Val Ile Ala Ile
1               5

<210> SEQ ID NO 12
<211> LENGTH: 9
<212> TYPE: PRT
<213> ORGANISM: Artificial Sequence
<220> FEATURE:
<223> OTHER INFORMATION: Epitope

<400> SEQUENCE: 12

Tyr Tyr Met Arg Asp Val Thr Ala Ile
1               5

<210> SEQ ID NO 13
<211> LENGTH: 10
<212> TYPE: PRT
<213> ORGANISM: Artificial Sequence
<220> FEATURE:
<223> OTHER INFORMATION: Epitope

<400> SEQUENCE: 13

Thr Tyr Leu Gln Pro Ala Gln Ala Gln Met
1               5                   10

<210> SEQ ID NO 14
<211> LENGTH: 10
<212> TYPE: PRT
<213> ORGANISM: Artificial Sequence
<220> FEATURE:
<223> OTHER INFORMATION: Epitope

<400> SEQUENCE: 14

Ile Tyr Leu Gln Pro Ala Gln Ala Gln Met
1               5                   10

<210> SEQ ID NO 15
<211> LENGTH: 8
<212> TYPE: PRT
<213> ORGANISM: Artificial Sequence
<220> FEATURE:
<223> OTHER INFORMATION: Epitope

<400> SEQUENCE: 15

Gln Ser Leu Gly Phe Thr Tyr Leu
1               5

<210> SEQ ID NO 16
<211> LENGTH: 8
<212> TYPE: PRT
<213> ORGANISM: Artificial Sequence
<220> FEATURE:
<223> OTHER INFORMATION: Epitope

<400> SEQUENCE: 16

Gln Arg Leu Gly Phe Thr Tyr Leu
1               5

<210> SEQ ID NO 17
<211> LENGTH: 10
<212> TYPE: PRT
<213> ORGANISM: Artificial Sequence
```

```
<220> FEATURE:
<223> OTHER INFORMATION: Epitope

<400> SEQUENCE: 17

Glu Tyr Trp Ala Ser Arg Ala Leu Asp Ser
1               5                   10

<210> SEQ ID NO 18
<211> LENGTH: 10
<212> TYPE: PRT
<213> ORGANISM: Artificial Sequence
<220> FEATURE:
<223> OTHER INFORMATION: Epitope

<400> SEQUENCE: 18

Glu Tyr Trp Ala Ser Arg Ala Leu Gly Ser
1               5                   10

<210> SEQ ID NO 19
<211> LENGTH: 10
<212> TYPE: PRT
<213> ORGANISM: Artificial Sequence
<220> FEATURE:
<223> OTHER INFORMATION: Epitope

<400> SEQUENCE: 19

Gly Tyr Leu Gln Phe Ala Tyr Glu Gly Cys
1               5                   10

<210> SEQ ID NO 20
<211> LENGTH: 10
<212> TYPE: PRT
<213> ORGANISM: Artificial Sequence
<220> FEATURE:
<223> OTHER INFORMATION: Epitope

<400> SEQUENCE: 20

Gly Tyr Leu Gln Phe Ala Tyr Glu Gly Arg
1               5                   10

<210> SEQ ID NO 21
<211> LENGTH: 11
<212> TYPE: PRT
<213> ORGANISM: Artificial Sequence
<220> FEATURE:
<223> OTHER INFORMATION: Epitope

<400> SEQUENCE: 21

Val Thr Phe Gln Ala Phe Ile Asp Val Met Ser
1               5                   10

<210> SEQ ID NO 22
<211> LENGTH: 11
<212> TYPE: PRT
<213> ORGANISM: Artificial Sequence
<220> FEATURE:
<223> OTHER INFORMATION: Epitope

<400> SEQUENCE: 22

Val Thr Phe Gln Ala Phe Ile Asp Phe Met Ser
1               5                   10

<210> SEQ ID NO 23
<211> LENGTH: 10
<212> TYPE: PRT
<213> ORGANISM: Artificial Sequence
<220> FEATURE:
```

<223> OTHER INFORMATION: Epitope

<400> SEQUENCE: 23

Pro Tyr Leu Thr Ala Leu Asp Asp Leu Leu
1               5                   10

<210> SEQ ID NO 24
<211> LENGTH: 10
<212> TYPE: PRT
<213> ORGANISM: Artificial Sequence
<220> FEATURE:
<223> OTHER INFORMATION: Epitope

<400> SEQUENCE: 24

Pro Tyr Leu Thr Ala Leu Gly Asp Leu Leu
1               5                   10

<210> SEQ ID NO 25
<211> LENGTH: 10
<212> TYPE: PRT
<213> ORGANISM: Artificial Sequence
<220> FEATURE:
<223> OTHER INFORMATION: Epitope

<400> SEQUENCE: 25

Ala Gly Gly Leu Phe Val Ala Asp Ala Ile
1               5                   10

<210> SEQ ID NO 26
<211> LENGTH: 10
<212> TYPE: PRT
<213> ORGANISM: Artificial Sequence
<220> FEATURE:
<223> OTHER INFORMATION: Epitope

<400> SEQUENCE: 26

Ala Gly Gly Leu Phe Val Ala Asp Glu Ile
1               5                   10

<210> SEQ ID NO 27
<211> LENGTH: 10
<212> TYPE: PRT
<213> ORGANISM: Artificial Sequence
<220> FEATURE:
<223> OTHER INFORMATION: Epitope

<400> SEQUENCE: 27

Val Gly Ile Asn Phe Leu Gln Ser Tyr Gln
1               5                   10

<210> SEQ ID NO 28
<211> LENGTH: 10
<212> TYPE: PRT
<213> ORGANISM: Artificial Sequence
<220> FEATURE:
<223> OTHER INFORMATION: Epitope

<400> SEQUENCE: 28

Val Gly Ile Asn Ser Leu Gln Ser Tyr Gln
1               5                   10

<210> SEQ ID NO 29
<211> LENGTH: 9
<212> TYPE: PRT
<213> ORGANISM: Artificial Sequence
<220> FEATURE:
<223> OTHER INFORMATION: Epitope

<400> SEQUENCE: 29

Thr Arg Pro Ala Arg Asp Gly Thr Phe
1               5

<210> SEQ ID NO 30
<211> LENGTH: 9
<212> TYPE: PRT
<213> ORGANISM: Artificial Sequence
<220> FEATURE:
<223> OTHER INFORMATION: Epitope

<400> SEQUENCE: 30

Thr Arg Pro Ala Gly Asp Gly Thr Phe
1               5

<210> SEQ ID NO 31
<211> LENGTH: 9
<212> TYPE: PRT
<213> ORGANISM: Artificial Sequence
<220> FEATURE:
<223> OTHER INFORMATION: Epitope

<400> SEQUENCE: 31

Glu Pro Gln Ile Ala Met Asp Asp Met
1               5

<210> SEQ ID NO 32
<211> LENGTH: 9
<212> TYPE: PRT
<213> ORGANISM: Artificial Sequence
<220> FEATURE:
<223> OTHER INFORMATION: Epitope

<400> SEQUENCE: 32

Glu Pro Gln Ile Asp Met Asp Asp Met
1               5

<210> SEQ ID NO 33
<211> LENGTH: 9
<212> TYPE: PRT
<213> ORGANISM: Artificial Sequence
<220> FEATURE:
<223> OTHER INFORMATION: Epitope

<400> SEQUENCE: 33

Ile Ala Met Gln Asn Thr Thr Gln Leu
1               5

<210> SEQ ID NO 34
<211> LENGTH: 9
<212> TYPE: PRT
<213> ORGANISM: Artificial Sequence
<220> FEATURE:
<223> OTHER INFORMATION: Epitope

<400> SEQUENCE: 34

Ile Ala Ile Gln Asn Thr Thr Gln Leu
1               5

<210> SEQ ID NO 35
<211> LENGTH: 10
<212> TYPE: PRT
<213> ORGANISM: Artificial Sequence
<220> FEATURE:
<223> OTHER INFORMATION: Epitope

<400> SEQUENCE: 35

Ala Ile Tyr His His Ala Ser Arg Ala Ile
1               5                   10

<210> SEQ ID NO 36
<211> LENGTH: 10
<212> TYPE: PRT
<213> ORGANISM: Artificial Sequence
<220> FEATURE:
<223> OTHER INFORMATION: Epitope

<400> SEQUENCE: 36

Ala Ile Tyr Tyr His Ala Ser Arg Ala Ile
1               5                   10

<210> SEQ ID NO 37
<211> LENGTH: 10
<212> TYPE: PRT
<213> ORGANISM: Artificial Sequence
<220> FEATURE:
<223> OTHER INFORMATION: Epitope

<400> SEQUENCE: 37

Ser Tyr Ile Ala Leu Val Asp Lys Asn Ile
1               5                   10

<210> SEQ ID NO 38
<211> LENGTH: 10
<212> TYPE: PRT
<213> ORGANISM: Artificial Sequence
<220> FEATURE:
<223> OTHER INFORMATION: Epitope

<400> SEQUENCE: 38

Ser Tyr Leu Ala Leu Val Asp Lys Asn Ile
1               5                   10

<210> SEQ ID NO 39
<211> LENGTH: 9
<212> TYPE: PRT
<213> ORGANISM: Artificial Sequence
<220> FEATURE:
<223> OTHER INFORMATION: Epitope

<400> SEQUENCE: 39

Val Ile Pro Ile Leu Glu Met Gln Phe
1               5

<210> SEQ ID NO 40
<211> LENGTH: 9
<212> TYPE: PRT
<213> ORGANISM: Artificial Sequence
<220> FEATURE:
<223> OTHER INFORMATION: Epitope

<400> SEQUENCE: 40

Val Ile Pro Ile Leu Glu Val Gln Phe
1               5

<210> SEQ ID NO 41
<211> LENGTH: 10
<212> TYPE: PRT
<213> ORGANISM: Artificial Sequence
<220> FEATURE:
<223> OTHER INFORMATION: Epitope

<400> SEQUENCE: 41

Gly Tyr Leu Gln Phe Ala Tyr Asp Gly Arg
1               5                   10

<210> SEQ ID NO 42
<211> LENGTH: 10
<212> TYPE: PRT
<213> ORGANISM: Artificial Sequence
<220> FEATURE:
<223> OTHER INFORMATION: Epitope

<400> SEQUENCE: 42

Gly Tyr Leu Gln Phe Ala Tyr Glu Gly Arg
1               5                   10

<210> SEQ ID NO 43
<211> LENGTH: 10
<212> TYPE: PRT
<213> ORGANISM: Artificial Sequence
<220> FEATURE:
<223> OTHER INFORMATION: Epitope

<400> SEQUENCE: 43

Val Tyr Leu Asn Leu Leu Leu Lys Phe Thr
1               5                   10

<210> SEQ ID NO 44
<211> LENGTH: 10
<212> TYPE: PRT
<213> ORGANISM: Artificial Sequence
<220> FEATURE:
<223> OTHER INFORMATION: Epitope

<400> SEQUENCE: 44

Val Tyr Leu Asn Leu Phe Leu Lys Phe Thr
1               5                   10

<210> SEQ ID NO 45
<211> LENGTH: 9
<212> TYPE: PRT
<213> ORGANISM: Artificial Sequence
<220> FEATURE:
<223> OTHER INFORMATION: Epitope

<400> SEQUENCE: 45

Lys Ile Phe Ser Glu Val Thr Leu Lys
1               5

<210> SEQ ID NO 46
<211> LENGTH: 9
<212> TYPE: PRT
<213> ORGANISM: Artificial Sequence
<220> FEATURE:
<223> OTHER INFORMATION: Epitope

<400> SEQUENCE: 46

Lys Ile Phe Ser Glu Val Thr Pro Lys
1               5

<210> SEQ ID NO 47
<211> LENGTH: 9
<212> TYPE: PRT
<213> ORGANISM: Artificial Sequence
<220> FEATURE:
<223> OTHER INFORMATION: Epitope

<400> SEQUENCE: 47

Ser His Glu Thr Val Ile Ile Glu Leu
1               5

<210> SEQ ID NO 48
<211> LENGTH: 9
<212> TYPE: PRT
<213> ORGANISM: Artificial Sequence
<220> FEATURE:
<223> OTHER INFORMATION: Epitope

<400> SEQUENCE: 48

Ser His Glu Thr Val Thr Ile Glu Leu
1               5

<210> SEQ ID NO 49
<211> LENGTH: 9
<212> TYPE: PRT
<213> ORGANISM: Artificial Sequence
<220> FEATURE:
<223> OTHER INFORMATION: Epitope

<400> SEQUENCE: 49

Phe Leu Asp Glu Phe Met Glu Gly Val
1               5

<210> SEQ ID NO 50
<211> LENGTH: 9
<212> TYPE: PRT
<213> ORGANISM: Artificial Sequence
<220> FEATURE:
<223> OTHER INFORMATION: Epitope

<400> SEQUENCE: 50

Phe Leu Asp Glu Phe Met Glu Ala Val
1               5

<210> SEQ ID NO 51
<211> LENGTH: 9
<212> TYPE: PRT
<213> ORGANISM: Artificial Sequence
<220> FEATURE:
<223> OTHER INFORMATION: Epitope

<400> SEQUENCE: 51

Arg Pro His Val Pro Glu Ser Ala Phe
1               5

<210> SEQ ID NO 52
<211> LENGTH: 9
<212> TYPE: PRT
<213> ORGANISM: Artificial Sequence
<220> FEATURE:
<223> OTHER INFORMATION: Epitope

<400> SEQUENCE: 52

Gly Pro His Val Pro Glu Ser Ala Phe
1               5

<210> SEQ ID NO 53
<211> LENGTH: 10
<212> TYPE: PRT
<213> ORGANISM: Artificial Sequence
<220> FEATURE:
<223> OTHER INFORMATION: Epitope

<400> SEQUENCE: 53

Leu Leu Leu Asp Asp Leu Leu Val Ser Ile

```
1               5                   10
```

<210> SEQ ID NO 54
<211> LENGTH: 10
<212> TYPE: PRT
<213> ORGANISM: Artificial Sequence
<220> FEATURE:
<223> OTHER INFORMATION: Epitope

<400> SEQUENCE: 54

```
Leu Leu Leu Asp Asp Ser Leu Val Ser Ile
1               5                   10
```

<210> SEQ ID NO 55
<211> LENGTH: 10
<212> TYPE: PRT
<213> ORGANISM: Artificial Sequence
<220> FEATURE:
<223> OTHER INFORMATION: Epitope

<400> SEQUENCE: 55

```
Ile Leu Asp Thr Ala Gly Arg Glu Glu Tyr
1               5                   10
```

<210> SEQ ID NO 56
<211> LENGTH: 10
<212> TYPE: PRT
<213> ORGANISM: Artificial Sequence
<220> FEATURE:
<223> OTHER INFORMATION: Epitope

<400> SEQUENCE: 56

```
Ile Leu Asp Thr Ala Gly Gln Glu Glu Tyr
1               5                   10
```

<210> SEQ ID NO 57
<211> LENGTH: 9
<212> TYPE: PRT
<213> ORGANISM: Artificial Sequence
<220> FEATURE:
<223> OTHER INFORMATION: Epitope

<400> SEQUENCE: 57

```
Glu Thr Val Ser Glu Gln Ser Asn Val
1               5
```

<210> SEQ ID NO 58
<211> LENGTH: 9
<212> TYPE: PRT
<213> ORGANISM: Artificial Sequence
<220> FEATURE:
<223> OTHER INFORMATION: Epitope

<400> SEQUENCE: 58

```
Glu Thr Val Ser Glu Glu Ser Asn Val
1               5
```

<210> SEQ ID NO 59
<211> LENGTH: 10
<212> TYPE: PRT
<213> ORGANISM: Artificial Sequence
<220> FEATURE:
<223> OTHER INFORMATION: Epitope

<400> SEQUENCE: 59

```
Lys Ile Leu Asp Ala Val Val Ala Gln Lys
1               5                   10
```

```
<210> SEQ ID NO 60
<211> LENGTH: 10
<212> TYPE: PRT
<213> ORGANISM: Artificial Sequence
<220> FEATURE:
<223> OTHER INFORMATION: Epitope

<400> SEQUENCE: 60

Lys Ile Leu Asp Ala Val Val Ala Gln Glu
1               5                   10

<210> SEQ ID NO 61
<211> LENGTH: 9
<212> TYPE: PRT
<213> ORGANISM: Artificial Sequence
<220> FEATURE:
<223> OTHER INFORMATION: Epitope

<400> SEQUENCE: 61

Lys Ile Asn Lys Asn Pro Lys Tyr Lys
1               5

<210> SEQ ID NO 62
<211> LENGTH: 9
<212> TYPE: PRT
<213> ORGANISM: Artificial Sequence
<220> FEATURE:
<223> OTHER INFORMATION: Epitope

<400> SEQUENCE: 62

Glu Ile Asn Lys Asn Pro Lys Tyr Lys
1               5

<210> SEQ ID NO 63
<211> LENGTH: 10
<212> TYPE: PRT
<213> ORGANISM: Artificial Sequence
<220> FEATURE:
<223> OTHER INFORMATION: Epitope

<400> SEQUENCE: 63

Tyr Val Asp Phe Arg Glu Tyr Glu Tyr Tyr
1               5                   10

<210> SEQ ID NO 64
<211> LENGTH: 10
<212> TYPE: PRT
<213> ORGANISM: Artificial Sequence
<220> FEATURE:
<223> OTHER INFORMATION: Epitope

<400> SEQUENCE: 64

Tyr Val Asp Phe Arg Glu Tyr Glu Tyr Asp
1               5                   10

<210> SEQ ID NO 65
<211> LENGTH: 9
<212> TYPE: PRT
<213> ORGANISM: Artificial Sequence
<220> FEATURE:
<223> OTHER INFORMATION: Epitope

<400> SEQUENCE: 65

Ser Tyr Leu Asp Ser Gly Ile His Phe
1               5
```

<210> SEQ ID NO 66
<211> LENGTH: 9
<212> TYPE: PRT
<213> ORGANISM: Artificial Sequence
<220> FEATURE:
<223> OTHER INFORMATION: Epitope

<400> SEQUENCE: 66

Ser Tyr Leu Asp Ser Gly Ile His Ser
1               5

<210> SEQ ID NO 67
<211> LENGTH: 9
<212> TYPE: PRT
<213> ORGANISM: Artificial Sequence
<220> FEATURE:
<223> OTHER INFORMATION: Epitope

<400> SEQUENCE: 67

Lys Glu Leu Glu Gly Ile Leu Leu Leu
1               5

<210> SEQ ID NO 68
<211> LENGTH: 9
<212> TYPE: PRT
<213> ORGANISM: Artificial Sequence
<220> FEATURE:
<223> OTHER INFORMATION: Epitope

<400> SEQUENCE: 68

Lys Glu Leu Glu Gly Ile Leu Leu Pro
1               5

<210> SEQ ID NO 69
<211> LENGTH: 10
<212> TYPE: PRT
<213> ORGANISM: Artificial Sequence
<220> FEATURE:
<223> OTHER INFORMATION: Epitope

<400> SEQUENCE: 69

Thr Leu Asp Trp Leu Leu Gln Thr Pro Lys
1               5                   10

<210> SEQ ID NO 70
<211> LENGTH: 10
<212> TYPE: PRT
<213> ORGANISM: Artificial Sequence
<220> FEATURE:
<223> OTHER INFORMATION: Epitope

<400> SEQUENCE: 70

Thr Leu Gly Trp Leu Leu Gln Thr Pro Lys
1               5                   10

<210> SEQ ID NO 71
<211> LENGTH: 10
<212> TYPE: PRT
<213> ORGANISM: Artificial Sequence
<220> FEATURE:
<223> OTHER INFORMATION: Epitope

<400> SEQUENCE: 71

Phe Ile Ala Ser Asn Gly Val Lys Leu Val
1               5                   10

<210> SEQ ID NO 72
<211> LENGTH: 10
<212> TYPE: PRT
<213> ORGANISM: Artificial Sequence
<220> FEATURE:
<223> OTHER INFORMATION: Epitope

<400> SEQUENCE: 72

Phe Ile Ala Ser Lys Gly Val Lys Leu Val
1               5                   10

<210> SEQ ID NO 73
<211> LENGTH: 9
<212> TYPE: PRT
<213> ORGANISM: Artificial Sequence
<220> FEATURE:
<223> OTHER INFORMATION: Epitope

<400> SEQUENCE: 73

Val Val Pro Cys Glu Pro Pro Glu Val
1               5

<210> SEQ ID NO 74
<211> LENGTH: 9
<212> TYPE: PRT
<213> ORGANISM: Artificial Sequence
<220> FEATURE:
<223> OTHER INFORMATION: Epitope

<400> SEQUENCE: 74

Val Val Pro Tyr Glu Pro Pro Glu Val
1               5

<210> SEQ ID NO 75
<211> LENGTH: 10
<212> TYPE: PRT
<213> ORGANISM: Artificial Sequence
<220> FEATURE:
<223> OTHER INFORMATION: Epitope

<400> SEQUENCE: 75

Ala Cys Asp Pro His Ser Gly His Phe Val
1               5                   10

<210> SEQ ID NO 76
<211> LENGTH: 10
<212> TYPE: PRT
<213> ORGANISM: Artificial Sequence
<220> FEATURE:
<223> OTHER INFORMATION: Epitope

<400> SEQUENCE: 76

Ala Arg Asp Pro His Ser Gly His Phe Val
1               5                   10

<210> SEQ ID NO 77
<211> LENGTH: 9
<212> TYPE: PRT
<213> ORGANISM: Artificial Sequence
<220> FEATURE:
<223> OTHER INFORMATION: Epitope

<400> SEQUENCE: 77

Val Val Val Gly Ala Val Gly Val Gly
1               5

<210> SEQ ID NO 78

```
<211> LENGTH: 9
<212> TYPE: PRT
<213> ORGANISM: Artificial Sequence
<220> FEATURE:
<223> OTHER INFORMATION: Epitope

<400> SEQUENCE: 78

Val Val Val Gly Ala Gly Gly Val Gly
1               5

<210> SEQ ID NO 79
<211> LENGTH: 9
<212> TYPE: PRT
<213> ORGANISM: Artificial Sequence
<220> FEATURE:
<223> OTHER INFORMATION: Epitope

<400> SEQUENCE: 79

Gly Leu Ala Gly Gly Leu Leu Ala Leu
1               5

<210> SEQ ID NO 80
<211> LENGTH: 9
<212> TYPE: PRT
<213> ORGANISM: Artificial Sequence
<220> FEATURE:
<223> OTHER INFORMATION: Epitope

<400> SEQUENCE: 80

Val Leu Phe Trp Gly Leu Leu Leu Leu
1               5

<210> SEQ ID NO 81
<211> LENGTH: 9
<212> TYPE: PRT
<213> ORGANISM: Artificial Sequence
<220> FEATURE:
<223> OTHER INFORMATION: Epitope

<400> SEQUENCE: 81

Gly Ile Leu Gly Trp Val Leu Tyr Leu
1               5

<210> SEQ ID NO 82
<211> LENGTH: 9
<212> TYPE: PRT
<213> ORGANISM: Artificial Sequence
<220> FEATURE:
<223> OTHER INFORMATION: Epitope

<400> SEQUENCE: 82

Val Leu Phe Trp Gly Leu Leu Phe Tyr
1               5

<210> SEQ ID NO 83
<211> LENGTH: 9
<212> TYPE: PRT
<213> ORGANISM: Artificial Sequence
<220> FEATURE:
<223> OTHER INFORMATION: Epitope

<400> SEQUENCE: 83

Gly Leu Ala Gly Gly Leu Leu Ala Tyr
1               5

<210> SEQ ID NO 84
<211> LENGTH: 9
```

```
<212> TYPE: PRT
<213> ORGANISM: Artificial Sequence
<220> FEATURE:
<223> OTHER INFORMATION: Epitope

<400> SEQUENCE: 84

Val Ile Phe Trp Gly Leu Leu Val Leu
1               5

<210> SEQ ID NO 85
<211> LENGTH: 10
<212> TYPE: PRT
<213> ORGANISM: Artificial Sequence
<220> FEATURE:
<223> OTHER INFORMATION: Epitope

<400> SEQUENCE: 85

Lys Ile Leu Asp Ala Val Val Ala Gln Glu
1               5                   10

<210> SEQ ID NO 86
<211> LENGTH: 10
<212> TYPE: PRT
<213> ORGANISM: Artificial Sequence
<220> FEATURE:
<223> OTHER INFORMATION: Epitope

<400> SEQUENCE: 86

Lys Ile Leu Asp Ala Val Val Ala Gln Lys
1               5                   10

<210> SEQ ID NO 87
<211> LENGTH: 9
<212> TYPE: PRT
<213> ORGANISM: Artificial Sequence
<220> FEATURE:
<223> OTHER INFORMATION: Epitope

<400> SEQUENCE: 87

Gln His Ser Ala Ala Pro Gly Pro Pro
1               5

<210> SEQ ID NO 88
<211> LENGTH: 9
<212> TYPE: PRT
<213> ORGANISM: Artificial Sequence
<220> FEATURE:
<223> OTHER INFORMATION: Epitope

<400> SEQUENCE: 88

Gln His Ser Ala Ala Pro Gly Pro Leu
1               5

<210> SEQ ID NO 89
<211> LENGTH: 9
<212> TYPE: PRT
<213> ORGANISM: Artificial Sequence
<220> FEATURE:
<223> OTHER INFORMATION: Epitope

<400> SEQUENCE: 89

Glu Ile Asn Lys Asn Pro Lys Tyr Lys
1               5

<210> SEQ ID NO 90
<211> LENGTH: 9
<212> TYPE: PRT
```

```
<213> ORGANISM: Artificial Sequence
<220> FEATURE:
<223> OTHER INFORMATION: Epitope

<400> SEQUENCE: 90

Lys Ile Asn Lys Asn Pro Lys Tyr Lys
1               5

<210> SEQ ID NO 91
<211> LENGTH: 10
<212> TYPE: PRT
<213> ORGANISM: Artificial Sequence
<220> FEATURE:
<223> OTHER INFORMATION: Epitope

<400> SEQUENCE: 91

Tyr Val Asp Phe Arg Glu Tyr Glu Tyr Asp
1               5                   10

<210> SEQ ID NO 92
<211> LENGTH: 10
<212> TYPE: PRT
<213> ORGANISM: Artificial Sequence
<220> FEATURE:
<223> OTHER INFORMATION: Epitope

<400> SEQUENCE: 92

Tyr Val Asp Phe Arg Glu Tyr Glu Tyr Tyr
1               5                   10

<210> SEQ ID NO 93
<211> LENGTH: 9
<212> TYPE: PRT
<213> ORGANISM: Artificial Sequence
<220> FEATURE:
<223> OTHER INFORMATION: Epitope

<400> SEQUENCE: 93

Ser Tyr Leu Asp Ser Gly Ile His Ser
1               5

<210> SEQ ID NO 94
<211> LENGTH: 9
<212> TYPE: PRT
<213> ORGANISM: Artificial Sequence
<220> FEATURE:
<223> OTHER INFORMATION: Epitope

<400> SEQUENCE: 94

Ser Tyr Leu Asp Ser Gly Ile His Phe
1               5
```